US011723957B2

(12) United States Patent
Nazarian et al.

(10) Patent No.: US 11,723,957 B2
(45) Date of Patent: Aug. 15, 2023

(54) COMPOSITIONS COMPRISING RELAXIN AND METHODS OF USE THEREOF

(71) Applicants: Beth Israel Deaconess Medical Center, Inc., Boston, MA (US); Trustees of Boston University, Boston, MA (US)

(72) Inventors: Ara Nazarian, Wellesley, MA (US); Edward Rodriguez, Medfield, MA (US); Mark Grinstaff, Boston, MA (US)

(73) Assignees: Beth Israel Deaconess Medical Center, Inc., Boston, MA (US); Trustees of Boston University, Boston, MA (US)

(*) Notice: Subject to any disclaimer, the term of this patent is extended or adjusted under 35 U.S.C. 154(b) by 229 days.

(21) Appl. No.: 16/339,659

(22) PCT Filed: Oct. 9, 2017

(86) PCT No.: PCT/US2017/055799
§ 371 (c)(1),
(2) Date: Apr. 4, 2019

(87) PCT Pub. No.: WO2018/068047
PCT Pub. Date: Apr. 12, 2018

(65) Prior Publication Data
US 2019/0282665 A1    Sep. 19, 2019

Related U.S. Application Data

(60) Provisional application No. 62/405,795, filed on Oct. 7, 2016.

(51) Int. Cl.
| | | |
|---|---|---|
| *A61K 38/22* | (2006.01) | |
| *C07K 14/575* | (2006.01) | |
| *C07K 1/107* | (2006.01) | |
| *A61K 47/69* | (2017.01) | |
| *A61K 47/60* | (2017.01) | |
| *A61P 19/02* | (2006.01) | |
| *A61K 9/00* | (2006.01) | |
| *A61K 9/16* | (2006.01) | |
| *A61K 47/42* | (2017.01) | |
| *A61M 3/00* | (2006.01) | |

(52) U.S. Cl.
CPC ........ *A61K 38/2221* (2013.01); *A61K 9/0019* (2013.01); *A61K 9/16* (2013.01); *A61K 47/42* (2013.01); *A61K 47/60* (2017.08); *A61K 47/6903* (2017.08); *A61M 3/005* (2013.01); *A61P 19/02* (2018.01); *A61M 2202/07* (2013.01); *C07K 1/107* (2013.01); *C07K 14/575* (2013.01)

(58) Field of Classification Search
None
See application file for complete search history.

(56) References Cited

U.S. PATENT DOCUMENTS

| 8,404,268 | B2 | 3/2013 | Lee et al. | |
|---|---|---|---|---|
| 2002/0022593 | A1* | 2/2002 | Yue | A61K 38/2221 |
| | | | | 514/12.7 |
| 2005/0143299 | A1* | 6/2005 | Bigazzi | A61P 9/10 |
| | | | | 514/17.7 |
| 2014/0194357 | A1 | 7/2014 | Kraynov et al. | |
| 2016/0296600 | A1* | 10/2016 | Sprogoe | A61K 9/0019 |
| 2019/0263882 | A1* | 8/2019 | Wang | A61K 9/10 |

FOREIGN PATENT DOCUMENTS

| WO | 2015/067791 A1 | 5/2015 |
|---|---|---|
| WO | 2017/100540 A2 † | 6/2017 |
| WO | 2017/100540 A3 | 7/2017 |

OTHER PUBLICATIONS

Bathgate et al. Relaxin Family Peptides and Their Receptors; Physiol Rev 93: 405-480 (2013). (Year: 2013).*
Bhattacharya et al. Impact of genetic variation on three dimensional structure and function of proteins; PLOS One 12(3): e0171355, pp. 1-22 (Mar. 2017). (Year: 2017).*
Tokuriki et al. (Stability effects of mutations ana protein evolvability; Current Opinion in Structural Biology, 19:596-604 (2009). (Year: 2009).*
Yunus et al. Primary fibromyalgia. American family physician, Abstract. vol. 25, No. 5, pp. 115-121; (May 1982). (Year: 1982).*
Solitar. Fibromyalgia: knowns, unknowns, and current treatment. Absract. Bulletin of the NYU hospital for joint diseases, vol. 68, No. 3, (2010). (Year: 2010).*
Jahan et al. Fibromyalgia syndrome: an overview of pathophysiology, diagnosis and management .Abstract. Oman medical journal, vol. 27, No. 3, pp. 192-195, (May 2012). (Year: 2012).*
Salman et al. Pregabalin versus amitriptyline in the treatment of fibromyalgia in Iraqi patients. Rheumatology United Kingdom, vol. 54, Supp. Supplement 1, pp. i95. Abstract No. 112. (Apr. 28, 2015-Apr. 30, 2015). (Year: 2015).*

(Continued)

*Primary Examiner* — Elizabeth C. Kemmerer
*Assistant Examiner* — Regina M DeBerry
(74) *Attorney, Agent, or Firm* — McCarter & English, LLP; Jill Mello; Yelena Margolin

(57) ABSTRACT

The present invention provides methods for treating a stiffened joint in a subject that comprise administering relaxin, e.g., a PEGylated relaxin-2, to the subject. The relaxin may be administered intra-articularly as a sustained release formulation. The present invention also provides sustained release formulations in the form of a hydrogel for administering polypeptides that are covalently attached to a polymer, e.g., PEG.

24 Claims, 14 Drawing Sheets
Specification includes a Sequence Listing.

(56) References Cited

OTHER PUBLICATIONS

Unemori et al. Human Relaxin Decreases Collagen Accumulation In Vivo in Two Rodent Models of Fibrosis. Journal of Invest Dermatol vol. 101:280-285, (1993). (Year: 1993).*
Baldwin et al., In situ crosslinkable heparin-containing poly(ethylene glycol) hydrogels for sustained anticoagulant release. J Biomed Mater Res A. Aug. 2012;100(8):2106-18.
Bennett, Relaxin and its role in the development and treatment of fibrosis. Transl Res. Jul. 2009;154(1):1-6.
Ghobril et al., The chemistry and engineering of polymeric hydrogel adhesives for wound closure: a tutorial. Chem Soc Rev. Apr. 7, 2015;44(7):1820-35.
Kang et al., Down-regulation of collagen synthesis and matrix metalloproteinase expression in myofibroblasts from Dupuytren nodule using adenovirus-mediated relaxin gene therapy. J Orthop Res. Apr. 2014;32(4):515-23.
Kim et al., Relaxin Receptor RXFP1 and RXFP2 Expression in Ligament, Tendon, and Shoulder Joint Capsule of Rats. J Korean Med Sci. Jun. 2016;31(6):983-8.
Ross et al., Effects of molecular weight and loading on matrix metalloproteinase-2 mediated release from poly(ethylene glycol) diacrylate hydrogels. AAPS J. Sep. 2012;14(3):482-90.
Turturro et al., MMP-sensitive PEG diacrylate hydrogels with spatial variations in matrix properties stimulate directional vascular sprout formation. PLoS One. 2013;8(3):e58897, 14 pages.
Wolf et al., Relationship of relaxin hormone and thumb carpometacarpal joint arthritis. Clin Orthop Relat Res. Apr. 2014,472(4):1130-7.
International Search Report and Written Opinion for Application No. PCT/US2017/055799, dated Mar. 23, 2018, 21 pages.

\* cited by examiner
† cited by third party

A) Relaxin—(NH$_2$)$_3$

B) Albumin—(NH$_2$)$_{40}$

C) Crosslinker with different PEG MW n = 46 (2000 MW), 1a
n = 78 (3400 MW), 1b
n = 114 (5000 MW), 1c

D) Crosslinker with different number of methylene spacer n = 46 (2000 MW)

m = 2, Succinic acid (C$_4$), 1a
m = 6, Suberic acid acid (C$_8$), 1d
m = 10, Dodecanedioic acid (C$_{12}$), 1e

E) Crosslinker with amide linkage (as a controll crosslinker)

n = 46 (2000 MW), 1f

Crosslinker 1 (SCM functional group)   Crosslinker 1' (SVA functional group)

X = O, n = 46 (2000 MW), m = 2 (C4)   X = O, n = 46 (2000 MW), m = 6 (C8)
X = O, n = 78 (3400 MW), m = 2 (C4)   X = O, n = 46 (2000 MW), m = 10 (C12)
X = O, n = 114 (5000 MW), m = 2 (C4)   X = NH, n = 46 (2000 MW), m = 2 (C4)

SEQUENCE LISTING

<160> NUMBER OF SEQ ID NOS: 18

<210> SEQ ID NO 1
<211> LENGTH: 185
<212> TYPE: PRT
<213> ORGANISM: Homo sapiens

<400> SEQUENCE: 1

Met Pro Arg Leu Phe Phe Phe His Leu Leu Gly Val Cys Leu Leu Leu
1               5                   10                  15

Asn Gln Phe Ser Arg Ala Val Ala Asp Ser Trp Met Glu Glu Val Ile
            20                  25                  30

Lys Leu Cys Gly Arg Glu Leu Val Arg Ala Gln Ile Ala Ile Cys Gly
        35                  40                  45

-continued

```
Met Ser Thr Trp Ser Lys Arg Ser Leu Ser Gln Glu Asp Ala Pro Gln
            50                  55                  60

Thr Pro Arg Pro Val Ala Glu Ile Val Pro Ser Phe Ile Asn Lys Asp
 65                  70                  75                  80

Thr Glu Thr Ile Asn Met Met Ser Glu Phe Val Ala Asn Leu Pro Gln
                 85                  90                  95

Glu Leu Lys Leu Thr Leu Ser Glu Met Gln Pro Ala Leu Pro Gln Leu
            100                 105                 110

Gln Gln His Val Pro Val Leu Lys Asp Ser Ser Leu Leu Phe Glu Glu
            115                 120                 125

Phe Lys Lys Leu Ile Arg Asn Arg Gln Ser Glu Ala Ala Asp Ser Ser
130                 135                 140

Pro Ser Glu Leu Lys Tyr Leu Gly Leu Asp Thr His Ser Arg Lys Lys
145                 150                 155                 160

Arg Gln Leu Tyr Ser Ala Leu Ala Asn Lys Cys Cys His Val Gly Cys
                165                 170                 175

Thr Lys Arg Ser Leu Ala Arg Phe Cys
            180                 185
```

<210> SEQ ID NO 2
<211> LENGTH: 185
<212> TYPE: PRT
<213> ORGANISM: Homo sapiens

<400> SEQUENCE: 2

```
Met Pro Arg Leu Phe Phe Phe His Leu Leu Gly Val Cys Leu Leu Leu
 1               5                  10                  15

Asn Gln Phe Ser Arg Ala Val Ala Asp Ser Trp Met Glu Glu Val Ile
                20                  25                  30

Lys Leu Cys Gly Arg Glu Leu Val Arg Ala Gln Ile Ala Ile Cys Gly
            35                  40                  45

Met Ser Thr Trp Ser Lys Arg Ser Leu Ser Gln Glu Asp Ala Pro Gln
            50                  55                  60

Thr Pro Arg Pro Val Ala Glu Ile Val Pro Ser Phe Ile Asn Lys Asp
 65                  70                  75                  80

Thr Glu Thr Ile Asn Met Met Ser Glu Phe Val Ala Asn Leu Pro Gln
                 85                  90                  95

Glu Leu Lys Leu Thr Leu Ser Glu Met Gln Pro Ala Leu Pro Gln Leu
            100                 105                 110

Gln Gln His Val Pro Val Leu Lys Asp Ser Ser Leu Leu Phe Glu Glu
            115                 120                 125

Phe Lys Lys Leu Ile Arg Asn Arg Gln Ser Glu Ala Ala Asp Ser Ser
130                 135                 140

Pro Ser Glu Leu Lys Tyr Leu Gly Leu Asp Thr His Ser Arg Lys Lys
145                 150                 155                 160

Arg Gln Leu Tyr Ser Ala Leu Ala Asn Lys Cys Cys His Val Gly Cys
                165                 170                 175

Thr Lys Arg Ser Leu Ala Arg Phe Cys
            180                 185
```

<210> SEQ ID NO 3
<211> LENGTH: 185
<212> TYPE: PRT
<213> ORGANISM: Artificial Sequence
<220> FEATURE:
<223> OTHER INFORMATION: Synthetic construct

<400> SEQUENCE: 3

```
Met Pro Arg Leu Phe Phe Phe His Leu Leu Gly Val Cys Leu Leu Leu
1               5                   10                  15

Asn Gln Phe Ser Arg Ala Val Ala Asp Ser Trp Met Glu Glu Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Thr Glu Thr Ile Asn Met Met Ser Glu Phe Val Ala Asn Leu Pro Gln
                85                  90                  95

Glu Leu Lys Leu Thr Leu Ser Glu Met Gln Pro Ala Leu Pro Gln Leu
            100                 105                 110

Gln Gln His Val Pro Val Leu Lys Asp Ser Ser Leu Leu Phe Glu Glu
        115                 120                 125

Phe Lys Lys Leu Ile Arg Asn Arg Gln Ser Glu Ala Ala Asp Ser Ser
130                 135                 140

Pro Ser Glu Leu Lys Tyr Leu Gly Leu Asp Thr His Ser Arg Lys Lys
145                 150                 155                 160

Arg Gln Leu Tyr Ser Ala Leu Ala Asn Lys Cys Cys His Val Gly Cys
                165                 170                 175

Thr Lys Arg Ser Leu Ala Arg Phe Cys
            180                 185
```

<210> SEQ ID NO 4
<211> LENGTH: 185
<212> TYPE: PRT
<213> ORGANISM: Homo sapiens

<400> SEQUENCE: 4

```
Met Pro Arg Leu Phe Leu Phe His Leu Leu Glu Phe Cys Leu Leu Leu
1               5                   10                  15

Asn Gln Phe Ser Arg Ala Val Ala Ala Lys Trp Lys Asp Asp Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Thr Glu Thr Ile Ile Ile Met Leu Glu Phe Ile Ala Asn Leu Pro Pro
                85                  90                  95

Glu Leu Lys Ala Ala Leu Ser Glu Arg Gln Pro Ser Leu Pro Glu Leu
            100                 105                 110

Gln Gln Tyr Val Pro Ala Leu Lys Asp Ser Asn Leu Ser Phe Glu Glu
        115                 120                 125

Phe Lys Lys Leu Ile Arg Asn Arg Gln Ser Glu Ala Ala Asp Ser Asn
130                 135                 140

Pro Ser Glu Leu Lys Tyr Leu Gly Leu Asp Thr His Ser Gln Lys Lys
145                 150                 155                 160

Arg Arg Pro Tyr Val Ala Leu Phe Glu Lys Cys Cys Leu Ile Gly Cys
                165                 170                 175
```

```
Thr Lys Arg Ser Leu Ala Lys Tyr Cys
        180                 185

<210> SEQ ID NO 5
<211> LENGTH: 185
<212> TYPE: PRT
<213> ORGANISM: Homo sapiens

<400> SEQUENCE: 5

Met Pro Arg Leu Phe Leu Phe His Leu Leu Glu Phe Cys Leu Leu Leu
1               5                   10                  15

Asn Gln Phe Ser Arg Ala Val Ala Ala Lys Trp Lys Asp Asp Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Thr Glu Thr Ile Ile Ile Met Leu Glu Phe Ile Ala Asn Leu Pro Pro
                85                  90                  95

Glu Leu Lys Ala Ala Leu Ser Glu Arg Gln Pro Ser Leu Pro Glu Leu
            100                 105                 110

Gln Gln Tyr Val Pro Ala Leu Lys Asp Ser Asn Leu Ser Phe Glu Glu
        115                 120                 125

Phe Lys Lys Leu Ile Arg Asn Arg Gln Ser Glu Ala Ala Asp Ser Asn
    130                 135                 140

Pro Ser Glu Leu Lys Tyr Leu Gly Leu Asp Thr His Ser Gln Lys Lys
145                 150                 155                 160

Arg Arg Pro Tyr Val Ala Leu Phe Glu Lys Cys Cys Leu Ile Gly Cys
                165                 170                 175

Thr Lys Arg Ser Leu Ala Lys Tyr Cys
        180                 185

<210> SEQ ID NO 6
<211> LENGTH: 92
<212> TYPE: PRT
<213> ORGANISM: Homo sapiens

<400> SEQUENCE: 6

Met Pro Arg Leu Phe Leu Phe His Leu Leu Glu Phe Cys Leu Leu Leu
1               5                   10                  15

Asn Gln Phe Ser Arg Ala Val Ala Ala Lys Trp Lys Asp Asp Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Gly Ile Ser Ser Ser Leu Leu Arg Arg Arg
65                  70                  75                  80

Leu Phe Glu Asp His Asp Gly Pro Ser Phe Leu Val
                85                  90

<210> SEQ ID NO 7
<211> LENGTH: 99
<212> TYPE: PRT
<213> ORGANISM: Homo sapiens
```

```
<400> SEQUENCE: 7

Met Leu Glu Phe Ile Ala Asn Leu Pro Pro Glu Leu Lys Ala Ala Leu
1               5                   10                  15

Ser Glu Arg Gln Pro Ser Leu Pro Glu Leu Gln Gln Tyr Val Pro Ala
            20                  25                  30

Leu Lys Asp Ser Asn Leu Ser Phe Glu Glu Phe Lys Lys Leu Ile Arg
        35                  40                  45

Asn Arg Gln Ser Glu Ala Ala Asp Ser Asn Pro Ser Glu Leu Lys Tyr
50                  55                  60

Leu Gly Leu Asp Thr His Ser Gln Lys Lys Arg Arg Pro Tyr Val Ala
65                  70                  75                  80

Leu Phe Glu Lys Cys Cys Leu Ile Gly Cys Thr Lys Arg Ser Leu Ala
                85                  90                  95

Lys Tyr Cys

<210> SEQ ID NO 8
<211> LENGTH: 142
<212> TYPE: PRT
<213> ORGANISM: Homo sapiens

<400> SEQUENCE: 8

Met Ala Arg Tyr Met Leu Leu Leu Leu Ala Val Trp Val Leu Thr
1               5                   10                  15

Gly Glu Leu Trp Pro Gly Ala Glu Ala Arg Ala Ala Pro Tyr Gly Val
            20                  25                  30

Arg Leu Cys Gly Arg Glu Phe Ile Arg Ala Val Ile Phe Thr Cys Gly
        35                  40                  45

Gly Ser Arg Trp Arg Arg Ser Asp Ile Leu Ala His Glu Ala Met Gly
    50                  55                  60

Asp Thr Phe Pro Asp Ala Asp Ala Asp Glu Asp Ser Leu Ala Gly Glu
65                  70                  75                  80

Leu Asp Glu Ala Met Gly Ser Ser Glu Trp Leu Ala Leu Thr Lys Ser
                85                  90                  95

Pro Gln Ala Phe Tyr Arg Gly Arg Pro Ser Trp Gln Gly Thr Pro Gly
            100                 105                 110

Val Leu Arg Gly Ser Arg Asp Val Leu Ala Gly Leu Ser Ser Ser Cys
        115                 120                 125

Cys Lys Trp Gly Cys Ser Lys Ser Glu Ile Ser Ser Leu Cys
    130                 135                 140

<210> SEQ ID NO 9
<211> LENGTH: 142
<212> TYPE: PRT
<213> ORGANISM: Homo sapiens

<400> SEQUENCE: 9

Met Ala Arg Tyr Met Leu Leu Leu Leu Ala Val Trp Val Leu Thr
1               5                   10                  15

Gly Glu Leu Trp Pro Gly Ala Glu Ala Arg Ala Ala Pro Tyr Gly Val
            20                  25                  30

Arg Leu Cys Gly Arg Glu Phe Ile Arg Ala Val Ile Phe Thr Cys Gly
        35                  40                  45

Gly Ser Arg Trp Arg Arg Ser Asp Ile Leu Ala His Glu Ala Met Gly
    50                  55                  60

Asp Thr Phe Pro Asp Ala Asp Ala Asp Glu Asp Ser Leu Ala Gly Glu
```

```
                65                  70                  75                  80
Leu Asp Glu Ala Met Gly Ser Ser Glu Trp Leu Ala Leu Thr Lys Ser
                    85                  90                  95

Pro Gln Ala Phe Tyr Arg Gly Arg Pro Ser Trp Gln Gly Thr Pro Val
                100                 105                 110

Val Leu Arg Gly Ser Arg Asp Val Leu Ala Gly Leu Ser Ser Ser Cys
                115                 120                 125

Cys Lys Trp Gly Cys Ser Lys Ser Glu Ile Ser Ser Leu Cys
            130                 135                 140

<210> SEQ ID NO 10
<211> LENGTH: 142
<212> TYPE: PRT
<213> ORGANISM: Homo sapiens

<400> SEQUENCE: 10

Met Ala Arg Tyr Met Leu Leu Leu Leu Ala Val Trp Val Leu Thr
1               5                   10                  15

Gly Glu Leu Trp Pro Gly Ala Glu Ala Arg Ala Pro Tyr Gly Val
                20                  25                  30

Arg Leu Cys Gly Arg Glu Phe Ile Arg Ala Val Ile Phe Thr Cys Gly
                35                  40                  45

Gly Ser Arg Trp Arg Arg Ser Asp Ile Leu Ala His Glu Ala Met Gly
            50                  55                  60

Asp Thr Phe Pro Asp Ala Asp Ala Glu Asp Ser Leu Ala Gly Glu
65                  70                  75                  80

Leu Asp Glu Ala Met Gly Ser Ser Glu Trp Leu Ala Leu Thr Lys Ser
                    85                  90                  95

Pro Gln Ala Phe Tyr Arg Gly Arg Pro Ser Trp Gln Gly Thr Pro Gly
                100                 105                 110

Val Leu Arg Gly Ser Arg Asp Val Leu Ala Gly Leu Ser Ser Ser Cys
                115                 120                 125

Cys Lys Trp Gly Cys Ser Lys Ser Glu Ile Ser Ser Leu Cys
            130                 135                 140

<210> SEQ ID NO 11
<211> LENGTH: 131
<212> TYPE: PRT
<213> ORGANISM: Homo sapiens

<400> SEQUENCE: 11

Met Asp Pro Arg Leu Pro Ala Trp Ala Leu Val Leu Leu Gly Pro Ala
1               5                   10                  15

Leu Val Phe Ala Leu Gly Pro Ala Pro Thr Pro Glu Met Arg Glu Lys
                20                  25                  30

Leu Cys Gly His His Phe Val Arg Ala Leu Val Arg Val Cys Gly Gly
                35                  40                  45

Pro Arg Trp Ser Thr Glu Ala Arg Pro Ala Thr Gly Gly Asp Arg
            50                  55                  60

Glu Leu Leu Gln Trp Leu Glu Arg Arg His Leu Leu His Gly Leu Val
65                  70                  75                  80

Ala Asp Ser Asn Leu Thr Leu Gly Pro Gly Leu Gln Pro Leu Pro Gln
                    85                  90                  95

Thr Ser His His His Arg His His Arg Ala Ala Thr Asn Pro Ala
                100                 105                 110

Arg Tyr Cys Cys Leu Ser Gly Cys Thr Gln Gln Asp Leu Leu Thr Leu
```

Cys Pro Tyr
    130

<210> SEQ ID NO 12
<211> LENGTH: 139
<212> TYPE: PRT
<213> ORGANISM: Homo sapiens

<400> SEQUENCE: 12

Met Ala Ser Leu Phe Arg Ser Tyr Leu Pro Ala Ile Trp Leu Leu Leu
1               5                   10                  15

Ser Gln Leu Leu Arg Glu Ser Leu Ala Ala Glu Leu Arg Gly Cys Gly
            20                  25                  30

Pro Arg Phe Gly Lys His Leu Leu Ser Tyr Cys Pro Met Pro Glu Lys
        35                  40                  45

Thr Phe Thr Thr Thr Pro Gly Gly Trp Leu Leu Glu Ser Gly Arg Pro
    50                  55                  60

Lys Glu Met Val Ser Thr Ser Asn Asn Lys Asp Gly Gln Ala Leu Gly
65                  70                  75                  80

Thr Thr Ser Glu Phe Ile Pro Asn Leu Ser Pro Glu Leu Lys Lys Pro
                85                  90                  95

Leu Ser Glu Gly Gln Pro Ser Leu Lys Lys Ile Ile Leu Ser Arg Lys
            100                 105                 110

Lys Arg Ser Gly Arg His Arg Phe Asp Pro Phe Cys Cys Glu Val Ile
        115                 120                 125

Cys Asp Asp Gly Thr Ser Val Lys Leu Cys Thr
    130                 135

<210> SEQ ID NO 13
<211> LENGTH: 139
<212> TYPE: PRT
<213> ORGANISM: Homo sapiens

<400> SEQUENCE: 13

Met Ala Ser Leu Phe Arg Ser Tyr Leu Pro Ala Ile Trp Leu Leu Leu
1               5                   10                  15

Ser Gln Leu Leu Arg Glu Ser Leu Ala Ala Glu Leu Arg Gly Cys Gly
            20                  25                  30

Pro Arg Phe Gly Lys His Leu Leu Ser Tyr Cys Pro Met Pro Glu Lys
        35                  40                  45

Thr Phe Thr Thr Thr Pro Gly Gly Trp Leu Leu Glu Ser Gly Arg Pro
    50                  55                  60

Lys Glu Met Val Ser Thr Ser Asn Asn Lys Asp Gly Gln Ala Leu Gly
65                  70                  75                  80

Thr Thr Ser Glu Phe Ile Pro Asn Leu Ser Pro Glu Leu Lys Lys Pro
                85                  90                  95

Leu Ser Glu Gly Gln Pro Ser Leu Lys Lys Ile Ile Leu Ser Arg Lys
            100                 105                 110

Lys Arg Ser Gly Arg His Arg Phe Asp Pro Phe Cys Cys Glu Val Ile
        115                 120                 125

Cys Asp Asp Gly Thr Ser Val Lys Leu Cys Thr
    130                 135

<210> SEQ ID NO 14
<211> LENGTH: 135
<212> TYPE: PRT

<213> ORGANISM: Homo sapiens

<400> SEQUENCE: 14

Met Lys Gly Ser Ile Phe Thr Leu Phe Leu Phe Ser Val Leu Phe Ala
1               5                   10                  15

Ile Ser Glu Val Arg Ser Lys Glu Ser Val Arg Leu Cys Gly Leu Glu
            20                  25                  30

Tyr Ile Arg Thr Val Ile Tyr Ile Cys Ala Ser Ser Arg Trp Arg Arg
        35                  40                  45

His Leu Glu Gly Ile Pro Gln Ala Gln Gln Ala Glu Thr Gly Asn Ser
    50                  55                  60

Phe Gln Leu Pro His Lys Arg Glu Phe Ser Glu Asn Pro Ala Gln
65                  70                  75                  80

Asn Leu Pro Lys Val Asp Ala Ser Gly Glu Asp Arg Leu Trp Gly Gly
                85                  90                  95

Gln Met Pro Thr Glu Glu Leu Trp Lys Ser Lys Lys His Ser Val Met
            100                 105                 110

Ser Arg Gln Asp Leu Gln Thr Leu Cys Cys Thr Asp Gly Cys Ser Met
        115                 120                 125

Thr Asp Leu Ser Ala Leu Cys
    130                 135

<210> SEQ ID NO 15
<211> LENGTH: 135
<212> TYPE: PRT
<213> ORGANISM: Homo sapiens

<400> SEQUENCE: 15

Met Lys Gly Ser Ile Phe Thr Leu Phe Leu Phe Ser Val Leu Phe Ala
1               5                   10                  15

Ile Ser Glu Val Arg Ser Lys Glu Ser Val Arg Leu Cys Gly Leu Glu
            20                  25                  30

Tyr Ile Arg Thr Val Ile Tyr Ile Cys Ala Ser Ser Arg Trp Arg Arg
        35                  40                  45

His Leu Glu Gly Ile Pro Gln Ala Gln Gln Ala Glu Thr Gly Asn Ser
    50                  55                  60

Phe Gln Leu Pro His Lys Arg Glu Phe Ser Glu Glu Asn Pro Ala Gln
65                  70                  75                  80

Asn Leu Pro Lys Val Asp Ala Ser Gly Glu Asp Arg Leu Trp Gly Gly
                85                  90                  95

Gln Met Pro Thr Glu Glu Leu Trp Lys Ser Lys Lys His Ser Val Met
            100                 105                 110

Ser Arg Gln Asp Leu Gln Thr Leu Cys Cys Thr Asp Gly Cys Ser Met
        115                 120                 125

Thr Asp Leu Ser Ala Leu Cys
    130                 135

<210> SEQ ID NO 16
<211> LENGTH: 213
<212> TYPE: PRT
<213> ORGANISM: Homo sapiens

<400> SEQUENCE: 16

Met Pro Arg Leu Leu Arg Leu Ser Leu Leu Trp Leu Gly Leu Leu Leu
1               5                   10                  15

Val Arg Phe Ser Arg Glu Leu Ser Asp Ile Ser Ser Ala Arg Lys Leu
            20                  25                  30

```
Cys Gly Arg Tyr Leu Val Lys Glu Ile Glu Lys Leu Cys Gly His Ala
        35                  40                  45

Asn Trp Ser Gln Phe Arg Phe Glu Glu Glu Thr Pro Phe Ser Arg Leu
    50                  55                  60

Ile Ala Gln Ala Ser Glu Lys Val Glu Ala Tyr Ser Pro Tyr Gln Phe
65                  70                  75                  80

Glu Ser Pro Gln Thr Ala Ser Pro Ala Arg Gly Arg Gly Thr Asn Pro
                85                  90                  95

Val Ser Thr Ser Trp Glu Glu Ala Val Asn Ser Trp Glu Met Gln Ser
                100                 105                 110

Leu Pro Glu Tyr Lys Asp Lys Lys Gly Tyr Ser Pro Leu Gly Lys Thr
            115                 120                 125

Arg Glu Phe Ser Ser Ser His Asn Ile Asn Val Tyr Ile His Glu Asn
            130                 135                 140

Ala Phe Phe Gln Lys Lys Arg Arg Asn Lys Ile Lys Thr Leu Ser Asn
145                 150                 155                 160

Leu Phe Trp Gly His His Pro Gln Arg Lys Arg Arg Gly Tyr Ser Glu
                165                 170                 175

Lys Cys Cys Leu Thr Gly Cys Thr Lys Glu Glu Leu Ser Ile Ala Cys
            180                 185                 190

Leu Pro Tyr Ile Asp Phe Lys Arg Leu Lys Glu Lys Arg Ser Ser Leu
            195                 200                 205

Val Thr Lys Ile Tyr
        210

<210> SEQ ID NO 17
<211> LENGTH: 5
<212> TYPE: PRT
<213> ORGANISM: Artificial Sequence
<220> FEATURE:
<223> OTHER INFORMATION: Synthetic construct

<400> SEQUENCE: 17

Ala Ala Ala Ala Ala
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic construct

<400> SEQUENCE: 18

Glu Ser Leu Ala Tyr Tyr Thr Ala
1               5
```

COMPOSITIONS COMPRISING RELAXIN AND METHODS OF USE THEREOF

RELATED APPLICATIONS

This application is a 35 U.S.C. § 371 national stage filing of International Application No. PCT/US2017/055799, filed on Oct. 9, 2017, which claims priority to U.S. Provisional Application No. 62/405,795, filed on Oct. 7, 2016. The entire contents of each of the aforementioned applications are hereby incorporated herein by reference.

BACKGROUND OF THE INVENTION

Joint stiffness is a significant public health issue with current treatment options providing varied and limited outcomes. Joint stiffness can affect any joint in the body, such as a shoulder joint, an elbow joint, a wrist joint, a finger joint, a hip joint, a knee joint and an ankle joint. A shoulder joint is often affected by joint stiffness, which is also termed a shoulder contracture, and is also known as "frozen shoulder".

Shoulder contracture affects approximately 2% of the U.S. population, or approximately six million individuals. While women are more often affected than men, there is no known genetic or racial predilection (Robinson C. M. et al., *J. Bone Joint Surg. Br.* 2012, 94(1):1-9; Ewald A., *Am. Fam. Physician* 2011, 83(4):417-22). Shoulder contracture recovery is arduous and protracted with a significant number of patients never regaining full joint function. The condition affects both quality of life and productivity. Its predominant feature is painful, gradual loss of both active and passive glenohumeral motion resulting from progressive fibrosis of the glenohumeral joint capsule. The contracted capsule causes pain, especially when it is stretched suddenly, and produces a mechanical restraint to motion. The disease course of primary (idiopathic) shoulder contracture begins with the slow onset (over 2 to 9 months) of pain and stiffness that progressively restricts both passive and active range of motion (ROM) in the glenohumeral joint (Sharma S., *Annals of the Royal College of Surgeons of England* 2011 93(5): 343-4; discussion 5-6). The pain may sharpen at night, leaving patients unable to sleep on the affected side. Subsequently, the pain generally abates over a period of 4 to 12 months, but stiffness severely restricts ROM, particularly in the external rotational plane. There is a slow improvement in ROM over a period of 2 to 4 years. Secondary shoulder contracture has a similar presentation and progression but results from a known intrinsic or extrinsic cause (Sheridan M. A. and Hannafin J. A., *Orthop. Clin. North Am.* 2006, 37(4):531-9). Secondary shoulder contracture following trauma or surgery has a 100% incidence to varying degrees after these events and requires prolonged physical therapy, with original motion not always restored.

Shoulder contracture pathology is a thickened glenohumeral joint capsule with adhesions obliterating the axillary fold. The fibrotic capsule adheres to itself and the anatomic neck of the humerus, intra-articular volume is diminished, and synovial fluid in the joint is significantly decreased (Hand G. C. et al., *J. Bone Joint Surg. Br.* 2007, 89(7):928-32). Biopsy of the capsule shows a chronic inflammatory infiltrate, an absence of synovial lining, and subsynovial fibrosis (Ozaki J. et al., *J. Bone Joint Surg. Am.* 1989, 71(10):1511-5; Wiley A. M., *Arthroscopy* 1991, 7(2): 138-43; Rodeo S. A. et al., *J. Orthop. Res.* 1997, 15(3):427-36). Patient biopsy samples confirm the presence of T-cells, B-cells, synovial cells, fibroblasts and transforming myofibroblasts, along with type-I and type-III collagen (Rodeo S. A. et al., *J. Orthop. Res.* 1997, 15(3):427-36; Bunker T. D. et al., *J. Bone Joint Surg. Br.* 2000, 82(5):768-73). Gene and protein expression assays have found products related to fibrosis, inflammation, and chondrogenesis (Hagiwara Y. et al., *Osteoarthritis Cartilage* 2012, 20(3):241-9), including increased COL1A1 and COL1A3, interleukin-6, platelet-derived growth factor (PDGF), fibroblast growth factors (FGF) and inhibitors of the matrix metalloproteinases (TIMPs), as well as decreased activity of matrix metalloproteinases (MMPs). These data indicate that inflammatory changes initiate the recruitment of fibroblasts and immune cells, precipitating the fibrotic process and inappropriate deposition of collagen. Alternatively, fibrotic changes may occur first, followed by inflammation. In this case fibrosis may result from an underlying disease process, in which cell signaling pathways governing collagen remodeling may be defective (Bunker T. D. et al., *J. Bone Joint Surg. Br.* 2000, 82(5):768-73). For example, patients treated with marimastat, a synthetic TIMP, developed shoulder contractures, and when the marimastat was stopped, the disease regressed (Hutchinson J. W. et al., *J. Bone Joint Surg. Br.* 1998, 80(5):907-8).

Shoulder contracture is considered a self-limiting disease, but recovery is protracted and arduous, with a significant number of patients never regaining full ROM. The reported outcomes of conservative therapy (i.e., physical therapy) vary considerably and are highly dependent on how they are measured (Neviaser A. S. and Neviaser R. J., *J. Am. Acad. Orthop. Surg.* 2011, 19(9):536-42). Results tend to be more favorable with subjective outcome measures than with objective outcome measures. In one study, 90% of patients treated with minimal therapy reported satisfaction with their shoulder function (Griggs S. M. et al., *J. Bone Joint Surg. Am.* 2000, 82-A(10): 1398-407). However, another that used objective outcomes reported residual pain in 50% of patients and motion deficit in 60% (Shaffer B et al., *J. Bone Joint Surg. Am.* 1992; 74(5):738-46). Mild to moderate symptoms can persist after 4.4 years following symptom onset of shoulder contracture. For those experiencing severe disease, such functional impairment interferes with daily activities and work-related responsibilities (Hand C. et al., *Journal of Shoulder and Elbow Surgery* 2008, 17(2):231-6). When patients do not respond to conservative management, other treatment options are available. Operative intervention in the form of manipulation under anesthesia may restore motion and decrease pain, but it has been associated with complications such as fracture, tendon rupture, and neurologic injury (Castellarin G. et al., *Archives of Physical Medicine and Rehabilitation* 2004, 85(8):1236-40; Hsu S. Y. and Chan K. M., *International Orthopaedics,* 1991, 15(2):79-83; Parker R. D. et al., *Orthopedics,* 1989, 12(7):989-90). There are reports that manipulation or capsular release do not offer reliable and consistent results. (Shaffer B et al., *J. Bone Joint Surg. Am.* 1992, 74(5):738-46; Ryans I. et al., *Rheumatology*

2005, 44(4):529-35). Accordingly, a more effective and consistent therapy for joint stiffness is needed.

SUMMARY OF THE INVENTION

The inventors of the present application have discovered that relaxin, e.g., a polypeptide belonging to the relaxin family, such as relaxin-2, or a relaxin analog, e.g., a polypeptide that binds to a relaxin receptor, is surprisingly effective at treating a stiffened joint, e.g., a stiffened shoulder joint. The inventors have also discovered that a polypeptide therapeutic or a diagnostic agent covalently attached to a polymer, e.g., PEGylated relaxin, may be administered to a subject using a sustained release formulation, in which the polypeptide therapeutic or diagnostic agent is covalently attached to a polymer, forming a hydrogel.

Accordingly, in one embodiment, the present invention provides a method for treating a stiffened joint in a subject in need thereof, the method comprising administering to the subject an effective amount of relaxin or an analog, a fragment or a variant thereof, such that the stiffened joint in the subject is treated.

In some embodiments, the relaxin is relaxin-2. In some embodiments, the relaxin comprises an amino acid sequence having at least 70%, at least 75%, at least 80%, at least 85%, at least 90%, at least 95% or at least 99% sequence identity with any of SEQ ID NOS: 1-16. In further embodiments, the relaxin comprises a polypeptide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 and SEQ ID NO: 16.

In some aspects, the relaxin or the analog, fragment or variant thereof has been recombinantly produced.

In some embodiments, the relaxin is administered locally, e.g., administered into the joint by an intraarticular injection.

In some aspects, the relaxin is administered via a needle selected from the group consisting of a 30 G needle, a 29 G needle, a 28 G needle, a 27 G needle, a 26 sG needle, a 26 G needle, a 25.5 G needle, a 25 sG needle, a 25 G needle, a 24.5 G needle, a 24 G needle, a 23.5 G needle, a 23 sG needle, a 23 G needle, a 22.5 G needle, a 22 sG needle, a 22 G needle, a 21.5 G needle, a 21 G needle, a 20.5 G needle, a 20 G needle, a 19.5 G needle, a 19 G needle, a 18.5 G needle and an 18 G needle. In one aspect, the relaxin is administered via a 21 G needle.

In some embodiments, the stiffened joint is selected from the group consisting of a shoulder joint, an elbow joint, a wrist joint, a finger joint, a hip joint, a knee joint, or an ankle joint. In one embodiment, the stiffened joint is a shoulder joint.

In some embodiments, the stiffened joint results from an injury, a medical procedure, an inflammation of the joint, or a prolonged immobility.

In some aspects, the relaxin is administered during a medical procedure, e.g., during surgery. In one embodiment, the relaxin is in a pellet form and is administered through a cannula or an incision. In another embodiment, the relaxin is administered during an outpatient fluorosciopic or ultrasound guided procedure.

In some embodiments, the relaxin is administered transcutaneously, e.g., using iontophoresis or electrophoresis. In one aspect, the relaxin is administered as a gel, a cream, an ointment, a lotion, a drop, a suppository, a spray, a liquid or a powder composition.

In some embodiments, the relaxin is administered as a part of a sustained-release formulation. In some embodiments, the sustained-release formulation is a hydrogel further comprising at least one polymer. In further embodiments, the at least one polymer is selected from the group consisting of polyethylene glycol (PEG), alginate, agarose, poly(ethylene glycol dimethacrylate), polylactic acid, polyglycolic acid, PLGA, gelatin, collagen, agarose, pectin, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly(uronic acid), poly(anhydride) and poly(vinylpyrrolidone). In one aspect, the polymer is PEG.

In some embodiments, the PEG is covalently attached to the relaxin. In some embodiments, the hydrogel is formed in situ following mixing of the relaxin and a cross-linker, wherein the cross-linker comprises:

a polypeptide reactive moiety covalently attached to PEG and a linker as illustrated by the following schematic:

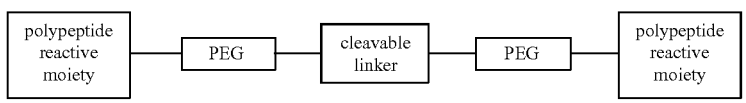

wherein the polypeptide reactive moiety comprises at least one amine- or a thiol-reactive group, and the linker comprises a moiety cleavable via a chemical or an enzymatic reaction.

In some aspects, the polypeptide reactive moiety comprises an amine reactive group, e.g., selected from the group consisting of N-hydroxysuccinimide (NHS), sulfanated NHS, an aldehyde, a ketone, an acrylate and an epoxide.

In some embodiments, the linker comprises a moiety cleavable via hydrolysis. In further embodiments, the moiety cleavable via hydrolysis has the following structural formula:

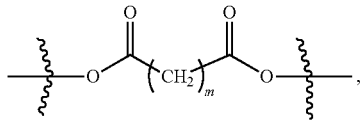

wherein m is any number from 1 to 10.

In some aspects, the cross-linker has the following structural formula:

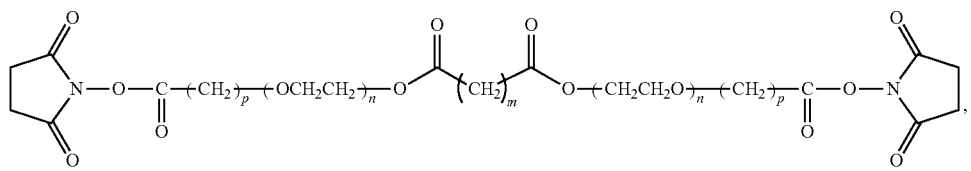

wherein n is 20-500; m is any number from 1 to 10; and p is any number from 1 to 6.

In some embodiments, n is 46, m is 2 and p is 1; n is 78, m is 2 and p is 1; n is 114, m is 2 and p is 1; n is 46, m is 6 and p is 1; n is 46, m is 10 and p is 1; n is 46, m is 2 and p is 4; n is 78, m is 2 and p is 4; n is 114, m is 2 and p is 4; n is 46, m is 6 and p is 4; or n is 46, m is 10 and p is 4.

In some aspects, the hydrogel is formed in situ after about 30 seconds, after about 25 seconds, after about 20 seconds, after about 15 seconds, or after about 10 seconds following mixing of the relaxin and the cross-linker. In some aspects, the mixing of the relaxin and the cross-linker takes place in a mixing chamber in a syringe further comprising two barrels. In some embodiments, the mixing of the relaxin and the cross-linker is carried out at a ratio of about 10:1, about 4:1, about 2:1 or about 1:1 relaxin:cross-linker.

In some embodiments, the hydrogel additionally comprises a filler polypeptide covalently attached to the PEG. In some embodiments, the hydrogel is formed in situ following mixing of the relaxin, the cross-linker and the filler polypeptide. In one aspect, the filler polypeptide is albumin.

In some aspects, the mixing of the relaxin, the cross-linker and albumin is carried out at a ratio of about 10:1, about 4:1, about 2:1 or about 1:1 relaxin and albumin:cross-linker. In some embodiments, the mixing of the relaxin, the cross-linker and albumin is carried out at a ratio of 5:95, 10:90, 50:50, 75:25, 90:10 and 95:5 albumin:relaxin. In some embodiments, total polymer weight of the hydrogel is about 0.1% to about 50%.

In some aspects, the sustained-release formulation provides release of a therapeutic dose of the relaxin covalently attached to PEG (PEGylated relaxin) during a period of at least about 1 week, at least about 2 weeks, at least about 3 weeks, at least about 4 weeks, at least about 5 weeks, at least about 6 weeks, at least about 8 weeks, at least about 9 weeks or at least about 10 weeks. In one embodiment, the sustained-release formulation provides release of a therapeutic dose of the PEGylated relaxin during a period of at least about 8 weeks.

In some embodiments, the formulation comprises between about 0.0005 to about 4000 ng of relaxin. In some embodiments, the relaxin is administered once or twice during the course of treatment.

In another embodiment, the present invention further provides a sustained release formulation for delivering a polypeptide therapeutic or diagnostic agent covalently attached to a polymer, wherein the formulation is a hydrogel comprising a polypeptide therapeutic or diagnostic agent covalently attached to a cross-linker comprising a polymer and a cleavable linker; and wherein the formulation releases the polypeptide therapeutic or diagnostic agent covalently attached to the polymer after the cleavable linker is cleaved chemically or enzymatically.

In some aspects, the polymer protects the polypeptide therapeutic or diagnostic agent from enzymatic degradation after it is released from the formulation. In some aspects, the hydrogel is formed in situ following mixing of the polypeptide therapeutic or diagnostic agent and the cross-linker.

In some embodiments, the cross-linker comprises a polypeptide reactive moiety covalently attached to the polymer and the cleavable linker as illustrated by the following schematic:

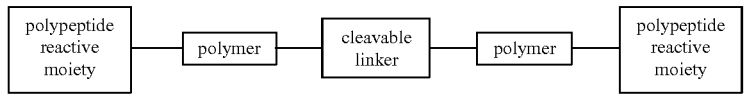

wherein the polypeptide reactive moiety comprises an amine- or a thiol-reactive group; and the cleavable linker comprises a moiety cleavable via a chemical or an enzymatic reaction.

In one embodiment, the polypeptide reactive moiety comprises an amine reactive group. In a further embodiment, the amine reactive group comprises a chemical group selected from the group consisting of: an isothiocyanate, an isocyanate, an acyl azide, an N-hydroxysuccinimide (NHS), a sulfonyl chloride, an aldehyde, a glyoxal, an epoxide, an oxirane, a carbonate, an aryl halide, an imidoester, a carbodiimide, an anhydride and a fluorophenyl ester. In a specific embodiment, the amine reactive moiety comprises NHS.

In some embodiments, the polymer is PEG. In some aspects, the PEG is represented by the following structural formula:

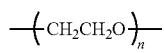

wherein n is 20-500.

In some embodiments, the cleavable linker is a polypeptide comprising an enzymatic cleavage site. In a further embodiment, the enzymatic cleavage site comprises a cleavage site selected from the group consisting of a collagenase cleavage site, a plasmin cleavage site, an elastase cleavage site and a metalloproteinase-2 cleavage site. In another further embodiment, the cleavable linker comprises a moiety cleavable via hydrolysis. In one embodiment, the moiety cleavable via hydrolysis has the following structural formula:

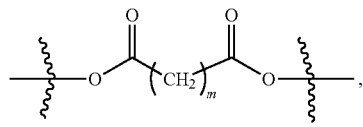

wherein m is any number from 1 to 10.

In some embodiments, the cross-linker has the following structural formula:

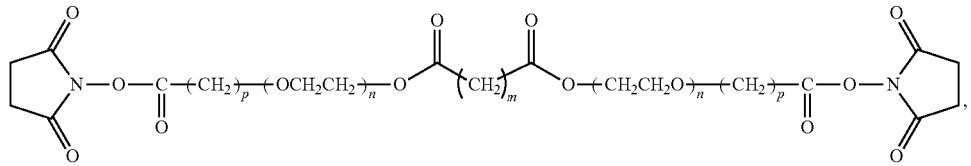

wherein n is 20-500; m is any number from 1 to 10; and p is any number from 1 to 6.

In another embodiment, n is 46, m is 2 and p is 1; n is 78, m is 2 and p is 1; n is 114, m is 2 and p is 1; n is 46, m is 6 and p is 1; n is 46, m is 10 and p is 1; n is 46, m is 2 and p is 4; n is 78, m is 2 and p is 4; n is 114, m is 2 and p is 4; n is 46, m is 6 and p is 4; or n is 46, m is 10 and p is 4.

In some aspects, the hydrogel is formed in situ after about 30 seconds, after about 25 seconds, after about 20 seconds, after about 15 seconds, or after about 10 seconds following mixing of the polypeptide therapeutic or diagnostic agent and the cross-linker. In some embodiments, the mixing of the polypeptide therapeutic or diagnostic agent and the cross-linker takes place in a mixing chamber in a syringe further comprising two barrels.

In some embodiments, the polypeptide therapeutic or diagnostic agent is relaxin or an analog, a fragment or a variant thereof.

In some aspects, the present invention also provides a syringe suitable for delivering the sustained release formulation of the invention to a subject in need thereof, comprising a first barrel comprising the polypeptide therapeutic or diagnostic agent; and a second barrel comprising the cross-linker comprising a polymer; and a mixing chamber for mixing the polypeptide therapeutic or diagnostic agent and the cross-linker comprising a polymer immediately prior to delivery.

In some embodiments, the first barrel additionally comprises a filler polypeptide, e.g., albumin. In one embodiment, the polymer is PEG. In another embodiment, the polypeptide therapeutic or diagnostic agent is relaxin or an analog, a fragment or a variant thereof. In another embodiment, the syringe is suitable for an intraarticular injection. In yet another embodiment, the syringe comprises a 21 G needle.

BRIEF DESCRIPTION OF THE DRAWINGS

FIG. 2, Panel B is a graph illustrating total active range of motion (ROM) in a shoulder contracture model in rats over time. Results are presented as means with standard error.

DETAILED DESCRIPTION OF THE INVENTION

Methods for Treating a Stiffened Joint

Figure 1:
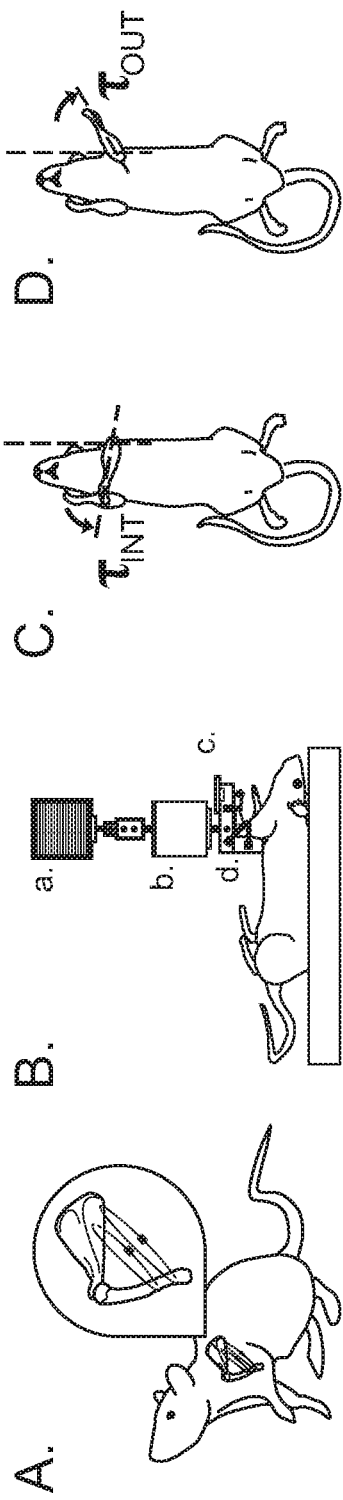
FIG. 1 is a schematic illustrating evaluation of a shoulder contracture model in rats. Panel A shows braided polyester sutures used to firmly tie the scapular edge to distal third of the humerus; panel B shows the forelimb attached to the arm clamp (d), while the stepper motor (a) provides the driving force for the ROM measurement; the sensor assembly consists of an orientation sensor (c) and a reaction torque sensor (b). Panel C shows internal rotation of the glenohumeral joint and Panel D shows external rotation of the glenohumeral joint that result from rotation of the sensor assembly.

The present invention provides methods for treating or preventing a stiffened joint in a subject in need thereof. The methods comprise administering to the subject an effective amount of relaxin or an analog, a fragment or a variant thereof, such that the stiffened joint in the subject is treated.

The currently available methods for treating a stiffened joint include physical therapy or surgical procedures, such as manipulations and releases, which do not offer reliable or consistent results (Diercks R. L. et al., *J. Shoulder Elbow Surg.* 2004, 13(5):499-502). The physical therapy involves prolonged manipulation by a physical therapist and the surgical procedures involve surgical releases by a surgeon, followed again by prolonged therapy.

The methods of the invention are advantageous as compared to the currently available methods because they can be used to reliably and effectively treat a stiffened joint while also using a minimally invasive procedure, e.g., an intra-articular injection, which may be performed in an outpatient setting or an office. Thus, the methods of the invention constitute a paradigm change in the management of a stiffened joint, e.g., a shoulder joint, that may result from, e.g., fibrosis. The methods of the invention involve minimally invasive procedures, e.g., an intra-articular injection of relaxin, e.g., relaxin-2 comprised in a sustained release formulation. The intra-articular injection may be repeated as needed until the stiffened joint is successfully treated, e.g., until motion in the joint is restored and pain during motion is eliminated. Successful treatment of a stiffened joint when using methods of the invention may be accomplished significantly faster and more effectively than when using the currently available methods.

The term "stiffened joint" refers to a joint that may be characterized by a loss of motion, loss of a range of motion or pain during movement. The term "stiffened joint" also refers to a joint characterized by fibrosis that is capsular in nature, i.e., fibrosis involving the capsule of the joint. A stiffened joint may be caused by a disease or a medical condition, such as osteoarthritis or inflammation of the joint. A stiffened joint may alternatively be caused by an injury to the joint. A stiffened joint may also result from a medical procedure, e.g., an operation, or from a prolonged immobility of the joint. The term "stiffened joint" includes any joint in a subject, e.g., a human subject, and may include, without limitation, a shoulder joint, an elbow joint, a finger joint, a hip joint, a knee joint or an ankle joint. In a specific embodiment, the stiffened joint is a shoulder joint. The term "stiffened joint" may also be referred to herein as "arthrofibrosis", "capsular fibrosis", or "fibrosis associated with capsular contracture", "adhesive capsulitis" or "frozen joint". The term "stiffened joint" also includes an ankylosed joint, i.e., a stiffened joint with a bony component to the stiffness, such as a fused joint from trauma or inflammation.

Pathology of a stiffened joint, e.g., a shoulder joint, can include a thickened glenohumeral joint capsule. Often with adhesions obliterating the axillary fold. Frequently, the fibrotic capsule adheres to itself and the anatomic neck of the humerus, intra-articular volume is diminished, and/or synovial fluid in the joint is significantly decreased. Biopsy of the capsule shows a chronic inflammatory infiltrate, with the presence of fibroblasts and transforming myofibroblasts, along with type-I and type-III collagen. Gene and protein expression assays have found products related to fibrosis, inflammation, and chondrogenesis, including increased COL1A1 and COL1A3, interleukin-6, platelet-derived growth factor (PDGF), fibroblast growth factors (FGF) and TMPs, as well as decreased MMP activity. This evidence points to inflammatory changes initiating the recruitment of fibroblasts and immune cells, precipitating the fibrotic process and inappropriate deposition of excess collagen. Alternatively, it is also possible that fibrosis occurs first, followed by inflammation; fibrosis being secondary to defective cell-signaling pathways governing collagen remodeling.

In various embodiments of the invention, a stiffened joint involves a loss of range of motion in the joint of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or a complete loss of range of motion in the joint. In various embodiments of the invention, a stiffened joint involves a loss of range of motion in the joint of at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90 or more degrees.

Without wishing to be bound by a specific theory, it is believed that relaxin, when delivered to a joint, e.g., via a hydrogel-based, intraarticular, sustained release formulation, promotes collagen degradation, thereby altering the homeostatis of the extracellular matrix (ECM) in the synovium. This results in a decreased joint stiffness and an increased range of motion of the joint.

The methods of the invention comprise administering relaxin to a subject in need thereof. Relaxin is a 6-kDa protein belonging to the insulin superfamily (Sherwood O.D., *Endocr. Rev.* 2004, 25(2):205-34). Like insulin, relaxin is processed from a prepro-form to the mature hormone-containing A and B peptide chains, which are connected by 2 interchain disulfide bridges and 1 intrachain disulfide within the A chain (Chan L. J. et al., *Protein Pept. Lett.* 2011, 18(3):220-9). Relaxin readily decreases collagen secretion and increases collagen degradation by increasing the expression of MMPs and decreasing the expression of TIMPs (Samuel C. S. et al., *Cell Mol. Life Sci.* 2007, 64(12):1539-57). This hormone is involved in reproduction, where it inhibits uterine contraction and induces growth and softening of the cervix, and thus used to assist delivery (Parry L. J. et al., *Adv. Exp. Med. Biol.* 2007, 612:34-48). Recently, a highly purified recombinant form of H2 relaxin, or relaxin-2, has been tested in a number of in vitro and in vivo systems to evaluate both its ability to modify connective tissue and its potential antifibrotic properties. Several studies report that relaxin acts at multiple levels to inhibit fibrogenesis and collagen overexpression associated with fibrosis and is able to prevent and treat pulmonary, renal, cardiac, and hepatic fibrosis (Bennett R. G., *Transl. Res.* 2009, 154(1):1-6). Relaxin treatment of human fibroblasts caused a reduction in levels of collagen types I and III and fibronectin (Unemori E. N. et al., *The Journal of Clinical Investigation* 1996, 98(12):2739-45). In vivo, relaxin decreased bleomycin-induced collagen amounts in the lung and improved the overall amount of fibrosis (Unemori E. N. et al., *The Journal of Clinical Investigation* 1996, 98(12): 2739-45). In cultured renal fibroblasts, epithelial cells and mesangial cells, relaxin decreased TGF-β-induced fibronectin levels and increased fibronectin degradation (McDonald G. A. et al., *American Journal of Physiology Renal Physiology* 2003, 285(1):F59-67).

The term "relaxin or an analog, a fragment or a variant thereof" encompasses any member of the relaxin-like peptide family which belongs to the insulin superfamily. The relaxin-like peptide family includes relaxin-like (RLN) peptides, e.g., relaxin-1 (RLN1), relaxin-2 (RLN2) and relaxin-3 (RLN3), and the insulin-like (INSL) peptides, e.g., INSL3, INSL4, INSL5 and INSL6. Representative sequences of human RLN1 are listed herein as SEQ ID NOS: 4-7; representative sequences of human RLN2 are listed herein as SEQ ID NOS: 1-3; representative sequences of human RLN3 are listed herein as SEQ ID NOS: 8-10; a representative sequence of human INSL3 is listed herein as SEQ ID NO: 11; representative sequences of human INSL4 are listed herein as SEQ ID NOS: 12-13; representative sequences of human INSL5 are listed herein as SEQ ID NOS. 14-15; and a representative sequence of human INSL6 is listed herein as SEQ ID NO: 16. The term "relaxin or an analog, a fragment or a variant thereof" encompasses any polypeptide having at least 70%, e.g., at least 75%, at least 80%, at least 85%, at least 90%, at least 95%, 96%, 97%, 98% or at least 99% sequence identity with any of SEQ ID NOS: 1-16, as well as any polypeptide sequence that comprises any of SEQ ID NOS: 1-16. In one embodiment of the invention, the relaxin includes RLN1, RLN2 or RLN3. In one embodiment, the relaxin is relaxin-1. In another embodiment, the relaxin is relaxin-3. In a preferred embodiment, the relaxin is relaxin-2. In another embodiment of the invention, the relaxin includes INSL3, INSL4, INSL5 or INSL6. In one embodiment, the relaxin is INSL3. In one embodiment, the relaxin is INSL4. In one embodiment, the relaxin is INSL5. In one embodiment, the relaxin is INSL6.

The term "relaxin or an analog, a fragment or a variant thereof" also encompasses any mutant member of the relaxin-like peptide family. Such mutant may be, e.g., an RLN1, RLN2, RLN3, INSL3, INSL4, INSL5 or INSL6 comprising one or more mutations, e.g., substitutions, additions or deletions of one or more amino acids in the known sequence of RLN1, RLN2, RLN3, INSL3, INSL4, INSL5 or INSL6. For example, a mutant member of the relaxin-like peptide family may comprise any naturally occurring or artificially produced variants of RLN1, RLN2, RLN3, INSL3, INSL4, INSL5 or INSL6. A mutant member of the relaxin-like peptide family retains or possesses the biological activity of the relaxin, i.e., the ability to treat a stiffened joint.

The term "relaxin fragment" or "a fragment of relaxin" as used herein encompasses any fragment of relaxin, i.e., a partial sequence of any member of the relaxin-like peptide family, that retains its ability to treat stiffened joints.

The term "relaxin analog" an "analog of relaxin" includes any non-relaxin polypeptide sequence that possesses the biological activity of the relaxin, i.e., the ability to treat a stiffened joint. In one embodiment, such polypeptide sequence may comprise prolactin or an analog, a fragment or a variant thereof.

In some embodiments, the term "relaxin analog" also includes a relaxin receptor agonist, e.g., any agent, such as a small molecule, a polypeptide, a polynucleotide or a polysaccharide, that can bind to and activate a relaxin receptor, e.g., one or more of RXFP1, RXFP2, RXFP3 and RXFP4. For example, a relaxin receptor agonist may be a polypeptide comprising the receptor binding site of relaxin. A relaxin receptor agonist may also be a polypeptide comprising any other sequence capable of binding to and activating the relaxin receptor, e.g., RXFP1, RXFP2, RXFP3 and RXFP4. The ability of a relaxin receptor agonist to bind to and activate the relaxin receptor can be assessed using techniques commonly known in the art.

The term "relaxin or an analog, a fragment or a variant thereof" includes any recombinantly produced relaxin, such as, e.g., Serelaxin (RLX030) being developed by Novartis. Methods for producing recombinant relaxin, e.g., relaxin-2, are described, e.g., in U.S. Pat. No. 5,464,756, the entire contents of which are incorporated herein by reference. The recombinantly produced relaxin or analog, fragment or variant thereof may comprise a relaxin sequence, e.g., RLN1, RLN2, RLN3, INSL3, INSL4, INSL5 or INSL6, and a histidine (His) tag to aid in the purification of the relaxin after it was recombinantly produced.

The relaxin or analog, fragment or variant thereof may also comprise one or more chemical modifications, e.g., chemical groups covalently attached to the relaxin or an analog, a fragment or a variant thereof. Such chemical groups may include, e.g., carbohydrates or other polymers, e.g., polyethylene glycol (PEG). In one embodiment, the relaxin or an analog, a fragment or a variant thereof is a PEGylated relaxin, e.g., a PEGylated relaxin-2. In a preferred embodiment, the relaxin or an analog, a fragment or a variant thereof is a PEGylated relaxin-2. In another embodiment, the relaxin or an analog, a fragment or a variant thereof is a PEGylated relaxin-1. In one embodiment, the relaxin or an analog, a fragment or a variant thereof is a PEGylated relaxin-3. In one embodiment, the relaxin or an analog, a fragment or a variant thereof is a PEGylated INSL3. In one embodiment, the relaxin or an analog, a fragment or a variant thereof is a PEGylated INSL4. In one embodiment, the relaxin or an analog, a fragment or a variant thereof is a PEGylated INSL5. In one embodiment, the relaxin or an analog, a fragment or a variant thereof is a PEGylated INSL6. In some embodiments, the PEGylated relaxin is relaxin that is covalently attached to a linear or branched PEG macromolecule comprising from 10 to 2000 ethylene oxide ($-CH_2CH_2O-$) units, e.g., from 10 to 200 units, from 50 to 100 units, from 100 to 400 units, from 300 to 1000 units or from 500 to 2000 units. In specific embodiments, the PEGylated relaxin is a relaxin that is covalently attached to a linear molecule that comprises 46, 78 or 114 units.

In some embodiments, the term "relaxin or analog, fragment or variant thereof" does not include relaxin attached, e.g., covalently attached, to an immunoglobulin or a fragment of an immunoglobulin, e.g., an antibody or a fragment of an antibody. For example, in some embodiments, the term "relaxin or analog, fragment or variant thereof" does not include the relaxin immunoglobulin fusion proteins described in WO 2017/100540, the entire contents of which are incorporated by reference herein.

The present invention provides methods for treating or preventing a stiffened joint. As used herein, the terms "treating", "treat" or "treatment" refer to a beneficial or desired result including, but not limited to, alleviation or amelioration of one or more symptoms associated with a stiffened joint (e.g., pain on movement of the joint, loss of motion of the joint or loss of the range of motion of the joint); diminishing the restriction of movement resulting from a stiffened joint; stabilization (i.e., not worsening) of the joint stiffness; amelioration or palliation of the restriction of movement resulting from a stiffened joint (e.g., pain on movement of the joint, loss of motion of the joint or loss of the range of motion of the joint) whether detectable or undetectable.

In some embodiments, methods of the present invention result in a treatment of the stiffened joint, such that pain on movement of the joint is reduced, e.g., by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more, and is preferably down to a level accepted as being within the range of normal for an individual who is not affected by a stiffened joint.

In some embodiments, methods of the present invention result in restoration of the movement, or a range of the movement, of a joint affected by joint stiffness. For example, treatment of the stiffened joint according to the methods of the invention may result in restoration of the movement, or a range of movement, of a joint affected by joint stiffness, to levels that are at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or 100% of the levels accepted as being within the range of normal for an individual not affected by a stiffened joint.

In some embodiments, methods of the present invention result in improvement of the movement, or a range of the movement, of a joint affected by joint stiffness. For example, treatment of the stiffened joint according to the methods of the invention may result in improvement of the movement, or a range of movement, of a joint affected by joint stiffness, by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% over the level in the stiffened joint prior to treatment.

In some embodiments, methods of the present invention result in improvement of the degree of range of movement of a joint affected by joint stiffness. For example, treatment of the stiffened joint according to the methods of the invention may result in improvement of the degree of range of movement of a joint affected by joint stiffness by at least about 2 degrees, at least about 3 degrees, at least about 4 degrees, at least about 5 degrees, at least about 6 degrees, at least about 7 degrees, at least about 8 degrees, at least about 9 degrees, at least about 10 degrees, at least about 12 degrees, at least about 15 degrees, at least about 18 degrees, at least about 20 degrees, at least about 25 degrees, at least about 30 degrees, at least about 35 degrees, at least about 40 degrees, at least about 45 degrees, at least about 50 degrees, at least about 55 degrees, at least about 60 degrees, at least about 65 degrees, at least about 70 degrees, at least about 75 degrees, at least about 80 degrees, at least about 85 degrees, or at least about 90 degrees as compared to the level in the stiffened joint prior to treatment.

In some embodiments, prevention or treatment of stiffened joint in a subject provided by the methods of the present invention is accomplished without significant adverse events, without significant damage to collagenous structures or tissues in the subject, e.g., collagenous structures or tissues of the joint, such as articular cartilage of the joint. For example, methods of the present invention provide prevention and treatment of stiffened joint that do not disrupt architecture of the joint. Intraarticular damage, i.e., damage to collagenous structures in the body, e.g., collagenous structures of a joint, may be assessed by methods known in the art, e.g., by measuring in the synovial fluid levels of various markers, such as Cartilage Oligomeric Matrix Protein (COMP). The intra-articular damage may also be assessed using MRI with or without special contrast agents, such as dGEMERIC MRI; or by direct visualization, such as arthroscopic assessment with or without biopsy.

In some embodiments, when relaxin is administered intraarticularly, prevention or treatment of stiffened joint by the methods of the present invention is accomplished without significant adverse events associated with systemic administration of relaxin. Exemplary adverse events associated with systemic administration of relaxin include, but are not limited to a hyperlaxed joint. Presence of a hyperlaxed joint may be assessed, by a physical exam in a trial, or by an experimental set-up in an animal model as described, e.g., in Example 2 herein. In the context of the present invention, when the relaxin is administered intraarticularly, adverse events associated with systemic administration of relaxin are substantially avoided.

As used herein, "prevention" or "preventing," when used in reference to a stiffened joint, refers to a reduction in the likelihood that a subject, e.g., a human subject, will develop a symptom associated with such a stiffened joint, or a reduction in the frequency and/or duration of a symptom associated with a stiffened joint. The likelihood of developing a stiffened joint is reduced, for example, when a subject having one or more risk factors for a stiffened joint either fails to develop a stiffened joint or develops a stiffened joint with less severity relative to a population having the same risk factors and not receiving treatment as described herein.

The failure to develop a stiffened joint, or the reduction in the development of a symptom associated with stiffened joint (e.g., by at least about 10%, 20%, 30%, 40%, 50%, 60%, 70%, 80% or more), or the exhibition of delayed symptoms, e.g., delayed by days, weeks, months or years) is considered effective prevention.

As used herein, an "effective amount," is intended to include the amount of relaxin or an analog, a fragment or a variant thereof, that, when administered to a subject having a stiffened joint, is sufficient to effect treatment of the stiffened joint (e.g., by diminishing, ameliorating or maintaining the stiffened joint or one or more symptoms of the stiffened joint). The "effective amount" may vary depending on the sequence of the relaxin, how the relaxin is administered, the severity of the joint stiffness and the history, age, weight, family history, genetic makeup, the types of preceding or concomitant treatments, if any, and other individual characteristics of the subject to be treated.

The effective amount of relaxin may also be referred to as a "therapeutic dose of relaxin". The therapeutic dose of the relaxin administered to a subject in accordance with methods of the present invention is sufficient to result in a treatment of the stiffened joint, e.g., achieve reduction of pain on movement of the joint, e.g., by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more, and preferably to achieve reduction of pain on movement of the joint down to a level accepted as being within the range of normal for an individual who is not affected by a stiffened joint.

In some embodiments, the therapeutic dose of the relaxin administered to a subject in accordance with methods of the present invention is sufficient to achieve restoration of the movement, or a range of the movement, of a joint affected by joint stiffness. For example, the therapeutic dose of the relaxin released from the sustained release formulation is sufficient to achieve restoration of the movement, or a range of movement, of a joint affected by joint stiffness, to levels that are at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or 100% of the levels accepted as being within the range of normal for an individual not affected by a stiffened joint.

In some embodiments, the therapeutic dose of the relaxin administered to a subject in accordance with methods of the present invention is sufficient to achieve improvement in the movement, or a range of the movement, of a joint affected by joint stiffness. For example, the therapeutic dose of the relaxin administered to a subject is sufficient to achieve improvement in the range of movement of a joint affected by joint stiffness by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, as compared to the range of motion in the joint of the individual prior to treatment.

In some embodiments, the therapeutic dose of the relaxin administered to a subject in accordance with methods of the present invention is sufficient to achieve improvement in the range of the movement of a joint affected by joint stiffness by at least about 2 degrees, at least about 3 degrees, at least about 4 degrees, at least about 5 degrees, at least about 6 degrees, at least about 7 degrees, at least about 8 degrees, at least about 9 degrees, at least about 10 degrees, at least about 12 degrees, at least about 15 degrees, at least about 18 degrees, at least about 20 degrees, at least about 25 degrees, at least about 30 degrees, at least about 35 degrees, at least about 40 degrees, at least about 45 degrees, at least about 50 degrees, at least about 55 degrees, at least about 60 degrees, at least about 65 degrees, at least about 70 degrees, at least about 75 degrees, at least about 80 degrees, at least about 85 degrees, or at least about 90 degrees as compared to the level in the stiffened joint prior to treatment.

In some embodiments, the therapeutic dose of the relaxin administered to a subject in accordance with methods of the present invention results in a concentration of relaxin in the subject that does not exceed a peak concentration of relaxin that occurs naturally in the subject. In some embodiments, the peak concentration of relaxin is the peak concentration of relaxin that occurs naturally in a female subject during pregnancy. In some embodiments, the concentration of relaxin may be the concentration of relaxin in a joint of the subject, e.g., concentration of relaxin in the synovial fluid of the joint. In other embodiments, the concentration of relaxin may be the concentration of relaxin in the blood of the subject, e.g., serum or plasma. In some embodiments, the therapeutic dose of the relaxin results in a concentration of relaxin that does not exceed a peak concentration of relaxin in the blood, e.g., serum or plasma, observed in a pregnant female subject. In some embodiments, the therapeutic dose of the relaxin results in a concentration of relaxin that does not exceed a peak concentration of relaxin in the joint, e.g., in the synovial fluid of the joint, observed in a pregnant female subject.

In some embodiments, the peak concentration of relaxin in the blood, e.g., serum or plasma, of a pregnant female subject, is between about 0.6 ng/mL and about 1.5 ng/mL. For example, one study showed that serum levels of relaxin at birth for normal term were about 0.767 ng/mL relaxin, with highs of 0.792 ng/mL for pre-term births (Thorell et al., *BMC Pregnancy Childbirth*, 2015, 15:168). Another study demonstrated similar levels of serum relaxin of about 0.8-0.9 ng/mL (Petersen et al., *Acta Obstet Gynecol Scand.*, 1995, 74(4):251-6). Yet another study showed a normal term birth with serum relaxin levels at 0.92+/−0.08 ng/mL (Goldsmith et al., *Ann N Y Acad Sci.*, 2009, 1160:130-5). Studies showed that pre-term births were associated with higher levels of relaxin, with highs at about 1.02 to 1.79 ng/mL (Thorell et al., *BMC Pregnancy Childbirth*, 2015, 15:168; Goldsmith et al., *Ann N Y Acad Sci.*, 2009, 1160:130-5). Studies also showed that joint laxity increases during the third trimester (Marnach et al., *Obstet Gynecol.*, 2003, 101(2):331-5; Schauberger et al., *Am. J. Obstet. Gynecol.*, 1996, 174(2):667-71; Calguneri et al., *Ann. Rheum. Dis.*, 1982, 41(2):126-8), indicating that relaxin production during the third trimester should be ideal in generating joint laxity. Relaxin-2 (hRLX-2) was shown to decrease over time during pregnancy, to about 0.8-0.9 ng/mL (Petersen et al., *Acta Obstet Gynecol Scand.*, 1995, 74(4):251-6). This is most likely due to an increase in other hormones. Improvements of joint laxity were determined in some studies to be approximately 7 degrees within the first trimester, and 15 degrees by the second trimester (Marnach et al., *Obstet Gynecol.*, 2003, 101(2):331-5).

In some embodiments, the therapeutic dose of the relaxin administered to a subject in accordance with methods of the present invention provides a concentration of the relaxin in the blood of a subject, e.g., in the serum or plasma of a subject, that is within the range of about 0.0005 ng/mL to about 10 ng/mL, e.g., about 0.0005 ng/mL to about 0.001 ng/mL, about 0.0008 ng/mL to about 0.003 ng/mL, about 0.002 ng/mL to about 0.006 ng/mL, about 0.005 ng/mL to about 0.01 ng/mL, about 0.008 ng/mL to about 0.03 ng/mL, about 0.01 ng/mL to about 0.05 ng/mL, about 0.02 ng/mL to about 0.08 ng/mL, about 0.04 ng/mL to about 0.1 ng/mL, about 0.06 ng/mL to about 0.2 ng/mL, about 0.1 ng/mL to about 0.7 ng/mL, about 0.6 ng/mL to about 0.9 ng/mL, about 0.8 ng/mL to about 1.2 ng/mL, about 1.0 ng/mL to about 1.3 ng/mL, about 1.2 ng/mL to about 1.5 ng/mL, about 1.4 ng/mL to about 1.8 ng/mL, about 1.5 ng/mL to about 1.9 ng/mL, about 1.8 ng/mL to about 2.4 ng/mL, about 2.0 ng/mL to about 2.6 ng/mL, about 2.5 ng/mL to about 2.8 ng/mL, about 2.7 ng/mL to about 5.0 ng/mL, about 3.5 ng/mL to about 6.5 ng/mL, about 4.0 ng/mL to about 7 ng/mL, about 6.5 ng/mL to about 9 ng/mL, or about 7 ng/mL to about 10 ng/mL.

In some embodiments, the therapeutic dose of the relaxin administered to a subject in accordance with methods of the present invention provides a concentration of the relaxin in the blood of a subject, e.g., in the serum or plasma of a subject, that is about 0.0005 ng/mL, about 0.0006 ng/mL, about 0.0007 ng/mL, about 0.0008 ng/mL, about 0.0009 ng/mL, about 0.001 ng/mL, about 0.002 ng/mL, about 0.003 ng/mL, about 0.004 ng/mL, about 0.005 ng/mL, about 0.006 ng/mL, about 0.007 ng/mL, about 0.008 ng/mL, about 0.009 ng/mL, about 0.01 ng/mL, about 0.02 ng/mL, about 0.03 ng/mL, about 0.04 ng/mL, about 0.05 ng/mL, about 0.06 ng/mL, about 0.07 ng/mL, about 0.08 ng/mL, about 0.09 ng/mL, about 0.1 ng/mL, about 0.2 ng/mL, about 0.3 ng/mL, about 0.4 ng/mL, about 0.5 ng/mL, 0.6 ng/mL, about 0.7 ng/mL, about 0.8 ng/mL, about 0.9 ng/mL, about 1.0 ng/mL, about 1.1 ng/mL, about 1.2 ng/mL, about 1.3 ng/mL, about 1.4 ng/mL, about 1.5 ng/mL, about 1.6 ng/mL, about 1.7 ng/mL, about 1.8 ng/mL, about 1.9 ng/mL, about 2.0 ng/mL, about 2.1 ng/mL, about 2.2 ng/mL, about 2.3 ng/mL, about 2.4 ng/mL, about 2.5 ng/mL, about 2.6 ng/mL, about 2.7 ng/mL, about 2.8 ng/mL, about 2.9 ng/mL, about 3.0 ng/mL, about 3.5 ng/mL, about 4.0 ng/mL, about 4.5 ng/mL, about 5.0 ng/mL, about 5.5 ng/mL, about 6.0 ng/mL, about 6.5 ng/mL, about 7.0 ng/mL, about 7.5 ng/mL, about 8.0 ng/mL, about 8.5 ng/mL, about 9.0 ng/mL, about 9.5 ng/mL or about 10 ng/mL. In a specific embodiment, the therapeutic dose of the relaxin administered to a subject in accordance with methods of the present invention provides a concentration of the relaxin in the blood of a subject, e.g., in the serum or plasma of a subject, that does not exceed about 0.8 ng/mL.

In some embodiments, the therapeutic dose of the relaxin administered to a subject in accordance with methods of the present invention provides a concentration of the relaxin in the joint of a subject, e.g., in the synovial fluid of the joint of a subject, that is within the range of about 0.0005 ng/mL to about 10 ng/mL, e.g., about 0.0005 ng/mL to about 0.001 ng/mL, about 0.0008 ng/mL to about 0.003 ng/mL, about 0.002 ng/mL to about 0.006 ng/mL, about 0.005 ng/mL to about 0.01 ng/mL, about 0.008 ng/mL to about 0.03 ng/mL, about 0.01 ng/mL to about 0.05 ng/mL, about 0.02 ng/mL to about 0.08 ng/mL, about 0.04 ng/mL to about 0.1 ng/mL, about 0.06 ng/mL to about 0.2 ng/mL, about 0.1 ng/mL to about 0.7 ng/mL, about 0.6 ng/mL to about 0.9 ng/mL, about 0.8 ng/mL to about 1.2 ng/mL, about 1.0 ng/mL to about 1.3 ng/mL, about 1.2 ng/mL to about 1.5 ng/mL, about 1.4 ng/mL to about 1.8 ng/mL, about 1.5 ng/mL to about 1.9 ng/mL, about 1.8 ng/mL to about 2.4 ng/mL, about 2.0 ng/mL to about 2.6 ng/mL, about 2.5 ng/mL to about 2.8 ng/mL, about 2.7 ng/mL to about 5.0 ng/mL, about 3.5 ng/mL to about 6.5 ng/mL, about 4.0 ng/mL to about 7 ng/mL, about 6.5 ng/mL to about 9 ng/mL, or about 7 ng/mL to about 10 ng/mL.

In some embodiments, the therapeutic dose of the relaxin administered to a subject in accordance with methods of the present invention provides a concentration of the relaxin in the joint of a subject, e.g., in the synovial fluid of the joint of a subject, that is about 0.0005 ng/mL, about 0.0006 ng/mL, about 0.0007 ng/mL, about 0.0008 ng/mL, about 0.0009 ng/mL, about 0.001 ng/mL, about 0.002 ng/mL, about 0.003 ng/mL, about 0.004 ng/mL, about 0.005 ng/mL, about 0.006 ng/mL, about 0.007 ng/mL, about 0.008 ng/mL, about 0.009 ng/mL, about 0.01 ng/mL, about 0.02 ng/mL, about 0.03 ng/mL, about 0.04 ng/mL, about 0.05 ng/mL, about 0.06 ng/mL, about 0.07 ng/mL, about 0.08 ng/mL, about 0.09 ng/mL, about 0.1 ng/mL, about 0.2 ng/mL, about 0.3 ng/mL, about 0.4 ng/mL, about 0.5 ng/mL, 0.6 ng/mL, about 0.7 ng/mL, about 0.8 ng/mL, about 0.9 ng/mL, about 1.0 ng/mL, about 1.1 ng/mL, about 1.2 ng/mL, about 1.3 ng/mL, about 1.4 ng/mL, about 1.5 ng/mL, about 1.6 ng/mL, about 1.7 ng/mL, about 1.8 ng/mL, about 1.9 ng/mL, about 2.0 ng/mL, about 2.1 ng/mL, about 2.2 ng/mL, about 2.3 ng/mL, about 2.4 ng/mL, about 2.5 ng/mL, about 2.6 ng/mL, about 2.7 ng/mL, about 2.8 ng/mL, about 2.9 ng/mL, about 3.0 ng/mL, about 3.5 ng/mL, about 4.0 ng/mL, about 4.5 ng/mL, about 5.0 ng/mL, about 5.5 ng/mL, about 6.0 ng/mL, about 6.5 ng/mL, about 7.0 ng/mL, about 7.5 ng/mL, about 8.0 ng/mL, about 8.5 ng/mL, about 9.0 ng/mL, about 9.5 ng/mL or about 10 ng/mL. In a specific embodiment, the therapeutic dose of the relaxin comprised in the sustained release formulation of the invention provides a concentration of the relaxin in the joint of a subject, e.g., in the synovial fluid of the joint of a subject, that does not exceed about 0.8 ng/mL.

The therapeutic dose of the relaxin administered to a subject in accordance with methods of the present invention may also be adjusted based on the change in ROM that is desired, e.g., a larger desired recovery in ROM may require a greater therapeutic dose of the relaxin in a given timeframe; or an increased recovery time may require a greater therapeutic dose of the PEGylated relaxin for a given recovery in ROM. In one example, the therapeutic dose of the PEGylated relaxin is administered to a subject in accordance with methods of the present every 6 weeks and is about 3 ng/mL. This dosage may be further increased if ROM is not sufficiently recovered. The therapeutic dose of the relaxin may also be adjusted based on the type of joint being treated because different joints express different levels of the relaxin receptor (Kim et al., *J. Korean Med. Sci.*, 2016, 31(6):983-8).

The term "effective amount," as used herein, is also intended to include the amount of relaxin or an analog, a fragment or a variant thereof, that, when administered to a subject with a stiffened joint but not yet (or currently) experiencing or displaying symptoms of the stiffened joint, such as pain on movement or restriction of the movement or a range of movement of the joint affected by the joint stiffness, and/or a subject at risk of developing a stiffened joint, is sufficient to prevent or ameliorate the stiffened joint or one or more of its symptoms. Ameliorating the stiffened joint includes slowing the course of the progression of the joint stiffness or reducing the severity of later-developing joint stiffness.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for a stiffened joint; a human at risk for developing a stiffened joint; a human having a stiffened joint; and/or human being treated for a stiffened joint. In one embodiment, the subject is a human being treated or assessed for a stiffened joint. In one embodiment, the subject is a human at risk for developing a stiffened joint. In one embodiment, the subject is a human having a stiffened joint. In one embodiment, the subject is a human previously treated for a stiffened joint.

Methods of the invention comprise administering relaxin or an analog, a fragment or a variant thereof to a subject. The terms "administer", "administering" or "administration" include any method of delivery of relaxin into the subject's system or to a particular region in or on the subject. For example, relaxin may be administered intravenously, intramuscularly, subcutaneously, intradermally, intranasally, orally, transcutaneously, mucosally, or intra-articularly. Administering the relaxin can be performed by a number of people working in concert and can include, for example, prescribing the relaxin or an analog, a fragment or a variant thereof to be administered to a subject and/or providing instructions, directly or through another, to take the relaxin or an analog, a fragment or a variant thereof, either by self-delivery, e.g., as by oral delivery, subcutaneous delivery, intravenous delivery through a central line, etc.; or for delivery by a trained professional, e.g., intra-articular delivery, intravenous delivery, intramuscular delivery, intratumoral delivery, etc.

In a preferred embodiment, the relaxin or an analog, a fragment or a variant thereof is administered locally, e.g., directly to or into a joint of a subject. Local administration of the relaxin, e.g., by an intra-articular injection or by topical application to the joint, is advantageous because it allows delivering a smaller dose of the relaxin to the subject and because it avoids the side-effects associated with systemic delivery, such as back pain and joint pain.

In one embodiment, the relaxin is administered to the subject by an intra-articular injection. In one embodiment, the relaxin is administered to the subject via multiple intraarticular injections. The multiple intra-articular injections of relaxin may be administered to a subject at regularly spaced time intervals, e.g., every day, every 2 days, every 3 days, every 4 days, every 5 days, every 6 days, every 7 days, every 8 days, every 9 days, every 10 days, every 11 days, every 12 days every 13 days or every 14 days. A course of treatment consisting of multiple intraarticular injections of relaxin may be repeated.

In another embodiment, a sustained release formulation of the invention comprising relaxin, e.g., PEGylated relaxin, is administered to a subject by an intra-articular injection for preventing or treating stiffened joint.

The intra-articular injection of the relaxin may be accomplished by using a syringe with a needle suited for an intra-articular injection. A needle suitable for an intra-articular injection may be selected from the group consisting of a 30 G needle, a 29 G needle, a 28 G needle, a 27 G needle, a 26 sG needle, a 26 G needle, a 25.5 G needle, a 25 sG needle, a 25 G needle, a 24.5 G needle, a 24 G needle, a 23.5 G needle, a 23 sG needle, a 23 G needle, a 22.5 G needle, a 22 sG needle, a 22 G needle, a 21.5 G needle, a 21 G needle, a 20.5 G needle, a 20 G needle, a 19.5 G needle, a 19 G needle, a 18.5 G needle and an 18 G needle. In a specific embodiment, the relaxin is administered via a 21 G needle.

In another preferred embodiment, the relaxin may be administered to a subject topically, e.g., transcutaneously. For example the relaxin may be administered as a gel, a cream, an ointment, a lotion, a drop, a suppository, a spray, a liquid or a powder composition that is applied topically to a joint, e.g., a finger joint. The relaxin may also be administered transcutaneously using iontophoresis or electrophoresis, e.g., via a transdermal patch.

In some embodiments, the relaxin may be administered to a subject during a medical procedure, e.g., a surgery, to treat or prevent a stiffened joint. Because stiffened joint may result from a surgery, administering relaxin during surgery may prevent formation of a stiffened joint in a subject. In one embodiment, the relaxin may be administered through a cannula or an incision. In one embodiment, the relaxin may be in form of a pellet.

In another embodiment, the relaxin may be administered during an outpatient fluorosciopic or ultrasound guided procedure.

In a preferred embodiment, the relaxin is administered to the subject locally as a part of a sustained release formulation. Administering relaxin as a sustained release formulation is advantageous because it avoids repeated injections and can deliver a therapeutic dose of the relaxin in a consistent and reliable manner, and over a desired period of time. Exemplary sustained release formulations that may be used to delivery polypeptides, such as relaxin, e.g., relaxin-2, are described in Vaishya et al., *Expert. Opin. Drug Deliv.* 2015, 12(3):415-40, the entire contents of which are incorporated herein by reference.

A sustained release formulation comprising relaxin may be in the form of a hydrogel which comprises one or more polymers. The polymers that may be used in a sustained release relaxin formulation may include, without limitation, polyethylene glycol (PEG), alginate, agarose, poly(ethylene glycol dimethacrylate), polylactic acid, polyglycolic acid, PLGA, gelatin, collagen, agarose, pectin, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly (uronic acid), poly(anhydride) and poly(vinylpyrrolidone).

In certain embodiments of the invention, the sustained release hydrogel formulation of relaxin comprises PEG, e.g., a linear PEG or a branched PEG. In one embodiment the sustained release hydrogel formulation of relaxin comprises a linear PEG. In one embodiment the sustained release hydrogel formulation of relaxin comprises a branched PEG. In certain embodiments, the PEG is a 5 kDa PEG, 10 kDa PEG, or 20 kDa PEG. In one embodiment, the PEG is a 5 kDa PEG. In one embodiment, the PEG is a 10 kDa PEG. In one embodiment, the PEG is a 20 kDa PEG.

In some embodiments, the relaxin administered to a subject for treating a stiffened joint comprises one or more chemical modifications, e.g., a polymer covalently attached to the relaxin. In one embodiment, the polymer is PEG, and the chemically modified relaxin is a PEGylated relaxin, e.g., a PEGylated relaxin-1, PEGylated relaxin-2 or PEGylated relaxin-3. In one embodiment, the polymer is PEG, and the chemically modified relaxin is a PEGylated relaxin-1. In one embodiment, the polymer is PEG, and the chemically modified relaxin is a PEGylated relaxin-3. In a preferred embodiment, the polymer is PEG, and the chemically modified relaxin is a PEGylated relaxin-2. In other embodiments, the polymer is PEG, and the chemically modified relaxin is a PEGylated INSL3, INSL4, INSL5 or INSL6. In one embodiment, the polymer is PEG, and the chemically modified relaxin is a PEGylated INSL3. In one embodiment, the polymer is PEG, and the chemically modified relaxin is a PEGylated INSL4. In one embodiment, the polymer is PEG, and the chemically modified relaxin is a PEGylated INSL5. In one embodiment, the polymer is PEG, and the chemically modified relaxin is a PEGylated INSL6.

Administering PEGylated relaxin to a subject for treating a stiffened joint may offer several advantages as compared to administering a relaxin which does not contain any chemical modifications. A PEGylated relaxin may exhibit improved solubility, increased stability, enhanced resistance to proteolytic degradation, an extended in vivo half-life, or any combination thereof.

In a preferred embodiment, the PEGylated relaxin is administered via a sustained release formulation. Such sustained release formulation is capable of releasing PEGylated relaxin, e.g., PEGylated relaxin-2, in a consistent and reliable manner, over time. In one such sustained release formulation, the PEG is covalently attached to the relaxin and is in a form of a hydrogel.

The hydrogel acting as a sustained release formulation may be formed in situ following mixing of the relaxin and a cross-linker that comprises a polypeptide reactive moiety covalently attached to PEG and a cleavable linker as illustrated by the following schematic:

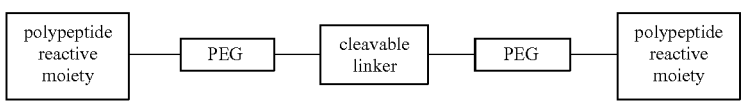

wherein the polypeptide reactive moiety comprises at least one amine- or a thiol-reactive group; and the linker comprises a moiety cleavable via a chemical or an enzymatic reaction. In order to produce cross-links between the relaxin and the cross-linker illustrated above, and thereby form a hydrogel, at least three free amines and/or thiols need to be present on the relaxin. PEGylated relaxin is released from the hydrogel following hydrolysis of the cleavable linker in vivo.

The polypeptide reactive moiety on the cross-linker is an amine- or a thiol-reactive group that reacts with a free amine group or a free thiol group on a polypeptide and becomes covalently attached to the polypeptide. In a specific embodiment, the polypeptide reactive moiety is an amine-reactive group, e.g., N-hydroxysuccinimide (NHS), sulfanated NHS, an aldehyde, a ketone, an acrylate or an epoxide.

The cleavable linker present in the cross-linker illustrated above may be cleavable by hydrolysis. In some embodiments, the cleavable linker may have the following structural formula:

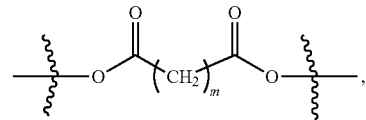

wherein m is any number from 1 to 10.

In a specific embodiment, the cross-linker may have the following structural formula:

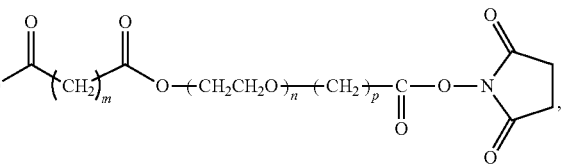

wherein n is 20-500, e.g., n is 20-500, e.g., 20-50, 30-90, 40-120, 100-150, 120-200, 180-250, 210-270, 250-310, 290-350, 330-400, 350-450 or 400-500; m is any number from 1 to 10, e.g., 1, 2, 3, 4, 5, 6, 7, 8 9 or 10; and p is any number from 1 to 6, e.g., 1, 2, 3, 4, 5 or 6. In one specific embodiment, m is 2. In another specific embodiment, m is 4. In another embodiment, n is 46, 78 or 114. In other specific embodiments, n is 46, m is 2 and p is 1;
n is 78, m is 2 and p is 1;
n is 114, m is 2 and p is 1;
n is 46, m is 6 and p is 1;
n is 46, m is 10 and p is 1;
n is 46, m is 2 and p is 4;
n is 78, m is 2 and p is 4;
n is 114, m is 2 and p is 4;
n is 46, m is 6 and p is 4; or
n is 46, m is 10 and p is 4.

To form the sustained release formulation for treating a stiffened joint, the relaxin and the cross-linker may be mixed together, and the hydrogel may form after about 30 seconds, after about 25 seconds, after about 20 seconds, after about 15 seconds, or after about 10 seconds following mixing of the relaxin and the cross-linker. In one embodiment, the hydrogel may be formed in situ. This may be accomplished with the use of a syringe comprising two barrels and a mixing chamber. A solution comprising the cross-linker is added to one barrel, a solution comprising relaxin is added to the second barrel, and the two solutions are mixed in the mixing chamber immediately prior to the administration.

The mixing of the relaxin and the cross-linker may be carried out at a ratio of relaxin:cross-linker ranging from about 1:1 to about 10:1, e.g., about 1:1 to about 3:1, about 2:1 to about 4:1, about 3:1 to about 5:1, about 4:1 to about 6:1, about 5:1 to about 7:1, about 6:1 to about 8:1, about 7:1 to about 9:1 or about 9:1 to about 10:1 relaxin:cross-linker. In some embodiments, the ratio of relaxin:cross-linker may be about 1:1, about 2:1, about 3:1, about 4:1, about 5:1, about 6:1, about 7:1, about 8:1, about 9:1 or about 10:1 of relaxin:cross-linker. In one embodiment, the ratio of relaxin: cross-linker may be about 10:1, about 4:1, about 2:1 or about 1:1 of the relaxin:cross-linker. The mixing may also be carried out in the presence of a filler polypeptide, e.g., albumin, such that the resulting hydrogel additionally comprises a filler polypeptide covalently attached to the PEG. The filler polypeptide, e.g., albumin, may be mixed with the relaxin and the cross-linker at a ratio of about 1:1 to about 10:1 of relaxin and albumin:cross-linker, e.g., about 1:1 to about 3:1, about 2:1 to about 4:1, about 3:1 to about 5:1, about 4:1 to about 6:1, about 5:1 to about 7:1, about 6:1 to about 8:1, about 7:1 to about 9:1 or about 9:1 to about 10:1 relaxin and albumin:cross-linker. In some embodiments, the ratio of relaxin and albumin:cross-linker may be about 1:1, about 2:1, about 3:1, about 4:1, about 5:1, about 6:1, about 7:1, about 8:1, about 9:1 or about 10:1 of relaxin and albumin:cross-linker. In one embodiment, the ratio of relaxin and albumin:cross-linker may be about 1:1, about 2:1, about 4:1 or about 10:1 In some embodiments, the mixing may also be carried out at the ratio of albumin: relaxin of about 5:95 to about 95:5, e.g., about 5:95 to about 50:70, about 10:90 to about 75:25, about 50:50 to about 95:5 of albumin:relaxin. For example, the mixing may be carried out at a ratio of albumin:relaxin of about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10 or about 95:5 of albumin: relaxin.

In some embodiments, the total polymer weight of the hydrogel may be between about 0.1% and about 50%, e.g, between about 1% and 50%, between about 10% and 50%, between about 25% and 50%, between about 0.1% and 25%, between about 0.1% and 10%, between about 0.1% and 1%, or between about 1% and 10%. In some embodiments, the total polymer weight of the hydrogel may be, e.g., about 0.5%, about 1%, about 5%, about 10%, about 15%, about 20%, about 25%, about 30%, about 35%, about 40%, about 45% or about 50%.

The sustained release formulation comprising relaxin may provide release of a therapeutic dose of the PEGylated relaxin during a period of at least about 1 week, at least about 2 weeks, at least about 3 weeks, at least about 4 weeks, at least about 5 weeks, at least about 6 weeks, at least about 8 weeks, at least about 9 weeks or at least about 10 weeks. In a specific embodiment, the sustained-release formulation comprising relaxin may provide release of a therapeutic dose of the PEGylated relaxin during a period of at least about 9 weeks.

In some embodiments, the therapeutic dose of the PEGylated relaxin released from the sustained release formulation of the present invention is sufficient to result in a treatment of the stiffened joint, e.g., achieve reduction of pain on movement of the joint, e.g., by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more, and preferably to achieve reduction of pain on movement of the joint down to a level accepted as being within the range of normal for an individual who is not affected by a stiffened joint.

In some embodiments, the therapeutic dose of the PEGylated relaxin released from the sustained release formulation of the present invention is sufficient to achieve restoration of the movement, or a range of the movement, of a joint affected by joint stiffness. For example, the therapeutic dose of the PEGylated relaxin released from the sustained release formulation is sufficient to achieve restoration of the movement, or a range of movement, of a joint affected by joint stiffness, to levels that are at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or 100% of the levels accepted as being within the range of normal for an individual not affected by a stiffened joint.

In some embodiments, the therapeutic dose of the PEGylated relaxin released from the sustained release formulation of the present invention is sufficient to achieve improvement in the movement, or a range of the movement, of a joint affected by joint stiffness. For example, the therapeutic dose of the PEGylated relaxin released from the sustained release formulation is sufficient to achieve improvement in the range of movement of a joint affected by joint stiffness, by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, as compared to the range of motion in the joint of the individual prior to treatment.

In some embodiments, the therapeutic dose of the PEGylated relaxin released from the sustained release formulation of the present invention is sufficient to achieve improvement in the range of the movement of a joint affected by joint stiffness by at least about 2 degrees, at least about 3 degrees, at least about 4 degrees, at least about 5 degrees, at least about 6 degrees, at least about 7 degrees, at least about 8 degrees, at least about 9 degrees, at least about 10 degrees, at least about 12 degrees, at least about 15 degrees, at least about 18 degrees, at least about 20 degrees, at least about 25 degrees, at least about 30 degrees, at least about 35 degrees, at least about 40 degrees, at least about 45 degrees, at least about 50 degrees, at least about 55 degrees, at least about 60 degrees, at least about 65 degrees, at least about 70 degrees, at least about 75 degrees, at least about 80 degrees, at least about 85 degrees, or at least about 90 degrees as compared to the level in the stiffened joint prior to treatment.

In some embodiments, the therapeutic dose of the PEGylated relaxin released from the sustained release formulation of the present invention results in a concentration of relaxin in the subject that does not exceed a peak concentration of relaxin that occurs naturally in the subject. In some embodiments, the peak concentration of relaxin is the peak concentration of relaxin that occurs naturally in a female subject during pregnancy. In some embodiments, the concentration of relaxin may be the concentration of relaxin in a joint of the subject, e.g., concentration of relaxin in the synovial fluid of the joint. In other embodiments, the concentration of relaxin may be the concentration of relaxin in the blood of the subject, e.g., serum or plasma. In some embodiments, the therapeutic dose of the PEGylated relaxin released from the sustained release formulation of the present invention results in a concentration of relaxin that does not exceed a peak concentration of relaxin in the blood, e.g., serum or plasma, observed in a pregnant female subject. In some embodiments, the therapeutic dose of the PEGylated relaxin released from the sustained release formulation of the present invention results in a concentration of relaxin that does not exceed a peak concentration of relaxin in the joint, e.g., in the synovial fluid of the joint, observed in a pregnant female subject.

In some embodiments, the peak concentration of relaxin in the blood, e.g., serum or plasma, of a pregnant female subject, is between about 0.6 ng/mL and about 1.5 ng/mL. For example, one study showed that serum levels of relaxin at birth for normal term were about 0.767 ng/mL relaxin, with highs of 0.792 ng/mL for pre-term births (Thorell et al., *BMC Pregnancy Childbirth,* 2015, 15:168). Another study demonstrated similar levels of serum relaxin of about 0.8-0.9 ng/mL (Petersen et al., *Acta Obstet Gynecol Scand.,* 1995, 74(4):251-6). Yet another study showed a normal term birth with serum relaxin levels at 0.92+/−0.08 ng/mL (Goldsmith et al., *Ann N Y Acad Sci.,* 2009, 1160:130-5). Studies showed that pre-term births were associated with higher levels of relaxin, with highs at about 1.02 to 1.79 ng/mL (Thorell et al., *BMC Pregnancy Childbirth,* 2015, 15:168; Goldsmith et al., *Ann N Y Acad Sci.,* 2009, 1160:130-5). Studies also showed that joint laxity increases during the third trimester (Marnach et al., *Obstet Gynecol.,* 2003, 101(2):331-5; Schauberger et al., *Am. J. Obstet. Gynecol.,* 1996, 174(2):667-71; Calguneri et al., *Ann. Rheum. Dis.,* 1982, 41(2):126-8), indicating that relaxin production during the third trimester should be ideal in generating joint laxity. Relaxin-2 (hRLX-2) was shown to decrease over time during pregnancy, to about 0.8-0.9 ng/mL (Petersen et al., *Acta Obstet Gynecol Scand.,* 1995, 74(4):251-6). This is most likely due to an increase in other hormones. Improvements of joint laxity were determined in some studies to be approximately 7 degrees within the first trimester, and 15 degrees by the second trimester (Marnach et al., *Obstet Gynecol.,* 2003, 101(2):331-5).

In some embodiments, the therapeutic dose of the PEGylated relaxin comprised in the sustained release formulation of the invention provides a concentration of the relaxin in the blood of a subject, e.g., in the serum or plasma of a subject, that is within the range of about 0.0005 ng/mL to about 10 ng/mL, e.g., about 0.0005 ng/mL to about 0.001 ng/mL, about 0.0008 ng/mL to about 0.003 ng/mL, about 0.002 ng/mL to about 0.006 ng/mL, about 0.005 ng/mL to about 0.01 ng/mL, about 0.008 ng/mL to about 0.03 ng/mL, about 0.01 ng/mL to about 0.05 ng/mL, about 0.02 ng/mL to about 0.08 ng/mL, about 0.04 ng/mL to about 0.1 ng/mL, about 0.06 ng/mL to about 0.2 ng/mL, about 0.1 ng/mL to about 0.7 ng/mL, about 0.6 ng/mL to about 0.9 ng/mL, about 0.8 ng/mL to about 1.2 ng/mL, about 1.0 ng/mL to about 1.3 ng/mL, about 1.2 ng/mL to about 1.5 ng/mL, about 1.4 ng/mL to about 1.8 ng/mL, about 1.5 ng/mL to about 1.9 ng/mL, about 1.8 ng/mL to about 2.4 ng/mL, about 2.0 ng/mL to about 2.6 ng/mL, about 2.5 ng/mL to about 2.8 ng/mL, about 2.7 ng/mL to about 5.0 ng/mL, about 3.5 ng/mL to about 6.5 ng/mL, about 4.0 ng/mL to about 7 ng/mL, about 6.5 ng/mL to about 9 ng/mL, or about 7 ng/mL to about 10 ng/mL.

In some embodiments, the therapeutic dose of the PEGylated relaxin comprised in the sustained release formulation of the invention provides a concentration of the relaxin in the blood of a subject, e.g., in the serum or plasma of a subject, that is about 0.0005 ng/mL, about 0.0006 ng/mL, about 0.0007 ng/mL, about 0.0008 ng/mL, about 0.0009 ng/mL, about 0.001 ng/mL, about 0.002 ng/mL, about 0.003 ng/mL, about 0.004 ng/mL, about 0.005 ng/mL, about 0.006 ng/mL, about 0.007 ng/mL, about 0.008 ng/mL, about 0.009 ng/mL, about 0.01 ng/mL, about 0.02 ng/mL, about 0.03 ng/mL, about 0.04 ng/mL, about 0.05 ng/mL, about 0.06 ng/mL, about 0.07 ng/mL, about 0.08 ng/mL, about 0.09 ng/mL, about 0.1 ng/mL, about 0.2 ng/mL, about 0.3 ng/mL, about 0.4 ng/mL, about 0.5 ng/mL, 0.6 ng/mL, about 0.7 ng/mL, about 0.8 ng/mL, about 0.9 ng/mL, about 1.0 ng/mL, about 1.1 ng/mL, about 1.2 ng/mL, about 1.3 ng/mL, about 1.4 ng/mL, about 1.5 ng/mL, about 1.6 ng/mL, about 1.7 ng/mL, about 1.8 ng/mL, about 1.9 ng/mL, about 2.0 ng/mL, about 2.1 ng/mL, about 2.2 ng/mL, about 2.3 ng/mL, about 2.4 ng/mL, about 2.5 ng/mL, about 2.6 ng/mL, about 2.7 ng/mL, about 2.8 ng/mL, about 2.9 ng/mL, about 3.0 ng/mL, about 3.5 ng/mL, about 4.0 ng/mL, about 4.5 ng/mL, about 5.0 ng/mL, about 5.5 ng/mL, about 6.0 ng/mL, about 6.5 ng/mL, about 7.0 ng/mL, about 7.5 ng/mL, about 8.0 ng/mL, about 8.5 ng/mL, about 9.0 ng/mL, about 9.5 ng/mL or about 10 ng/mL. In a specific embodiment, the therapeutic dose of the PEGylated relaxin comprised in the sustained release formulation of the invention provides a concentration of the relaxin in the blood of a subject, e.g., in the serum or plasma of a subject, that does not exceed about 0.8 ng/mL.

In some embodiments, the therapeutic dose of the PEGylated relaxin comprised in the sustained release formulation of the invention provides a concentration of the relaxin in the joint of a subject, e.g., in the synovial fluid of the joint of a subject, that is within the range of about 0.0005 ng/mL to about 10 ng/mL, e.g., about 0.0005 ng/mL to about 0.001 ng/mL, about 0.0008 ng/mL to about 0.003 ng/mL, about 0.002 ng/mL to about 0.006 ng/mL, about 0.005 ng/mL to about 0.01 ng/mL, about 0.008 ng/mL to about 0.03 ng/mL, about 0.01 ng/mL to about 0.05 ng/mL, about 0.02 ng/mL to about 0.08 ng/mL, about 0.04 ng/mL to about 0.1 ng/mL, about 0.06 ng/mL to about 0.2 ng/mL, about 0.1 ng/mL to about 0.7 ng/mL, about 0.6 ng/mL to about 0.9 ng/mL, about 0.8 ng/mL to about 1.2 ng/mL, about 1.0 ng/mL to about 1.3 ng/mL, about 1.2 ng/mL to about 1.5 ng/mL, about 1.4 ng/mL to about 1.8 ng/mL, about 1.5 ng/mL to about 1.9 ng/mL, about 1.8 ng/mL to about 2.4 ng/mL, about 2.0 ng/mL to about 2.6 ng/mL, about 2.5 ng/mL to about 2.8 ng/mL, about 2.7 ng/mL to about 5.0 ng/mL, about 3.5 ng/mL to about 6.5 ng/mL, about 4.0 ng/mL to about 7 ng/mL, about 6.5 ng/mL to about 9 ng/mL, or about 7 ng/mL to about 10 ng/mL.

In some embodiments, the therapeutic dose of the PEGylated relaxin comprised in the sustained release formulation of the invention provides a concentration of the relaxin in the joint of a subject, e.g., in the synovial fluid of the joint of a subject, that is about 0.0005 ng/mL, about 0.0006 ng/mL, about 0.0007 ng/mL, about 0.0008 ng/mL, about 0.0009 ng/mL, about 0.001 ng/mL, about 0.002 ng/mL, about 0.003 ng/mL, about 0.004 ng/mL, about 0.005 ng/mL, about 0.006 ng/mL, about 0.007 ng/mL, about 0.008 ng/mL, about 0.009 ng/mL, about 0.01 ng/mL, about 0.02 ng/mL, about 0.03 ng/mL, about 0.04 ng/mL, about 0.05 ng/mL, about 0.06 ng/mL, about 0.07 ng/mL, about 0.08 ng/mL, about 0.09 ng/mL, about 0.1 ng/mL, about 0.2 ng/mL, about 0.3 ng/mL, about 0.4 ng/mL, about 0.5 ng/mL, 0.6 ng/mL, about 0.7 ng/mL, about 0.8 ng/mL, about 0.9 ng/mL, about 1.0 ng/mL, about 1.1 ng/mL, about 1.2 ng/mL, about 1.3 ng/mL, about 1.4 ng/mL, about 1.5 ng/mL, about 1.6 ng/mL, about 1.7 ng/mL, about 1.8 ng/mL, about 1.9 ng/mL, about 2.0 ng/mL, about 2.1 ng/mL, about 2.2 ng/mL, about 2.3 ng/mL, about 2.4 ng/mL, about 2.5 ng/mL, about 2.6 ng/mL, about 2.7 ng/mL, about 2.8 ng/mL, about 2.9 ng/mL, about 3.0 ng/mL, about 3.5 ng/mL, about 4.0 ng/mL, about 4.5 ng/mL, about 5.0 ng/mL, about 5.5 ng/mL, about 6.0 ng/mL, about 6.5 ng/mL, about 7.0 ng/mL, about 7.5 ng/mL, about 8.0 ng/mL, about 8.5 ng/mL, about 9.0 ng/mL, about 9.5 ng/mL or about 10 ng/mL. In a specific embodiment, the therapeutic dose of the PEGylated relaxin comprised in the sustained release formulation of the invention provides a concentration of the relaxin in the joint of a subject, e.g., in the synovial fluid of the joint of a subject, that does not exceed about 0.8 ng/mL.

The therapeutic dose of the PEGylated relaxin comprised in the sustained release formulation of the present invention may also be adjusted based on the change in ROM that is desired, e.g., a larger desired recovery in ROM may require a greater therapeutic dose of the relaxin in a given timeframe; or an increased recovery time may require a greater therapeutic dose of the PEGylated relaxin for a given recovery in ROM. In one example, the therapeutic dose of the PEGylated relaxin comprised in the sustained release formulation of the invention is administered every 6 weeks and is about 3 ng/mL. This dosage may be further increased if ROM is not sufficiently recovered. The therapeutic dose of the PEGylated relaxin may also be adjusted based on the type of joint being treated because different joints express different levels of the relaxin receptor (Kim et al., *J. Korean Med. Sci.,* 2016, 31(6):983-8).

In some embodiments, the therapeutic dose of the PEGylated relaxin released from the sustained release formulation of the present invention does not result in substantial adverse events, e.g., adverse events associated with administering relaxin systemically, or adverse events associated with administering doses of relaxin that result in a concentration of relaxin in the synovial fluid exceeding the peak concentration of relaxin as described above.

The sustained release formulation may comprise a dose of relaxin that is between about 0.0005 to about 4000 ng, e.g., about 0.0005 to about 0.05 ng of relaxin, about 0.001 to about 0.1 ng of relaxin, about 0.01 to about 5 ng of relaxin, about 0.1 to about 10 ng of relaxin, about 1 to about 50 ng of relaxin, about 10 to about 100 ng of relaxin, about 50 to about 200 ng of relaxin, about 100 to about 500 ng of relaxin, about 200 ng to about 1000 ng of relaxin, about 500 to about 1500 ng of relaxin, about 1000 to about 2000 ng of relaxin or about 1500 to about 4000 ng of relaxin. In some embodiments, the sustained release formulation may comprise about 0.001 ng, about 0.005 ng, about 0.01 ng, about 0.05 ng, about 0.1 ng, about 0.5 ng, about 1 ng, about 5 ng, about 10 ng, about 50 ng, about 100 ng, about 500 ng, about 1000 ng or about 4000 ng of relaxin.

The relaxin may be administered once or multiple times during the course of the treatment. When relaxin is administered as a part of a sustained release formulation, only one, two, three, four, five, six, seven, eight, nine or more administrations of the sustained release formulation may be required during the course of the treatment.

The methods of the invention for treating a stiffened joint may be combined with other methods currently used to treat joint stiffness, e.g., surgery, physical therapy and/or treatment with anti-inflammatory agents that may be administered locally or systemically. In one embodiment, relaxin may be administered to a subject, e.g., a human, in combination with steroids.

Sustained Release Formulations of the Invention

The present invention also provides sustained release formulations for delivering a polypeptide therapeutic or diagnostic agent to a subject in need thereof. The sustained release formulations of the invention comprise a hydrogel that comprises a polypeptide therapeutic or diagnostic agent covalently attached to a cross-linker. The cross-linker may, in turn, comprise a polymer and a cleavable linker. The hydrogel may be formed in situ following mixing of the polypeptide therapeutic or diagnostic agent and the cross-linker. The polypeptide therapeutic or diagnostic agent covalently attached to the polymer is released from the hydrogel after the cleavable linker is cleaved chemically or enzymatically. Accordingly, the sustained release formulations of the invention are unique because they allow to simultaneously attach a polymer to a polypeptide and to deliver to a subject the polypeptide that is covalently attached to the polymer in a sustained release manner.

Administering a polypeptide therapeutic or diagnostic agent covalently attached to a polymer, e.g., a PEGylated polypeptide, may offer several advantages as compared to administering a polypeptide that is not covalently attached to a polymer. A polypeptide covalently attached to a polymer, e.g., a PEGylated polypeptide, may exhibit one or more of improved solubility, increased stability, enhanced resistance to proteolytic degradation and an extended in vivo half-life. Accordingly, a polymer useful in the sustained release formulations of the invention may be any polymer that, when covalently attached to a polypeptide, may confer any one or more of the following properties to the polypeptide: improved solubility, increased stability, enhanced resistance to proteolytic degradation and an extended in vivo half-life. In some embodiments, the polymer comprises PEG, e.g., a linear PEG or a branched PEG. In an embodiment, the PEG is a linear PEG. In certain embodiments, the PEG is a 5 kDa PEG, 10 kDa PEG, or 20 kDa PEG The term "polypeptide" encompasses amino acid sequences of at least 2 amino acids.

Thus, this term encompasses any amino acid sequence from a short peptide to a full length protein, to a protein complex comprising two or more amino acid sequences bound to each other via covalent bonds (e.g., disulfide bridges) or non-covalent interactions (e.g., hydrophobic, electrostatic or hydrogen bonding interactions).

The term "polypeptide therapeutic or diagnostic agent" includes any polypeptide that may be used therapeutically or diagnostically. Non-limiting examples of such polypeptides may include, e.g., a growth hormone, including human growth hormone and bovine growth hormone; a growth hormone releasing factor; a parathyroid hormone; a thyroid stimulating hormone; a lipoprotein; α-1 antitrypsin; insulin A-chain; insulin B-chain; proinsulin; follicle stimulating hormone; calcitonin; luteinizing hormone; glucagon; a clotting factor, such as factor VIIIC, tissue factor and von Willebrands factor; an anti-clotting factor, such as Protein C; atrial natriuretic factor; lung surfactant; a plasminogen activator, such as urokinase or tissue-type plasminogen activator (t-PA); bombazine; thrombin; tumor necrosis factor-α and -β; enkephalinase; RANTES (regulated on activation normally T-cell expressed and secreted); human macrophage inflammatory protein (MIP-1-α); serum albumin, such as human serum albumin; mullerian-inhibiting substance; relaxin, such as relaxin-2; prorelaxin; mouse gonadotropin-associated peptide; DNase; inhibin; activin; vascular endothelial growth factor (VEGF); receptors for hormones or growth factors; an integrin; protein A or D; rheumatoid factors; a neurotrophic factor, such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I); insulin-like growth factor binding proteins; CD proteins such as CD3, CD4, CD8, CD19 and CD20; erythropoietin (EPO); thrombopoietin (TPO); osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies, including therapeutic antibodies, and biologically active analogs, fragments or variants of any of the above-listed polypeptides.

In some embodiments, the term "polypeptide therapeutic or diagnostic agent" also includes any known and commercially available PEGylated polypeptide pharmaceutical agents, the non-limiting examples of which include Adynovate, Plegridy, Pegloticase, Certolizumab pegol (Cimzia), Methoxy polyethylene glycol-epoetin beta (Mircera), Pegaptanib (Macugen), Pegfilgrastim (Neulasta), Pegvisomant (Somavert), Peginterferon alfa-2a (Pegasys), Peginterferon alfa-2b (PegIntron), Pegaspargase (Oncaspar) and Pegademase bovine.

In one embodiment, the polypeptide therapeutic or diagnostic agent is relaxin, e.g., relaxin-2.

The cross-linker useful for preparing the sustained release formulations of the invention may comprise a polypeptide reactive moiety covalently attached to the polymer and the cleavable linker as illustrated by the following schematic:

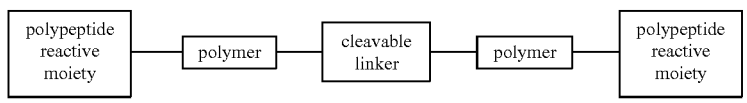

wherein the polypeptide reactive moiety may comprises an amine- or a thiol-reactive group; and the cleavable linker may comprise a moiety cleavable via a chemical or an enzymatic reaction.

In order to produce cross-links between the polypeptide therapeutic or diagnostic agent and the cross-linker as illustrated above, forming a hydrogel, at least three free amines and/or thiols need to be present on the relaxin. The polypeptide covalently attached to the polymer, e.g., a PEGylated polypeptide, is released from the hydrogel following hydrolysis of the cleavable linker in vivo.

The polypeptide reactive moiety on the cross-linker is an amine- or a thiol-relative group that reacts with a free amine group or a free thiol group on a polypeptide and becomes covalently attached to the polypeptide. In a specific embodiment, the polypeptide reactive moiety is an amine-reactive group, e.g., N-hydroxysuccinimide (NHS), sulfanated NHS, an aldehyde, a ketone, an acrylate and an epoxide.

In one embodiment, the polypeptide reactive moiety comprises an amine reactive group. In a further embodiment, the amine reactive group comprises a chemical group selected from the group consisting of: an isothiocyanate, an isocyanate, an acyl azide, an N-hydroxysuccinimide (NHS), a sulfonyl chloride, an aldehyde, a glyoxal, an epoxide, an oxirane, a carbonate, an aryl halide, an imidoester, a carbodiimide, an anhydride and a fluorophenyl ester. In a specific embodiment, the amine reactive moiety comprises NHS.

In certain embodiments of the invention, the polymer comprises PEG, e.g., a linear PEG or a branched PEG. In an embodiment, the PEG is a linear PEG. In certain embodiments, the PEG is a 5 kDa PEG, 10 kDa PEG, or 20 kDa PEG. In some aspects, the PEG may be represented by the following structural formula:

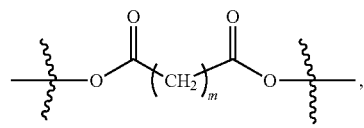

wherein n is 20-500, e.g., 20-50, 30-90, 40-120, 100-150, 120-200, 180-250, 210-270, 250-310, 290-350, 330-400, 350-450 or 400-500. In one embodiment, n is 46, 78 or 114.

In some embodiments, the cleavable linker is a polypeptide comprising an enzymatic cleavage site, e.g., a collagenase cleavage site, such as -APGL-; a plasmin cleavage site, such as Val-Ala-/-Asn; an elastase cleavage site, such as -Ala-Ala-Ala-Ala-Ala (SEQ ID NO: 17); and a metalloproteinase-2 cleavage site, such as -ESLAYYTA- (SEQ ID NO: 18).

Alternatively, the cleavable linker may comprise a moiety cleavable via hydrolysis. For example, in one embodiment, the moiety cleavable via hydrolysis has the following structural formula:

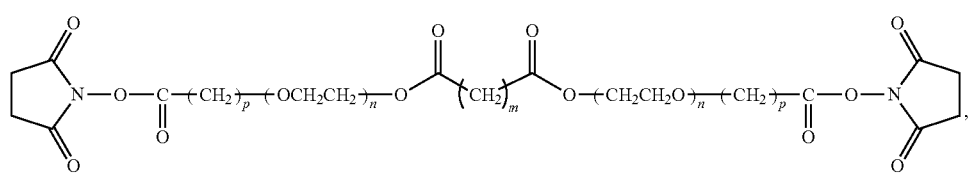

wherein m is any number from 1 to 10, e.g., 1, 2, 3, 4, 5, 6, 7, 8, 9 or 10. In one specific embodiment, m is 2. In another specific embodiment, m is 4.

In some embodiments, the cross-linker may have the following structural formula:

wherein n is 20-500; m is any number from 1 to 10; and p is any number from 1 to 6.

In one embodiment, n is 46, m is 2 and p is 1; n is 78, m is 2 and p is 1; n is 114, m is 2 and p is 1; n is 46, m is 6 and p is 1; n is 46, m is 10 and p is 1; n is 46, m is 2 and p is 4; n is 78, m is 2 and p is 4; n is 114, m is 2 and p is 4; n is 46, m is 6 and p is 4; or n is 46, m is 10 and p is 4.

Figure 6:
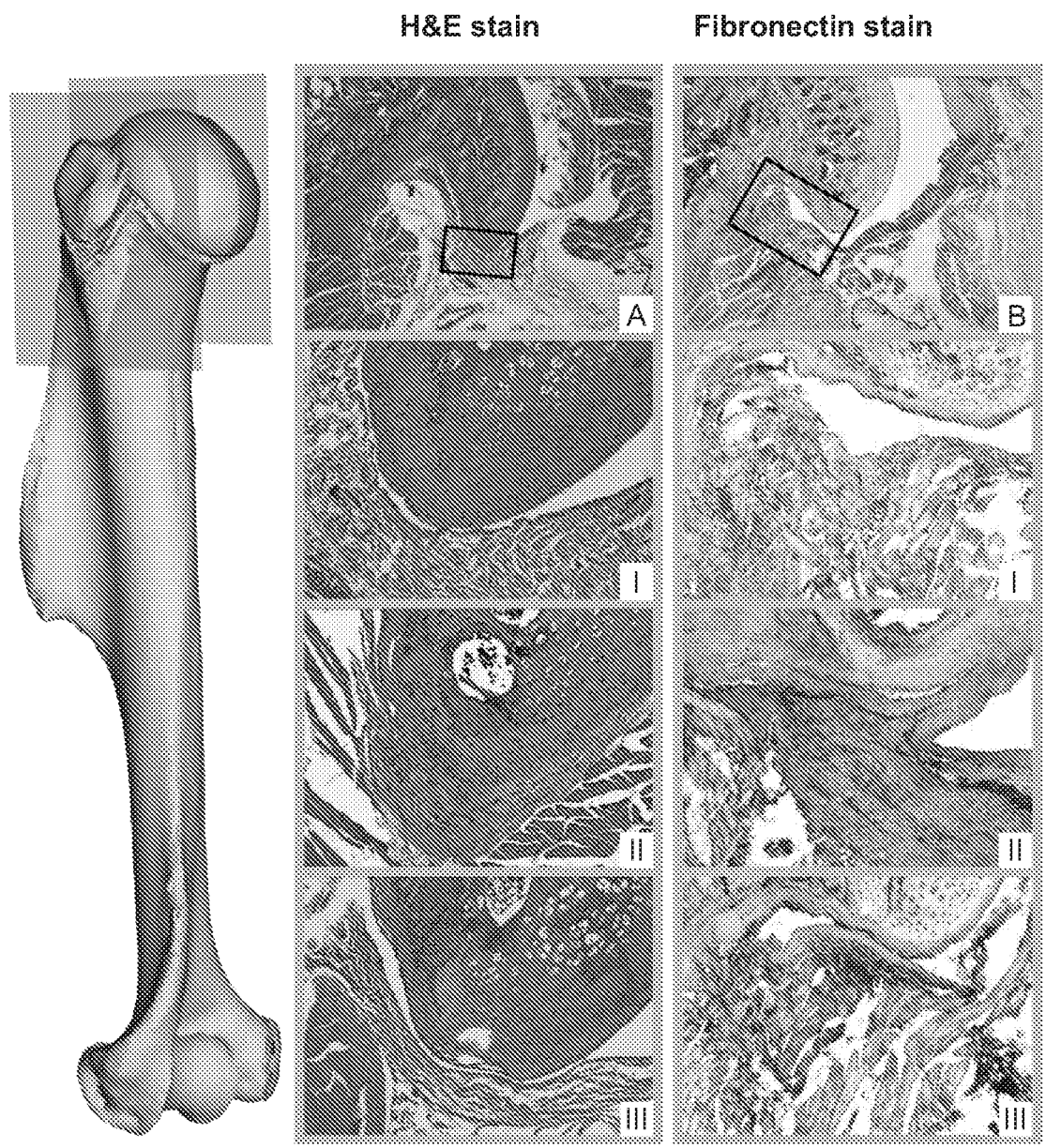
FIG. 6 is a series of images of coronal histologic slices of the affected humeral head. Lateral and medial directions correspond to the left and the right of the image, respectively. Colored planes transect the humerus where the color-coordinated slices were obtained. Panel A shows H&E stained images taken at 2.5× magnification. Panels I, II and III under Panel A, taken at 10× magnification, represent area marked by the black rectangle in Panel A and correspond to a healthy control (Panel I); contracture control (Panel II); and IAM Relaxin treated group (Panel III). Panel B shows images stained for fibronectin taken at 2.5× magnification. Panels I, II and III under Panel B, taken at 10× magnification, represent area marked by the black rectangle in Panel B and correspond to a healthy control (Panel I); contracture control (Panel II); and IAM Relaxin treated group (Panel III).

The linker comprising PEG as shown above may be synthesized according to the synthesis Scheme shown in FIG. 6.

The hydrogel sustained release formulation may be formed in situ following mixing of the polypeptide therapeutic or diagnostic agent and the cross-linker. For example, the hydrogel sustained release formulation may be formed after about 30 seconds, after about 25 seconds, after about 20 seconds, after about 15 seconds, or after about 10 seconds following mixing of the polypeptide therapeutic or diagnostic agent and the cross-linker. The mixing of the polypeptide therapeutic or diagnostic agent may take place immediately before or during delivery to the joint. The mixing of the polypeptide therapeutic or diagnostic agent and the cross-linker may take place in a mixing chamber in a syringe comprising two barrels and a mixing chamber.

The hydrogel sustained release formulation of the present invention may be formed by mixing together the relaxin and the cross-linker, thereby forming a hydrogel after about 30 seconds, after about 25 seconds, after about 20 seconds, after about 15 seconds, or after about 10 seconds following mixing of the relaxin and the cross-linker. In one embodiment, the hydrogel is formed in situ. This may be accomplished with the use of a syringe comprising two barrels and a mixing chamber. A solution comprising the cross-linker is added to one barrel, a solution comprising relaxin is added to the second barrel, and the two solutions are mixed in the mixing chamber immediately prior to the administration.

The mixing of the relaxin and the cross-linker may be carried out at a ratio of relaxin:cross-linker ranging from about 1:1 to about 10:1, e.g., about 1:1 to about 3:1, about 2:1 to about 4:1, about 3:1 to about 5:1, about 4:1 to about 6:1, about 5:1 to about 7:1, about 6:1 to about 8:1, about 7:1 to about 9:1 or about 9:1 to about 10:1 relaxin:cross-linker. In some embodiments, the ratio of relaxin:cross-linker may be about 1:1, about 2:1, about 3:1, about 4:1, about 5:1, about 6:1, about 7:1, about 8:1, about 9:1 or about 10:1 of relaxin:cross-linker. In one embodiment, the ratio of relaxin:cross-linker may be about 10:1, about 4:1, about 2:1 or about 1:1 of the relaxin:cross-linker. The mixing may also be carried out in the presence of a filler polypeptide, e.g., albumin, such that the resulting hydrogel additionally comprises a filler polypeptide covalently attached to the PEG. The filler polypeptide, e.g., albumin, may be mixed with the relaxin and the cross-linker at a ratio of about 1:1 to about 10:1 of relaxin and albumin:cross-linker, e.g., about 1:1 to about 3:1, about 2:1 to about 4:1, about 3:1 to about 5:1, about 4:1 to about 6:1, about 5:1 to about 7:1, about 6:1 to about 8:1, about 7:1 to about 9:1 or about 9:1 to about 10:1 relaxin and albumin:cross-linker. In some embodiments, the ratio of relaxin and albumin:cross-linker may be about 1:1, about 2:1, about 3:1, about 4:1, about 5:1, about 6:1, about 7:1, about 8:1, about 9:1 or about 10:1 of relaxin and albumin:cross-linker. In one embodiment, the ratio of relaxin and albumin:cross-linker may be about 1:1, about 2:1, about 4:1 or about 10:1 In some embodiments, the mixing may also be carried out at the ratio of albumin:relaxin of about 5:95 to about 95:5, e.g., about 5:95 to about 50:70, about 10:90 to about 75:25, about 50:50 to about 95:5 of albumin:relaxin. For example, the mixing may be carried out at a ratio of albumin:relaxin of about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10 or about 95:5 of albumin:relaxin.

In some aspects, the present invention also provides a syringe suitable for delivering the sustained release formulation of the invention to a subject in need thereof. The syringe comprises a first barrel comprising the polypeptide therapeutic or diagnostic agent; and a second barrel comprising the cross-linker comprising a polymer; and a mixing chamber for mixing the polypeptide therapeutic or diagnostic agent and the cross-linker comprising a polymer immediately prior to delivery. In one embodiment, the polymer is PEG.

In some embodiments, the first barrel may additionally comprise a filler polypeptide that may be mixed with the polypeptide therapeutic or diagnostic agent. The filler polypeptide may be an inert polypeptide that does not exhibit a biological activity when delivered to a subject. One example of such filler polypeptide is albumin, e.g., a human albumin. The inclusion of the filler polypeptide may facilitate the preparation of a sustained release hydrogel suitable for delivering low doses of the polypeptide therapeutic or diagnostic agent, i.e., doses requiring an amount of the polypeptide that would otherwise not effectively form a hydrogel.

In one embodiment, the polypeptide therapeutic or diagnostic agent comprised in the syringe of the invention is relaxin or an analog, a fragment or a variant thereof, e.g., relaxin-2. In another embodiment, the syringe may be suitable for an intraarticular injection and may comprise a needle, e.g., a 30 G needle, a 29 G needle, a 28 G needle, a 27 G needle, a 26 sG needle, a 26 G needle, a 25.5 G needle, a 25 sG needle, a 25 G needle, a 24.5 G needle, a 24 G needle, a 23.5 G needle, a 23 sG needle, a 23 G needle, a 22.5 G needle, a 22 sG needle, a 22 G needle, a 21.5 G needle, a 21 G needle, a 20.5 G needle, a 20 G needle, a 19.5 G needle, a 19 G needle, a 18.5 G needle, a 18 G needle. In one specific example, the syringe may comprise a 21 G needle.

EXAMPLES

Unless provided otherwise, the hyaluronan used in the compositions described herein is obtained from animal, human or bacterial sources. Unless provided otherwise, the compositions used herein are in physiological buffers.

Example 1: Evaluation of a Shoulder Contracture Model in Rats

The purpose of this experiment, which is described in the publication by Villa-Camacho et al., *Journal of Shoulder and Elbow Surgery*, 2015, 24(11):1809-16, was to investigate the effects of extra-articular, internal fixation of the glenohumeral joint on shoulder kinetics and kinematics in an in vivo animal model of shoulder contracture. It was expected that extra-articular, internal fixation of the shoulder in rats would result in a subsequent decrease in rotational ROM and an increase in joint stiffness, which would persist for at least 8 weeks.

The study was approved by the Institutional Animal Care and Use Committee, and 10 Sprague-Dawley rats (250-300 g, Charles River Laboratories, Wilmington, Mass., USA) were used in the study. For each animal, torque was measured per degree, on the intact left shoulder as a function of rotation angle between 80° of internal rotation (negative values by convention) and 60° of external rotation (positive values by convention) prior to any surgical intervention (baseline). Rotation was confined within boundaries that were observed to elicit minimal scapular recruitment, as confirmed by fluoroscopy. Therefore, torque values at 80° external rotation ($\tau_{OUT}$) and 60° of internal rotation ($\tau_{INT}$) were recorded for each animal.

The left forelimb of each animal was immobilized using extra-articular internal fixation. Under isoflurane anesthesia, a longitudinal skin incision was made perpendicular to the scapular spine. Two No. 2-0 braided polyester sutures (Ethibond Excel, Ethicon—San Lorenzo, PR, USA) were passed between the medial border of the scapula and the humeral shaft and tightened to immobilize the shoulder joint (FIG. 1, panel A). Muscular structures were not manipulated during surgery, and the animals were allowed normal activity in their cages immediately after the procedure.

After 8 weeks of immobilization, the restraining sutures were removed, and the 10 animals were divided into two groups to evaluate changes in ROM (ROM group, n=5) and joint stiffness (stiffness group, n=5). In the ROM group, changes in kinematics were longitudinally quantified in the follow-up period by measuring the ROM achieved with the $\tau_{OUT}$ and $\tau_{INT}$ measured at baseline. This was conducted to evaluate whether immobilization mediated a significant reduction in ROM. In the stiffness group, joint kinetics were examined by measuring the differences in $\tau_{OUT}$ and $\tau_{INT}$ needed to achieve the original 80° of internal rotation and 60° of external rotation, respectively. Measurements for both groups were taken immediately after suture removal (day 0 of follow-up) and at regular intervals thereafter (twice a week until less than 10% change was observed in three consecutive time points, when, measurement frequency was reduced to once a week). The baseline measurements for each group were used as internal controls to reduce the total number of animals necessary for the study. The use of internal controls also increased internal validity and statistical power as there was a high inter-specimen variation, of both ROM and measured torques, even when using the contralateral shoulder of the same animal. Finally, a pilot study demonstrated that intra-specimen measurements were highly reproducible and remained stable during an 8-week period.

ROM and torque measurements were performed under general anesthesia using a device that consisted of a sensor assembly, a rotating axle, and an arm clamp. The sensor assembly contained an orientation sensor (3DM-GX3-15, MicroStrain—Williston, Vt.), as well as a reaction torque sensor (TFF400, Futek—Irvine, Calif.) secured to the axle such that the sensing axis was collinear with the center of rotation. The forelimb was secured at 3 points (wrist, elbow, and arm), ensuring that the sensing axis was aligned with the long axis of the humerus (FIG. 1, panel B). Rotation of the sensor assembly resulted in direct internal humeral rotation (FIG. 1, panel C) and external humeral rotation (FIG. 1, panel D) within the glenohumeral joint.

To reproducibly capture ROM and torque, passive limb rotation was performed by a stepper motor controlled with a microcontroller (UNO R3, Arduino—Torino, Italy). The system utilized inputs from the reaction torque sensor or the orientation sensor to start and end the dynamic measurement of ROM and torque. In the ROM group, pre-set programmable torque values, specific for each animal and measured at baseline ($\tau_{OUT}$ and $\tau_{INT}$), were input variables in order to detect changes in rotation ROM with 0.20 resolution. In the stiffness group, pre-set programmable rotation angles (60° external rotation, 80° internal rotation) were used as input to measure changes in torque at a resolution of 0.01 N/mm. The microcontroller was directed by a computer using MATLAB 7.13.0.564 (MathWorks Inc—Natick, Mass., USA).

Figure 2:
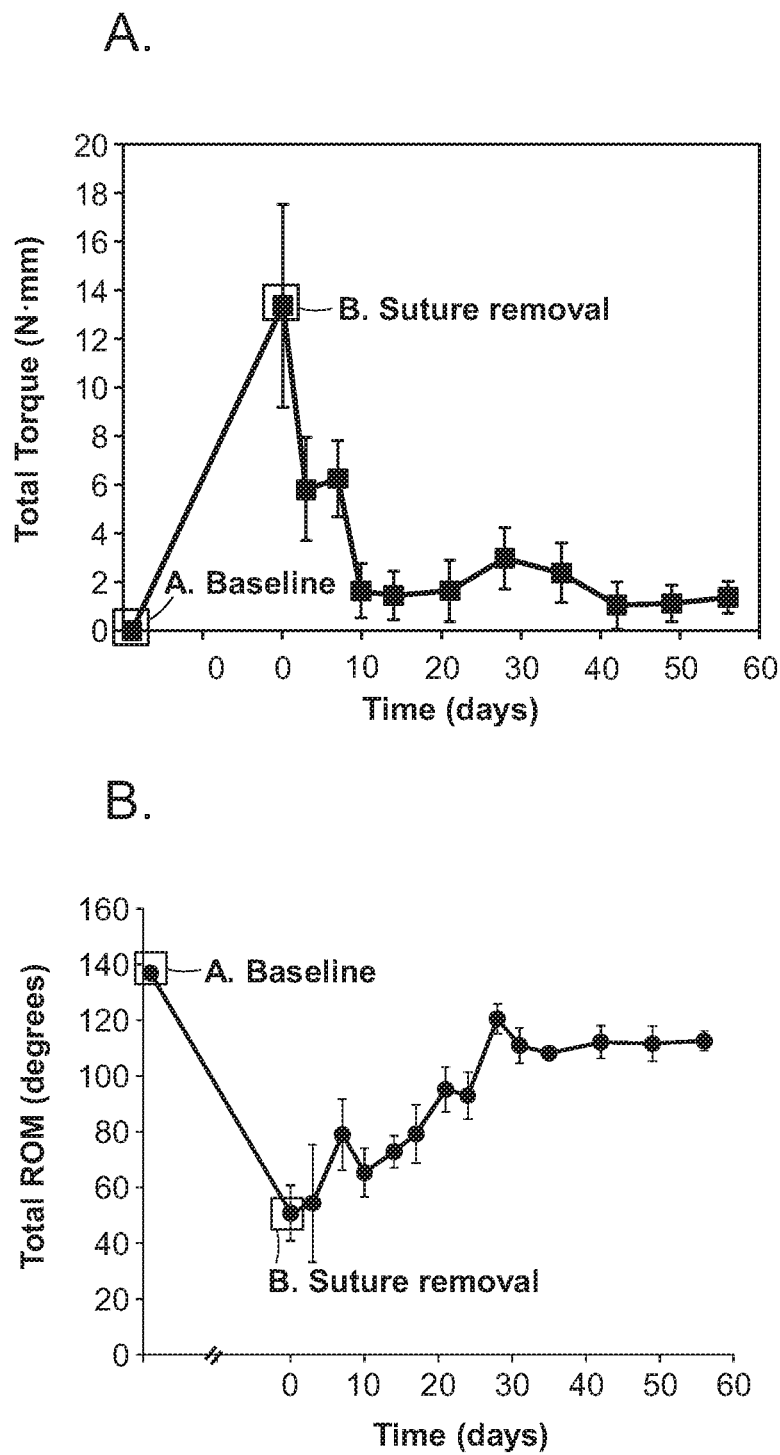
FIG. 2, panel A is a graph illustrating total torque ($\tau_{OUT} + \tau_{INT}$) in a shoulder contracture model in rats over time.

In the ROM group, mean ROM values were compared at three different time points (baseline, immediately after suture removal, and at 8 weeks of follow-up) by repeated-measures analysis of variance. In the stiffness group, two different metrics were used for comparison: 1) the difference in torque required to achieve full ROM, and 2) stiffness, estimated from the area under the rotation angle-torque curve. A value of P<0.05 was considered statistically significant for both groups. The ROM temporal behavior in the follow-up period is shown in FIG. 2. Immediately after suture removal, there was a 63% decrease in total ROM compared with baseline (510°±10° vs. 136°±0°; P<0.001; FIG. 2, panel B). Similarly, total torque increased 13.4 N·mm compared with baseline (22.6±5.9 N·mm vs. 9.2±2.6 N·mm; P=0.002; FIG. 2, panel A). Residual total ROM restrictions and an increased torque in internal rotation were still evident at 8 weeks of follow-up (113°±8° vs. 137°±0°, P<0.001 and 3.5±0.4 N·mm vs. 2.7±0.7 N·mm, P=0.036).

The kinetic and kinematic changes were not transitory. At 8 weeks follow-up, both the reduction in ROM and the increase in joint stiffness were significant. While no studies have evaluated the natural progression and temporal behavior of this shoulder contracture model, it is expected that joint residual changes present after 8 weeks into the post-immobilization period are likely permanent (Trudel G. et al., *Journal of Applied Physiology* (Bethesda, Md.: 1985), 2014, 117(7):730-7). The results presented in Example 1 indicate that a shoulder contracture model in rats may be used to evaluate therapeutic interventions to treat shoulder contracture.

Figure 3:
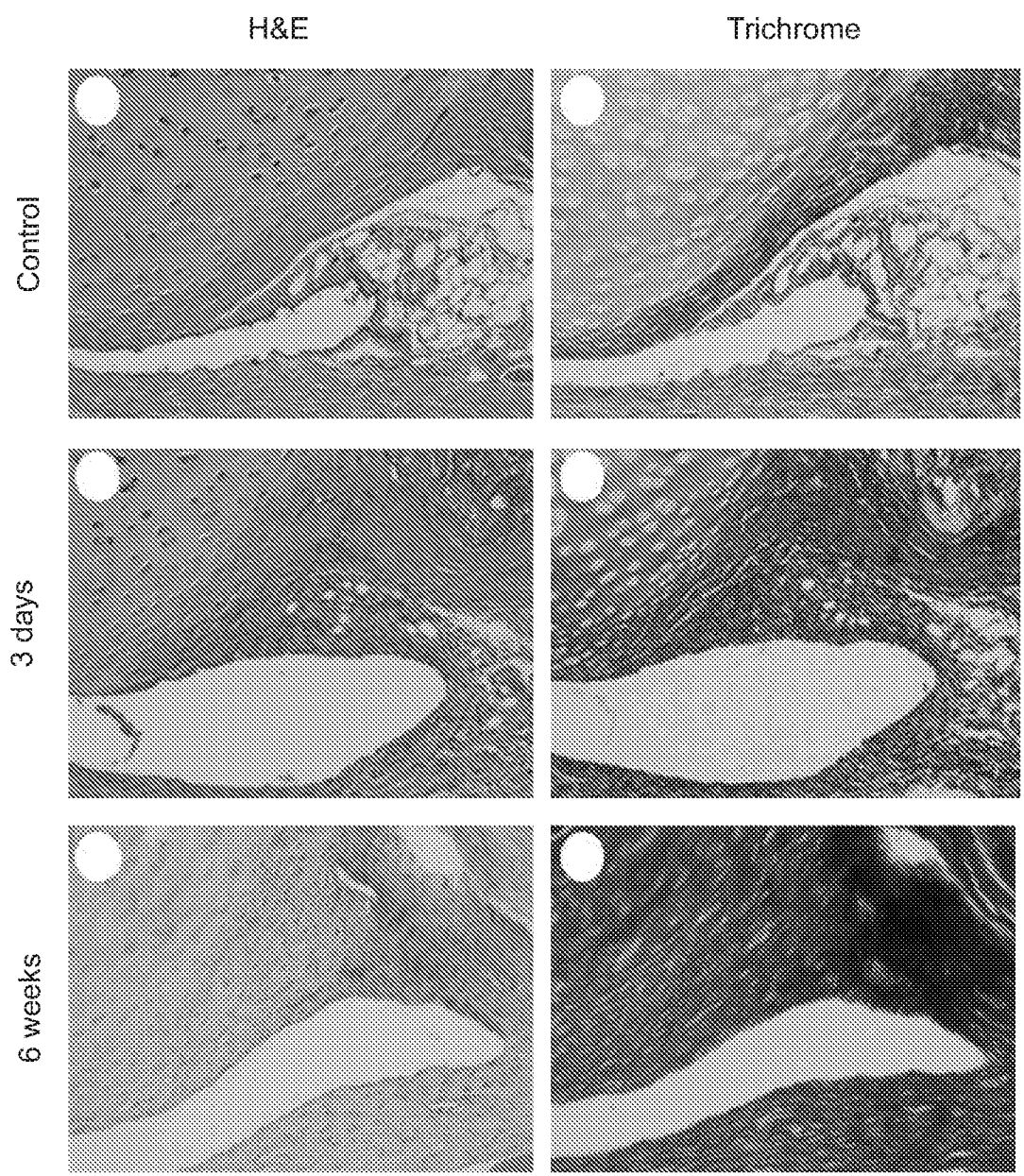
FIG. 3 is a series of microscopic images as seen in Kim et al., *J. Orthop. Surg. Res.* 2016; 11(1): 160, taken over 6 weeks of the axillary recess of the glenohumeral joint.

The above described findings were subsequently validated by Kim et al., who independently reported a similar model of shoulder contracture (Kim et al., *J. Orthop. Surg. Res.* 2016; 11(1):160). FIG. 3 is a series of microscopic images as seen in Kim et al., taken over 6 weeks of the axillary recess of the glenohumeral joint. The trichrome stain utilized Masson's trichrome to identify fibrosis (red). FIG. 3 provides histologic evidence of contracture development at 3 days and 6 weeks. Fibrosis and inflammation occurred early and persisted during immobilization, and notably, the infiltration of inflammatory cells, capsular thickening, and angiogenesis within capsular tissue was apparent within as early as 3 days. While the acute inflammatory response lessened by week 6, capsular thickening and fibrotic structures still remain, closely mimicking findings from other studies (Trudel et al., *J. Appl. Physiol.* (1985), 2014, 117(7):730-7). This model of a lasting reduced ROM and increased stiffness allows for the comprehensive evaluation of current and potential therapeutic interventions for shoulder contracture.

Example 2. Restoration of ROM in Rats with Multiple Doses of Relaxin

The aim of this study was to investigate the effects of recombinant human relaxin 2 on the kinetics and kinematics of the glenohumeral joint in an animal model of shoulder contracture. It was expected that rats treated with intra-articularly administered relaxin would exhibit a greater ROM after 8 weeks of follow-up than untreated controls.

Materials and Methods

Specimen Preparation

Figure 4:
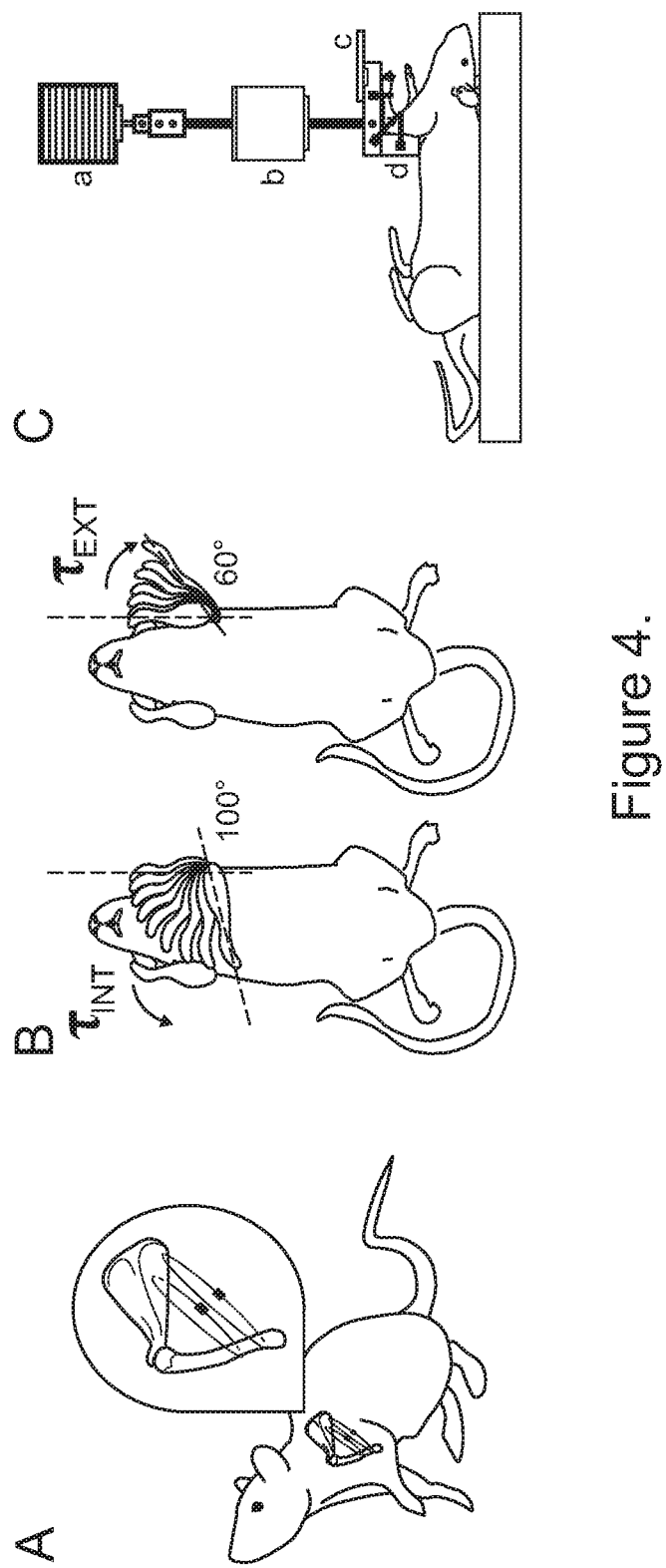
FIG. 4, Panels A, B, C and D are a series of drawings illustrating ROM measurements in rats.

On the approval of the Institutional Animal Care and Use Committee (IACUC) at Beth Israel Deaconess Medical Center, 20 Female Sprague Dawley rats (250-300 g, Charles River Laboratories, Inc., Wilmington, Mass., USA) were chosen for this study. Baseline ROM measurements were taken for both forelimbs of each rat prior to any surgical intervention. Torque measurements were recorded at 100° of internal rotation ($\tau_{INT}$) and 60° of external rotation ($\tau_{OUT}$), totaling a full 160° range of motion (ROM) (FIG. 4, Panels B and C). These measurements were required as they indicate a baseline for normal torque necessary to achieve both rotations. The specific rotation angles were chosen under fluoroscopic guidance to ensure minimal scapular recruitment, while simultaneously allowing for maximum humeral rotation within the joint space. Each ROM measurement was repeated three times to ensure consistency. All measurements were also performed under anesthesia to prevent any active muscle activation from interfering with the passive capsular resistance. Induction of the rats was performed at 5% isoflurane inhalation, and maintenance was managed at a 2% isoflurane dose.

After the baseline measurements and under anesthesia, 20 rats were subjected to the immobilization procedure as outlined in Example 1 and in Villa-Camacho et al., *Journal of Shoulder and Elbow Surgery*, 2015, 24(11):1809-16, to induce fibrosis. In short, an incision was created longitudinally on the left limb, perpendicular to the scapular spine, to expose both the scapula and humerus. A No. 2-0 Ethibond polyester suture (Ethicon, San Lorenzo, PR, USA) was used to immobilize the humerus to the scapula by passing two loops through the medial border of the scapula and against the humeral shaft (FIG. 4, Panel A). Care was taken to ensure that the sutures avoided critical vasculature, musculature, and nerves. Each rat was maintained under fixation for 8 weeks. After the eighth week, the suture fixations were removed, and the rats were randomly placed in four groups: (1) intra-articular relaxin, single dose (IAS) (n=5); (2) intra-articular relaxin, multiple doses (IAM) (n=5); (3) intravenous relaxin, multiple doses (IVM) (n=5); and (4) untreated surgical controls (n=5). The sample size was determined with a power of 0.80 and α=0.05 if a 10% increase in range of motion from contracture was to be expected.

Mechanical Testing Apparatus

The mechanical testing apparatus was assembled with four core components and controlled with a computer through custom-built software written on MATLAB 7.13.0.564 (The MathWorks, Inc., Natick, Mass., USA). Movement of the forelimb was mediated by a stepper motor controlled by a microcontroller (UNO R3; Arduino, Torino, Italy). The motor was then positioned axially with the reaction torque sensor (TFF400; FUTEK Advanced Sensor Technology, Inc., Irvine, Calif., USA), which measured torque and was utilized as an input feedback for the system. Along the same axis, the arm clamp and the 3-axis inclinometer (3DM-GX3-15; MicroStrain, Inc., Williston, Vt., USA) were attached on the sensing side of the torque sensor. The inclinometer also provided both positional feedback as well as angular measurements for the system. The entire assembly was positioned above the rat with the sensing plane parallel to the ground to ensure that gravity had little impact on the torque measurements (FIG. 4). The apparatus was programmed to move to a specified torque or angle for internal and external rotation for each rat. Plastic zip ties were used to secure the rat forelimb in the apparatus. Care was taken to prevent any injury, and the apparatus was programmed with an internal and external limit switch in the case the apparatus operated abnormally.

Treatment and Measurement of Study Groups

Immediately after removal of the restraining sutures, relaxin was administered to the noncontrol group rats. Human relaxin-2 was administered by intra-articular (IA) injection into the anesthetized rats under fluoroscopic guidance, and was comprised of 0.0005 mg relaxin diluted in 100 μL of phosphate-buffered saline (PBS; 0.0015 mg/kg). Relaxin that was dispensed by intravenous (IV) injection through the tail was dosed at 0.17 mg relaxin diluted in 100 μL PBS (0.5 mg/kg). For the groups that required multiple doses of relaxin, intra-articular and intravenous injections were provided every 2 days over the first 10 days of the post-immobilization period (5 doses; total relaxin: IA 0.0025 mg, IV 0.85 mg). For days where treatment and ROM measurement overlapped, treatment was administered first. Injection of each intra-articular aliquot of relaxin was performed with a 27-gauge needle (PrecisionGlide; Becton, Dickinson and Company, Franklin Lakes, N.J., USA).

Subsequent kinematic measurements were performed randomly and in a blinded manner after treatment. Each measurement was longitudinally spaced in the follow-up period of 8 weeks as determined by a previous study (Villa-Camacho et al., *Journal of Shoulder and Elbow Surgery*, 2015, 24(11):1809-16). These measurements examined the change in ROM angles by using the $\tau_{INT}$ and $\tau_{OUT}$ recorded at baseline as a reference threshold. The apparatus was programmed so that each rat was measured based on its own individual baseline torque values. This was done to eliminate any variation across rats, allowing each rat to reach an individualized torque that corresponds to their specific baseline ROM (Villa-Camacho et al., *Journal of Shoulder and Elbow Surgery*, 2015, 24(11):1809-16). Each of these measurements occurred biweekly within the first two weeks and then weekly throughout the follow-up period. This scheduling was done to limit specimen exposure to isoflurane. Additionally, kinematic changes had been found to occur rapidly only within the first two weeks and become generally steady for the remainder of the 8 weeks (Villa-Camacho et al., *Journal of Shoulder and Elbow Surgery*, 2015, 24(11): 1809-16). Each measurement was taken under anesthesia and repeated three times for both forelimbs to ensure accuracy.

Immunohistologic Analysis

At the conclusion of the follow-up period, the rats were euthanized according to IACUC guidelines. The rats were weighed and then subjected to $CO_2$ exposure for euthanasia, and further confirmed through a bilateral thoracotomy. The shoulders were bilaterally harvested by disarticulating the humerus from the ulna, and removing the scapula from the clavicle and thoracic cavity. Excess muscle tissue not immediately surrounding the glenohumeral joint capsule was removed. The excised shoulders were decalcified for two months in a solution of ethylenediaminetetraacetic acid (EDTA), which was changed every two to three days. Once decalcified, the shoulders were affixed in a solution of 10% formalin and then mounted in paraffin stacks for histological sectioning at the Beth Israel Deaconess Medical Center (BIDMC) Histology Core. These stacks were mounted so that coronal slicing could be obtained. The slices were stained with hematoxylin and eosin (H&E) and examined for any morphological changes. These slices were taken from a posterior region of humeral head to better find evidence of periarticular adhesions (Brue et al., *Knee Surg. Sports Traumatol. Arthrosc.*, 2007, 15(8):1048-54; White et al., *Radiographics,* 2016, 36(3):824-39). Further slices, taken mid-coronally, were also stained with fibronectin antibodies paired with peroxidase to further examine fibrotic characteristics such as capsular thickening. Collagen III, α-smooth muscle actin, and other acute fibrotic markers were not chosen for analysis, since histologic sectioning would occur 4 months after contracture creation.

The specimen chosen to undergo histological analysis were the surgical control group and the IAM group. The IAM group was chosen because this group received the highest and most frequent dose of relaxin, and was, therefore, the best candidate to showcase any morphologic changes due to relaxin administration. The contralateral shoulders from the surgical control group were used to model a healthy control shoulder for histologic comparisons.

Data and Statistical Analysis

Comparisons in kinematic changes were done by comparing the change in ROM between the baseline measurement and the measurements that followed immobilization and treatment. The change in ROM was calculated using a MATLAB script to maintain proper randomization and blinded data processing for the comparisons. ROM measurements were shown as total ROM averages along with 95% confidence intervals. Standard deviations described all variances. Changes in ROM were examined across groups at each measurement time point. Statistical differences across groups were performed by repeated measures analysis of variance (ANOVA) and Tukey HSD. Significance was determined using an alpha level of 0.05 (P<0.05), and confidence intervals of 95% were chosen. Tests for normality were defined using the Shapiro-Wilk test for normality.

Results

Biomechanical Results

At a healthy baseline prior to surgery, all rats attained a full ROM of 159.17°±0.94°. After 8 weeks of immobilization, all rats attained an overall ROM of 91.17°±10.11° immediately after suture removal, a significant reduction (43.22%±6.31%) from baseline (P<0.01). The IAM group (P=0.48), the IAS group (P=0.93), and the IVM group (P=0.99), were shown to be statistically as restricted in ROM as the control group. All data was found to be normally distributed based on the Shapiro-Wilk test for normality (P=0.54).

Figure 5:
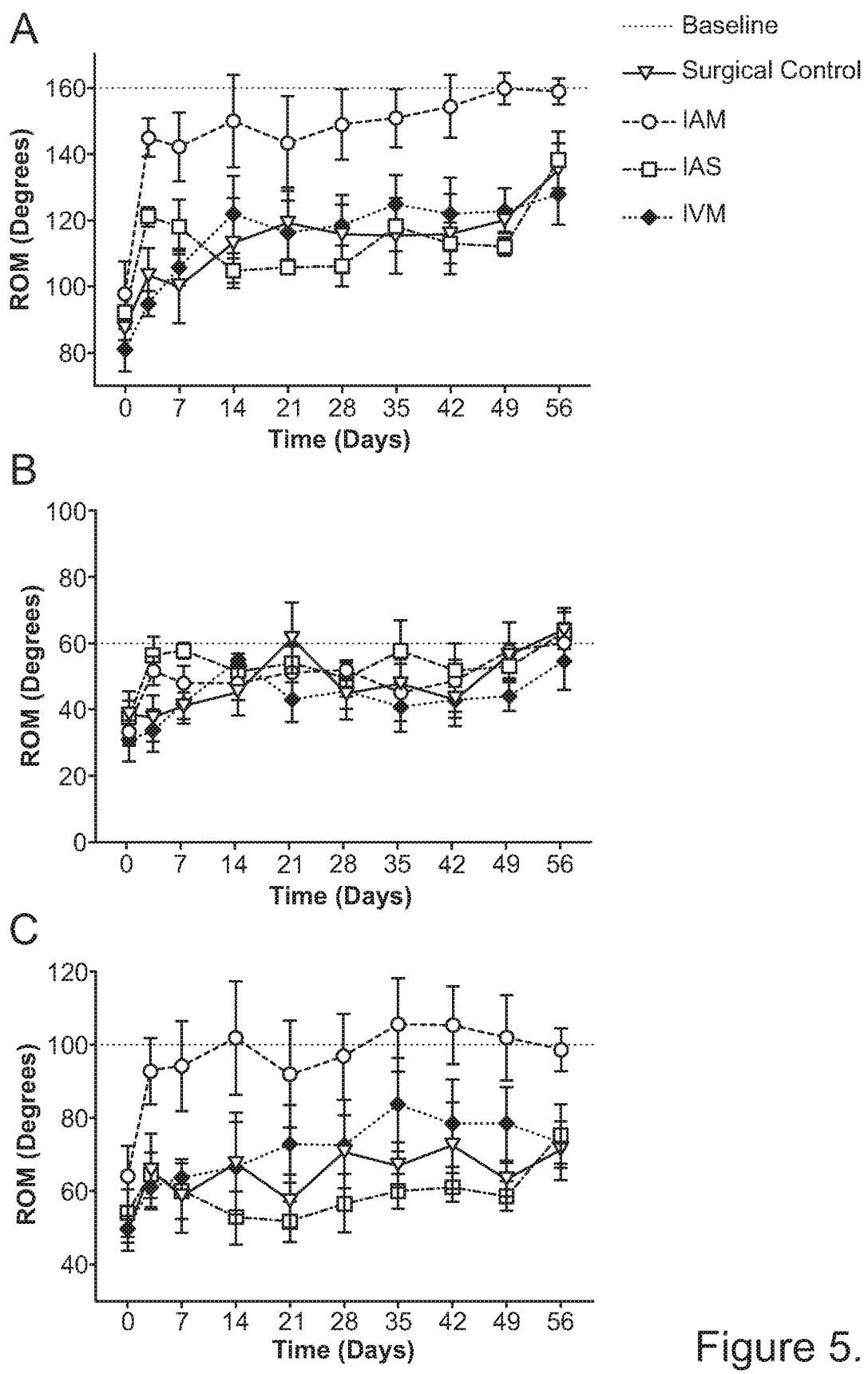
FIG. 5 is a series of graphs showing temporal results of the total ROM (Panel A); external ROM (Panel B); internal ROM (panel C); normalized torque-angle curve of the final measurements (Panel D); and the final achieved internal and external ranges of motion (Panel E). In Panels A, B and C, surgical control is represented by triangles; intra-articular relaxin, multiple doses (IAM) is represented by circles; intra-articular relaxin, single dose (IAS) is represented by squares and intravenous relaxin, multiple doses (IVM) is represented by diamonds.
Figure 5:
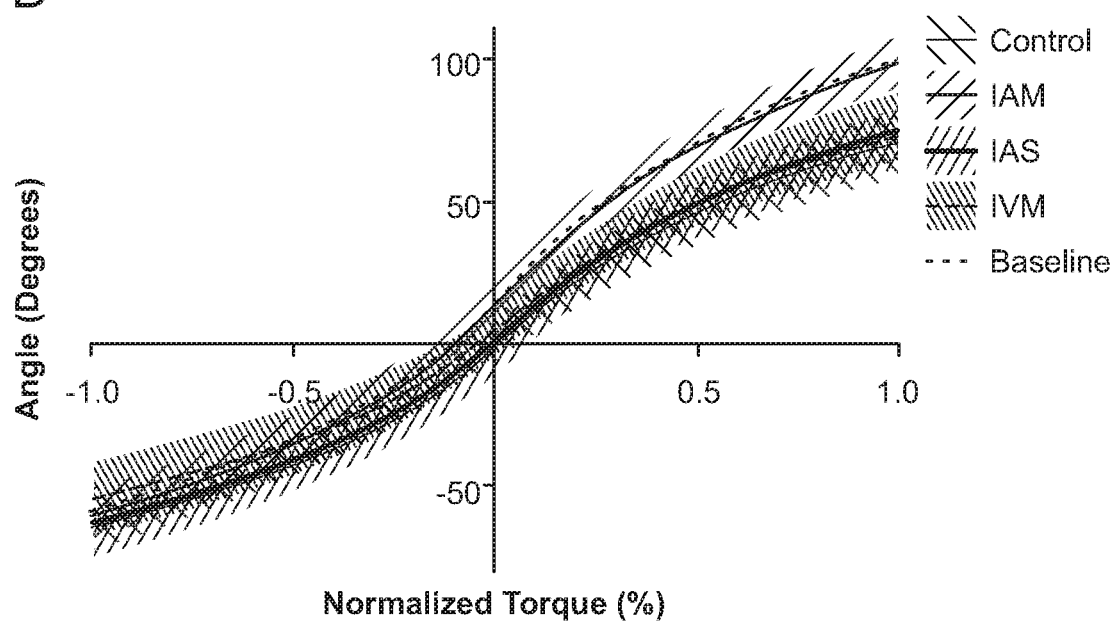
Figure 5:
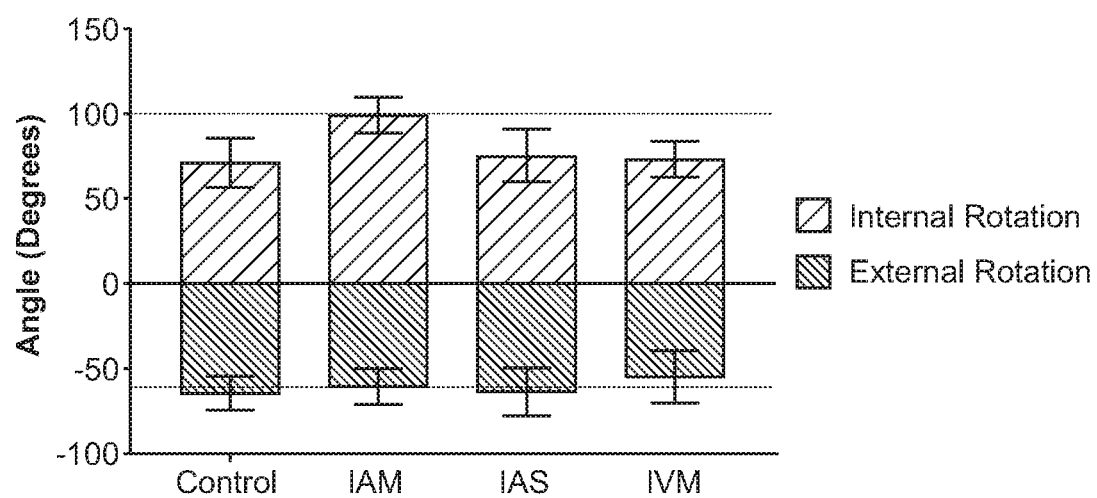

The final ROM measurements are reported in Table 1 below, and measurements over time are presented in FIG. 5. Specifically, FIG. 5 is a series of graphs showing temporal results of the total ROM (Panel A); external ROM (Panel B); internal ROM (panel C); normalized torque-angle curve of the final measurements (Panel D); and the final achieved internal and external ranges of motion (Panel E). In Panel A, temporal results of the total ROM are presented as means with a 95% confidence interval. Baseline describes a healthy control, whereas control describes the surgical control group, i.e., operated animals with induced joint stiffness and no treatment. Day 0 signifies suture removal and the first measurement. Significance is defined at α=0.05. B.) In Panel D, which shows normalized torque-angle curve of the final measurement, normalization was performed to better equate changes in achieved angle vs. expected torque. Shaded colored regions signify a 95% confidence interval. Negative angles and torques show external rotation and positive angles describe internal rotation. In Panel E, shown are the means and their standard deviations.

The surgical control group remained constricted by −23.67°, or −14.88% (P<0.01) when compared to baseline, a finding consistent with previous studies (Kanno et al., *J. Shoulder Elbow Surg.,* 2010, 19(5):700-8; Villa-Camacho et al., *Journal of Shoulder and Elbow Surgery,* 2015, 24(11): 1809-16; Oki et al., *J. Orthop. Res.,* 2015, 33(11):1732-8). Similarly, the IVM group displayed a significant restriction of −30.73°, or −19.42% (P<0.01) when compared with baseline. The IAS group showed a slight improvement with its ROM, being restricted by −21.72°, or −13.57% (P<0.01). However, this increase was not found to be significant, when compared with the control (Table 1). In contrast, the IAM group was not statistically different from the baseline measurements (P=0.94). Of interest, the IAM group was also significantly improved when compared with the control group (P<0.01). All other groups were not significantly different from the surgical control group (Table 1). Analysis of internal and external ROM separately also displayed that external ROM showed no significant differences from baseline. Additionally, external ROM exhibited no differences between the surgical control and the other groups. Significant improvements were found only when the forelimbs were internally rotated in the IAM group. Improvements in the IAM group were found to sharply rise at the second measurement and continue up until day 49 (FIG. 5, Panels A and C). The healthy contralateral forelimbs showed no significant change from baseline during ROM measurements. (Surgical control (P=0.96), IAM (P=0.96), IAS (P=0.95), IVM (P=0.89), F Statistic=879.78).

Further examination of the final measurement's torque curve highlights a similar behavior between the IAM group and the original baseline torque profile (FIG. 5, Panel D). This further illustrates that, given the starting position of the rat's forelimb in this study, internal rotation is the most affected by an immobilizing surgical contracture. As additional evidence for the results previously stated, internal rotation is most affected throughout the torque-angle profile. FIG. 5, Panel E illustrates the final ROMs achieved on the final day for both internal and external rotations.

TABLE 1

Final Ranges of Motion for Each Group.

| Group | Baseline ROM (°) | Final ROM (°) | Difference ROM (% Δ°) | 95% CI (Δ°) | | F | P |
|---|---|---|---|---|---|---|---|
| Total ROM | | | | | | | |
| Control | 159.07 ± 1.36 | 135.40 ± 14.29 | −14.88 | −32.50 | −16.70 | 14.17 | — |
| IAM | 158.80 ± 1.07 | 159.13 ± 6.97 | 0.21 | −4.70 | 3.00 | | <0.01* |
| IAS | 160.13 ± 0.90 | 138.40 ± 15.34 | −13.57 | −30.10 | −13.10 | | 0.93 |
| IVM | 158.67 ± 1.22 | 127.93 ± 16.35 | −19.37 | −41.10 | −23.00 | | 0.45 |

TABLE 1-continued

Final Ranges of Motion for Each Group.

| Group | Baseline ROM (°) | Final ROM (°) | Difference ROM (% Δ°) | 95% CI (Δ°) | | F | P |
|---|---|---|---|---|---|---|---|
| External ROM | | | | | | | |
| Control | 59.33 ± 0.97 | 64.13 ± 10.21 | 8.09 | −1.52 | 9.79 | 1.64 | — |
| IAM | 59.67 ± 0.58 | 60.27 ± 11.05 | 1.01 | −5.86 | 6.39 | | 0.84 |
| IAS | 60.00 ± 0.71 | 63.13 ± 14.20 | 5.22 | −4.73 | 11.00 | | 0.99 |
| IVM | 59.33 ± 0.85 | 54.67 ± 15.30 | −7.87 | −13.80 | 3.14 | | 0.19 |
| Internal ROM | | | | | | | |
| Control | 99.73 ± 0.72 | 71.27 ± 14.58 | −28.54 | −36.81 | −20.66 | 14.77 | — |
| IAM | 99.13 ± 0.61 | 98.87 ± 10.63 | −0.27 | −7.02 | 4.80 | | <0.01* |
| IAS | 100.13 ± 0.69 | 75.27 ± 15.62 | −24.83 | −33.38 | −16.08 | | 0.83 |
| IVM | 99.33 ± 0.53 | 73.27 ± 10.35 | −26.24 | −32.46 | −21.00 | | 0.97 |

* Significance at P < 0.05.

A complete range of motion is expected to be near 160°. A negative change in ROM describes a difference in final ROM that is lower than a normal ROM. A positive change indicates a final ROM that is greater than the baseline measurement. Significance is determined at $\alpha=0.05$. The P-value is the result of a comparison between the final control ROM and the ROM of each of the different groups.

Another noteworthy result was the sharp improvement in ROM found in the IAS group at the measurement immediately following the day 0 measurement (FIG. 5, Panel A). This increase seems similar to that of the IAM group, showing improvements of 11.87° in ROM over the surgical control group. This increase for IAS was found to be significant as well (P=0.025). After the second measurement however, the IAS group began to drop and trend below all the other groups for some time. This trend was not found to be significantly different than the control group at any point in time.

Histology

Shown in FIG. 6 are coronal histologic slices of the affected humeral head. Lateral and medial directions correspond to the left and the right of the image, respectively. Colored planes transect the humerus where the color-coordinated slices were obtained. FIG. 6, Panel A shows H&E stained images taken at 2.5× magnification. Panels I, II and III under Panel A, taken at 10× magnification, represent area marked by the black rectangle in Panel A and correspond to a healthy control (Panel I); contracture control (Panel II); and IAM Relaxin treated group (Panel III). FIG. 6, Panel B shows images stained for fibronectin taken at 2.5× magnification. Panels I, II and III under Panel B, taken at 10× magnification, represent area marked by the black rectangle in Panel B and correspond to a healthy control (Panel I); contracture control (Panel II); and IAM Relaxin treated group (Panel III).

When compared to with the healthy control group, the H&E stained sections for the surgical control group showed morphological changes to the surrounding capsular tissue. As is seen in FIG. 6, Panel I under Panel A, the healthy control displayed a well-delineated separation between the capsule and the articular surface on the humeral head. The synovial membrane and the articular cartilages showed normal cellular organization. However, the surgical control group in FIG. 6, Panel II under Panel A lacked this separation in the most inferior aspect of the glenohumeral joint and showed evidence of capsular adhesions. Histologic evidence also pointed to a capsule that more tightly surrounds the humeral head, a morphologic characteristic associated with contracture (Lee et al., J. Comput. Assist. Tomogr., 2017, 41(1):116-20.). The membrane and cartilage nuclei failed to maintain the expected tangential orientation to the humeral head within the superficial zone (tangential zone) and instead showed an orthogonal directionality from the expected surface contour. Evidence of these adhesions supports the validity of the contracture model.

In contrast to the surgical control, the IAM group lacked any apparent adhesions (FIG. 6, Panel III under Panel A). The synovial membrane and articular cartilage surfaces remained separate from one another. Proper cellular organization of these membranes, analogous to the healthy control, was observed. The amount of surrounding loose connective tissue appeared to be reduced when compared to the tissue found in the healthy control group. All the histologic slices in IAM also displayed both superficial and deep fibrillation within the articular surface, which was not observed in the healthy control. These changes in articular cartilage quality in the IAM group are mild, and show at least between a grade 1 and grade 2 level of osteoarthritis based on the OARSI grading system as defined by Pritzker et. al. (Pritzker et al., Osteoarthritis Cartilage, 2006, 14(1): 13-29; Glasson et al., Osteoarthritis Cartilage, 2010, 18 Suppl 3:S17-23).

Slices stained for fibronectin showed an increase in fibrotic tissue and capsular tissue thickness in the contracted surgical control when compared to the healthy control (FIG. 6, Panel II as compared to Panel I under Panel B). Additionally, evidence of adipocyte infiltration was also observed inferiorly within this tissue. These characteristics mimic those found by Kim et. al (Kim et al., J. Orthop. Surg. Res., 2016, 11(1):160). The IAM group displayed a return to normal thickness in capsular tissue as well as a reduction in peroxidase intensity in and around the capsular tissue (FIG. 6, Panel III under Panel B).

DISCUSSION

Initial evaluation of the extent of arthrofibrotic contracture induced experimentally shows no significant difference between groups, suggesting that induced contracture was similar across groups. Additionally, the control group remained restricted by −14.88% from their baseline ROM measurements after 8 weeks. This degree of constriction remains consistent with previous models and provides evidence of contracture (Kanno et al., J. Shoulder Elbow Surg., 2010, 19(5):700-8; Villa-Camacho et al., *Shoulder Elbow Surg.*, 2015, 24(11):1809-16; Kim et al., *J. Orthop. Surg. Res.*, 2016, 11(1):160). Upon examination of the other groups, the IAM treated group showed significant improvement when compared to the surgical control and was statistically similar to the baseline measurements. In fact, some IAM rats displayed improved ROMs beyond that of their initial baseline. Further evidence for this improvement is found in the torque vs. angle plot (FIG. 5, Panel D), where the IAM group's torque per angle profile closely mimics that of the baseline measurements. This close similarity may suggest not only a recovery to normal baseline ROM, but a potential return to biomechanical normalcy within the joint. These results show a distinct difference in the IAM group, demonstrating an improvement due to multiple intra-articular injections of relaxin. Non-significant changes in contralateral ROM also ensure that no systemic joint laxity was present.

The other groups showed no such improvement, suggesting that neither a single intra-articular dose nor intravenous administration of relaxin improved this model of arthrofibrosis within the shoulder. The result for the IVM group may be explained by the fact that the half-life of systemic relaxin is short, and also by the fact that a systemic administration would result in dose dilution at the shoulder. Thus, a minimal effect of relaxin on the joint when delivered systemically is not surprising. Interestingly, for the IAS group, although an improvement was not noticed after 8 weeks of measurement, there was a significant improvement over the control during the second measurement. It is possible that a single injection of intra-articular relaxin provided a transient improvement.

The histologic results further validate a role for relaxin in improving arthrofibrosis. In the H&E images, the fibrotic adhesions observed in the surgical control group within the joint space were no longer evident in the IAM treated groups. Cellular organization along the capsular surface also returned to a familiar tangential orientation that was lacking from the surgical control, suggesting a potential remission of the induced fibrosis. One finding that differed between the IAM treated group and the healthy control group was the presence of cellular fibrillation found in the articular cartilage in the IAM treated group. With at least a grade 1 on OARSI grading system, this points to potential cartilage degradation due to relaxin. An explanation for this could be related to relaxin's mechanism of action on collagens I, III, and partially II (Dehghan et al., *Scand. J. Med. Sci. Sports*, 2014, 24(4):e220-9). The doses of relaxin used in this study may possibly have resulted in an excess of collagen reuptake, resulting in a reduced capsular thickness and mild weakened collagen integrity. Thus, proper dosing of relaxin may be needed to prevent excessive collagen degradation. The fibronectin stains better illustrated the expected capsular thickening in the axillary pouch. This thickening and adipocyte infiltration in and around the capsular tissue mirrors findings by Kim et. al. and supports a valid contracture model. However, the lack of capsular thickening and adipocyte infiltration within the IAM group further shows a return to a normal condition. Despite this, the capsular tissue in the IAM group remained more densely packed with less infoldings when compared to the healthy control. This may suggest that while excess fibrosis was no longer present, the capsular tissue remains less compliant than in a healthy shoulder. As these slices were obtained at the end of an 8-week measurement period, as well as after a full 8 weeks of immobilization, acute markers would likely not remain.

In summary, this study demonstrates that the intra-articular administration of relaxin could be used to alleviate the symptoms of arthrofibrosis in a rat shoulder contracture model. Not only does the biomechanical data show a complete return to healthy baseline when multiple intra-articular injections of relaxin are performed, histologic evidence also suggests a return to healthy capsular structure.

Example 3. Preparation of Sustained-Release Formulation Comprising Relaxin

The purpose of this experiment was to prepare and evaluate a sustained release formulation (depot) capable of delivering PEGylated relaxin in vivo. The sustained release formulation was prepared by forming a hydrogel via a reaction of relaxin and a PEG cross-linker.

Synthesis of a PEG Cross-Linker

Figure 7:
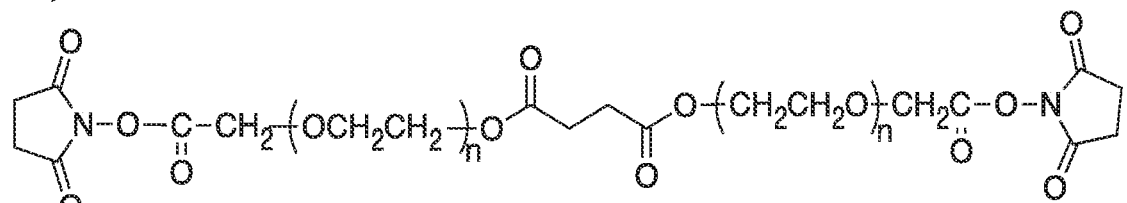
FIG. 7, Panels A, B, C, D and E show chemical structures of various PEG cross-linkers that may be used to prepare a hydrogel for delivering PEGylated polypeptides.
Figure 7:
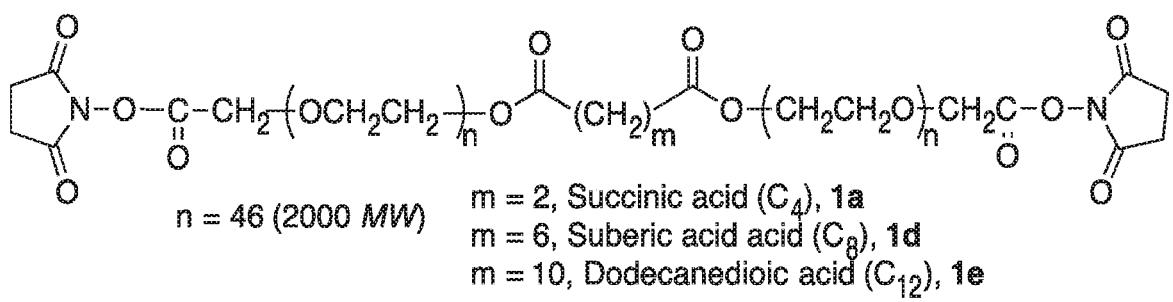
Figure 7:
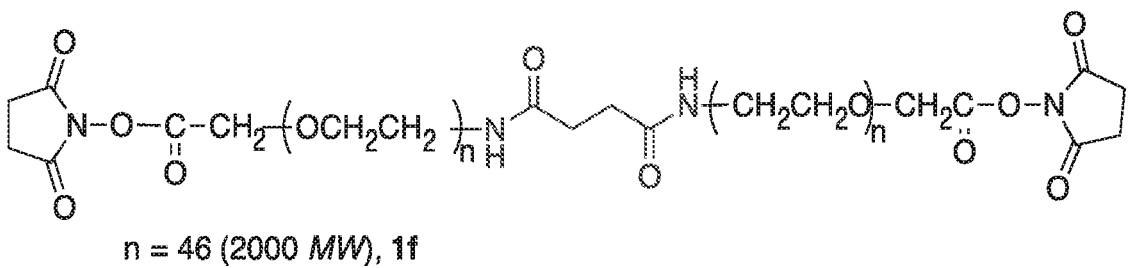
Figure 8:
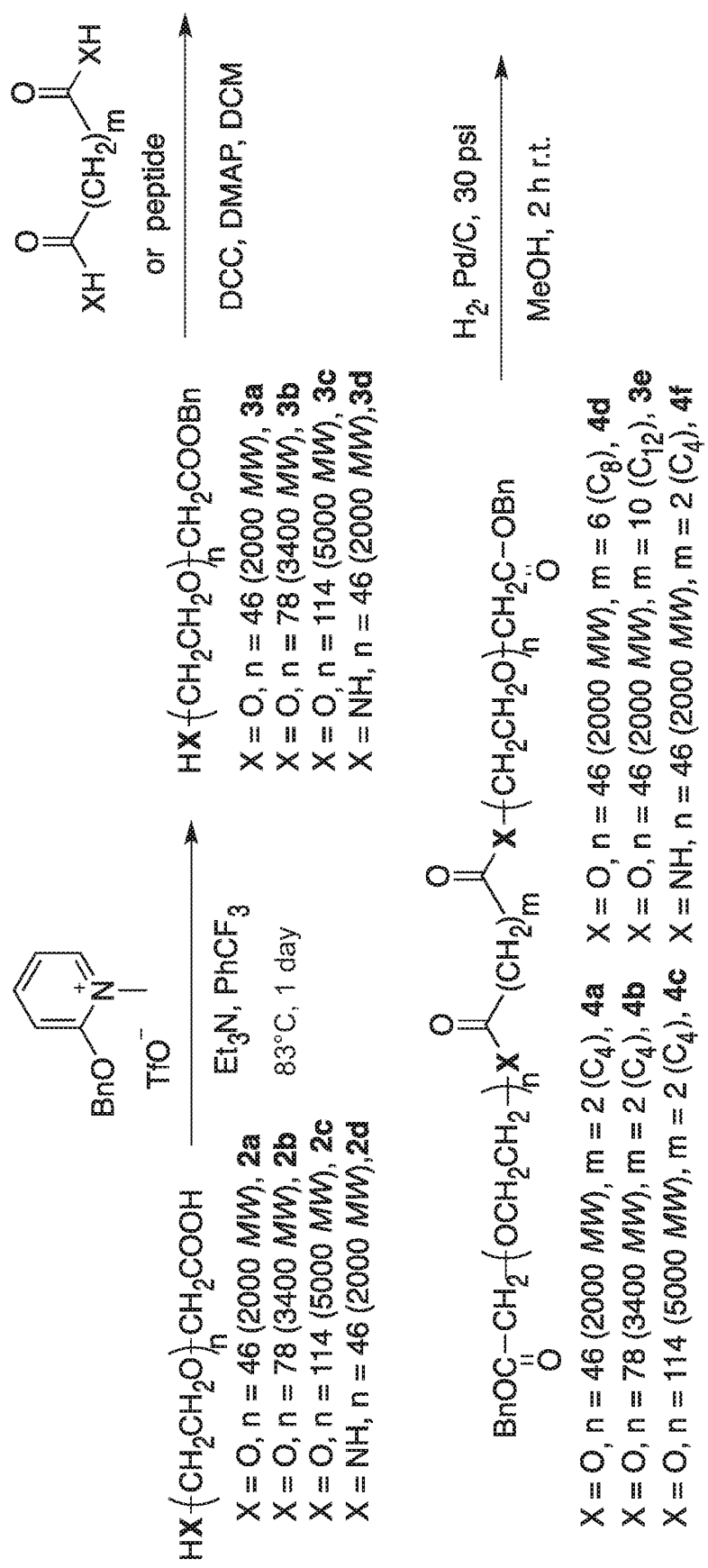
FIG. 8 is a chemical scheme illustrating synthesis of various PEG cross-linkers.
Figure 8:
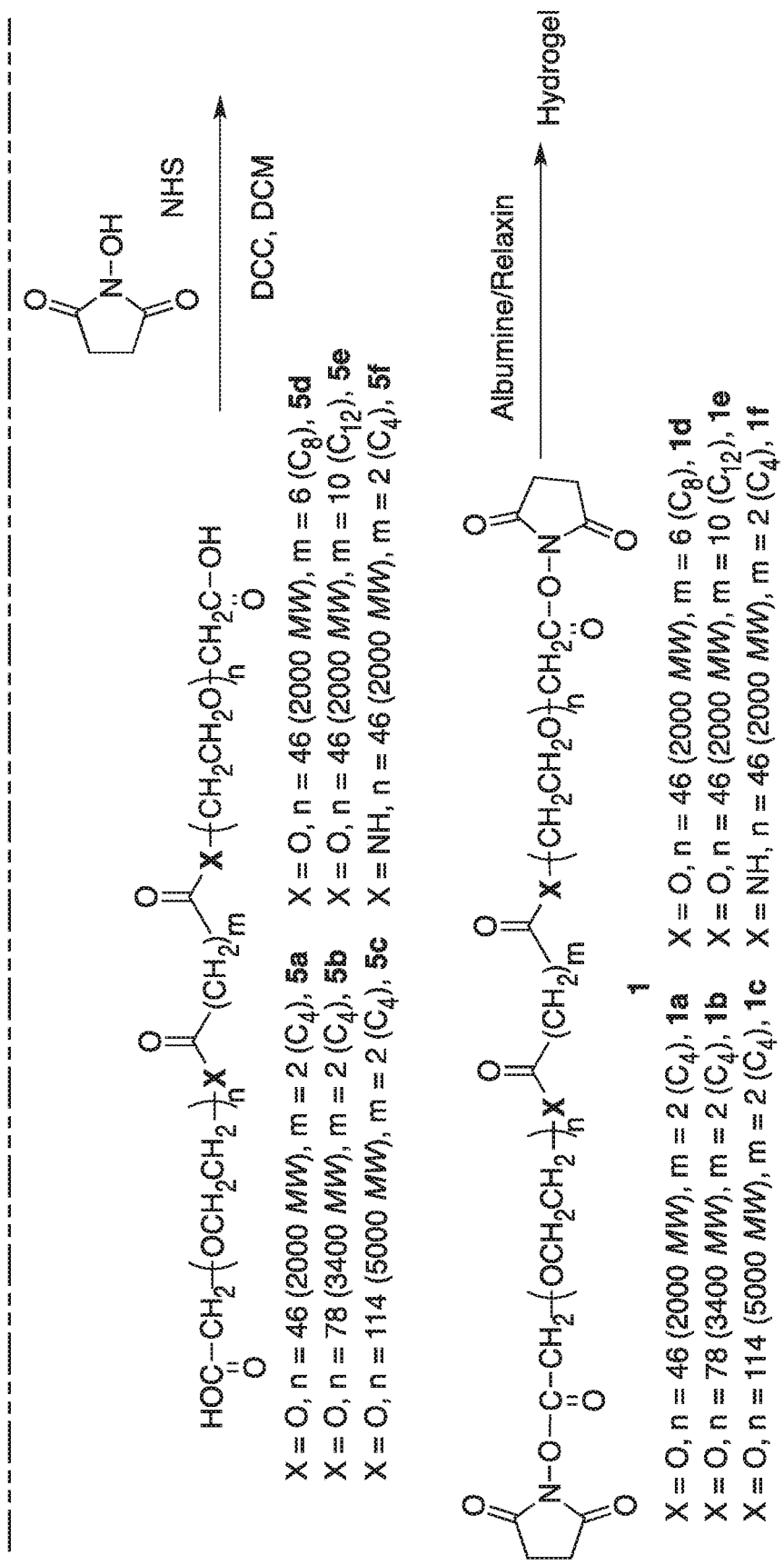

As the first step, a cross-linker 1b as shown in FIG. 7 was synthesized according to the synthesis procedure shown in FIG. 8. In the first step, the carboxyl group of HO-PEG-carboxymethyl 2b (3400 g/mol) was selectively protected using benzyl group and leaving the hydroxyl functionality intact. This was accomplished by heating 2b with 2-benzyloxy-1-methylpyridinium triflate and triethylamine in $\alpha,\alpha,\alpha$-trifluorotoluene ($PhCF_3$) at 83° C. for 1 day. The reaction mixture was cooled to room temperature and then partitioned between water and dichloromethane. The organic phase was washed with water and brine, dried ($Na_2SO_4$), filtered, and concentrated under a vacuum. The crude reaction mixture was dissolved in a minimum quantity of dichloromethane, precipitated in diethyl ether dropwise, filtered and washed with diethyl ether to yield benzyl ester 3b as a white powder (91% yield). HO-PEG-benzyl ester 3b was coupled with succinic acid (SA) (3b:SA=2:1) in the presence of N,N'-dicyclohexylcarbodiimide (DCC). The byproduct N,N'-dicyclohexylurea (DCU) was removed by syringe driven filtration (0.45 µm). The coupling product SA(PEG-benzyl ester)$_2$ 4b was obtained as a white powder (84% yield). The benzyl groups of 4b were removed by hydrogenolysis in the presence of Pd/C catalyst at 25-30 psi for 2 hours to yield the dicarboxylic acid derivative SA(PEG-$CH_2$—COOH)$_2$ 5b as a white powder (83% yield). The dicarboxylic acid derivative SA(PEG-$CH_2$—COOH)$_2$ 5b was coupled with N-hydroxysuccinimide (NHS) in the presence of DCC to yield the NHS ester derivative 1b (crosslinker) as a white powder. The crosslinker 1b is moisture sensitive. In each step, the product was isolated and purified from the reaction mixture by precipitation(s) in ether. All the compounds were characterized by $^1$H NMR spectroscopy (by matching the integration of end group functionality with other key groups present in the chain).

Preparation of the Relaxin Hydrogel Depot

Figure 9:
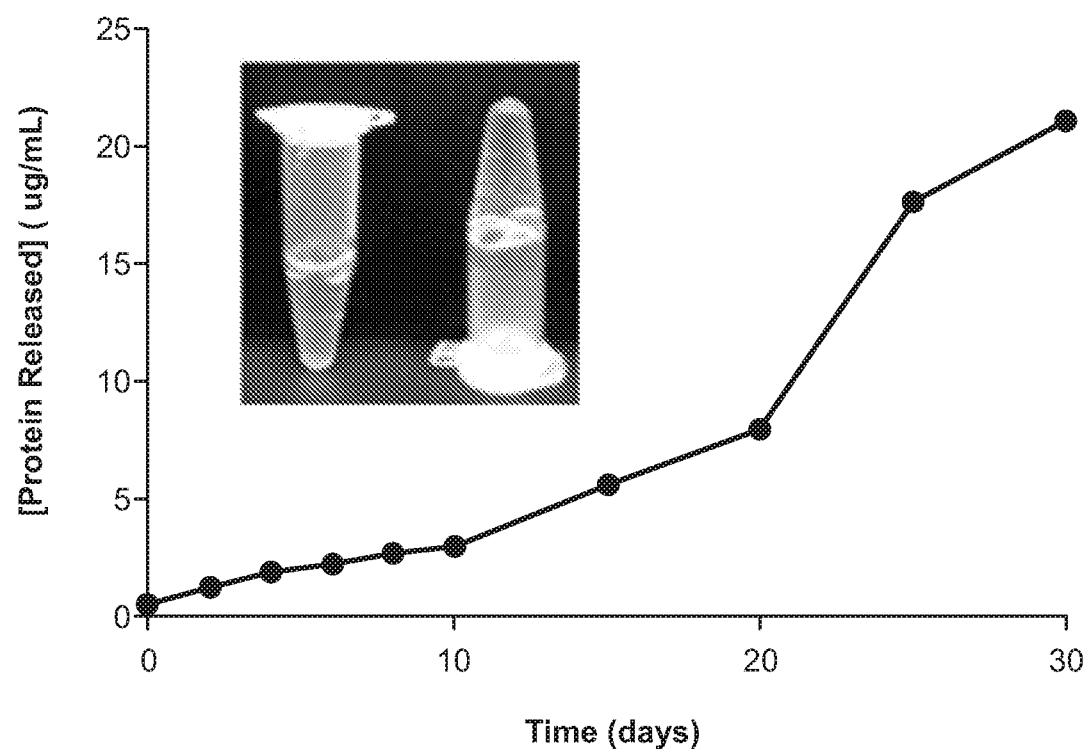
FIG. 9 is a graph illustrating release of PEGylated relaxin from the hydrogel of the invention over time. Inset in FIG. 9 is a photograph of tubes containing the hydrogel of the invention.

A hydrogel depot was prepared by mixing a solution of albumin and relaxin (ratio of 40 mg:0.1 mg albumin:relaxin) in borate buffer (0.1 M, pH 8.6, 200 µL) with the NHS activated PEG crosslinker in PBS buffer (10 mM, pH 6.5., 20 mg/200 µL). The total protein $NH_2$/crosslinker NHS equivalent molar ratio was 10:1. The total concentration of polymer in solution was 15 wt %, and albumin was used as a filler protein for easier handling and because only small quantities of relaxin were needed for subsequent assays. Gel formation was observed within 1-2 minutes, and was complete in 15 minutes, resulting in a transparent gel (FIG. 9, inset). The relaxin released from the hydrogel depot is PEGylated at its two lysine residues. The PEGylated relaxin was detected using an ELISA assay (Quantikine® ELISA, R&D Systems, Minneapolis, Minn., USA), and its release from the hydrogel into its surroundings was observed for more than 30 days (FIG. 9).

PEGylated Relaxin is Recognized by Relaxin Antibody

Figure 10:
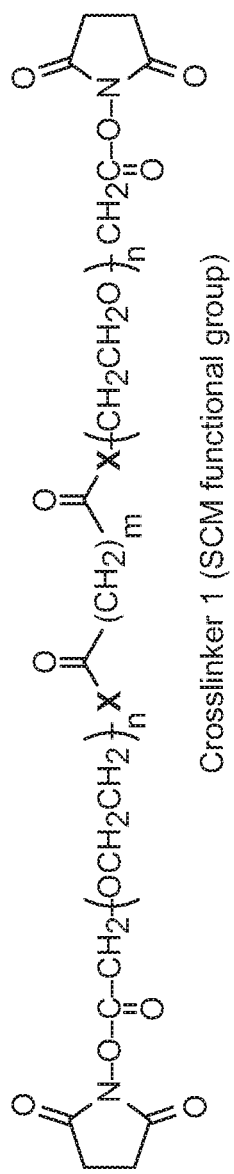
FIG. 10 shows the chemical structure of an alternate crosslinker (crosslinker 1') with a comparatively more stable succinimidyl valerate (SVA) functional group.
Figure 10:
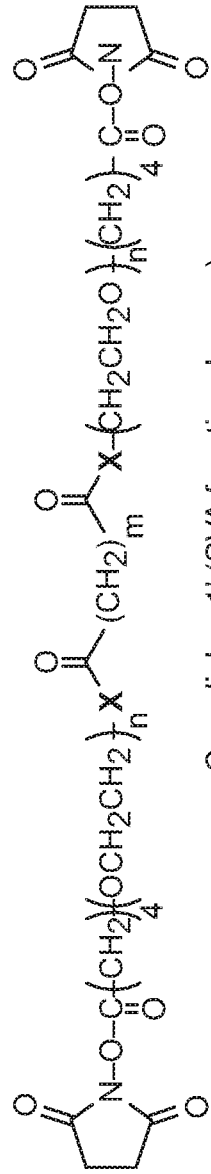
Figure 11:
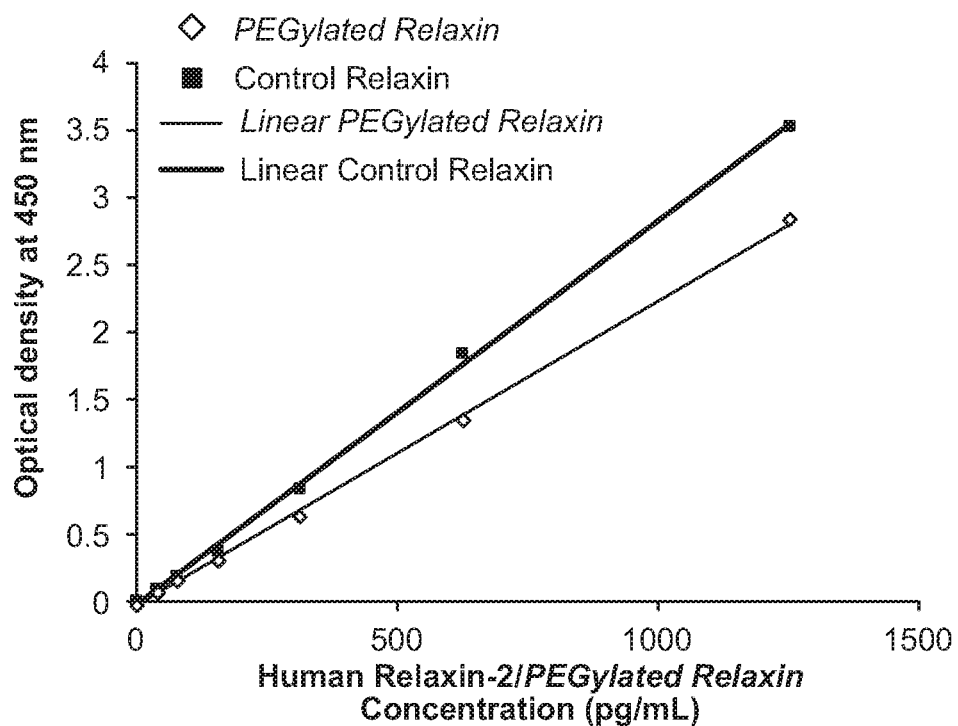
FIG. 11 is a graph illustrating the results of an ELISA assay demonstrating that PEGylated relaxin is recognized by the relaxin antibody, and that ELISA can be used to determine concentration of the PEGylated relaxin.

Because relaxin has three amino groups that can react with the PEG cross-linker, the relaxin may become PEGylated at three different sites. The purpose of this experiment was to determine if PEGylated relaxin would be recognized by the relaxin antibody. To this end, PEGylated relaxin was prepared by reacting relaxin with an NHS-PEG-OMe (methoxy poly(ethylene glycol) succinimidyl valerate (mPEG-SVA, 2000 MW) in borate buffer (0.1 M, pH 8.6), followed by dialysis purification. The structure of the mPEG-SVA linker is shown in FIG. 10. MALDI mass spectrometry data was consistent with a relaxin product conjugated with two PEG chains. Following the manufacturer's protocol, an antibody-based ELISA experiment was performed with six different dilutions of relaxin and PEGylated relaxin (Quantikine® ELISA, R&D systems, Minneapolis, Minn.). FIG. 11 demonstrates that PEGylated relaxin is recognized by the relaxin antibody, and that ELISA can be used to determine concentration of the PEGylated relaxin. The biological activity of the PEGylated relaxin is then tested in an in vitro fibroblast collagen assay.

Verification of Relaxin In Vitro Activity

Figure 12:
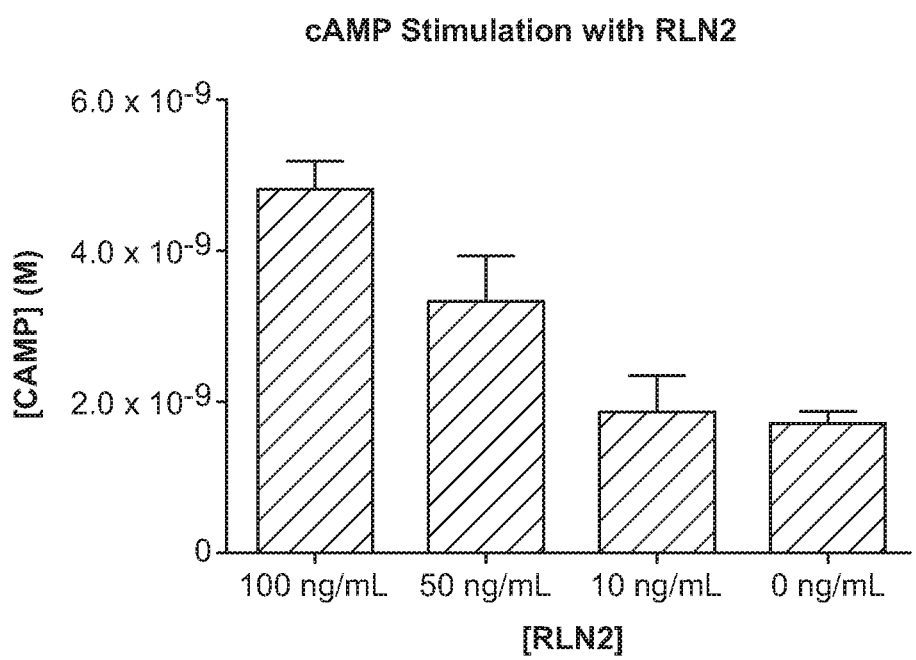
FIG. 12 is a bar graph illustrating cAMP levels in cultured NIH 373 murine fibroblasts exposed to relaxin.

The activity of recombinant relaxin (RLN2) was validated by measuring upregulation in the production of cAMP, a secondary metabolite of the relaxin signaling pathway. Increases in cAMP lead to increased MMP expression and decreased collagen and TIMP expression. To validate the activity of RLN2, cultured NIH 373 murine fibroblasts were exposed to relaxin, and the resulting cAMP levels were measured. The results are shown in FIG. 12 and demonstrate a dose-dependent upregulation of cAMP levels caused by the exposure of NIH 373 fibroblasts to relaxin.

Hydrogel Release Profile

Figure 13:
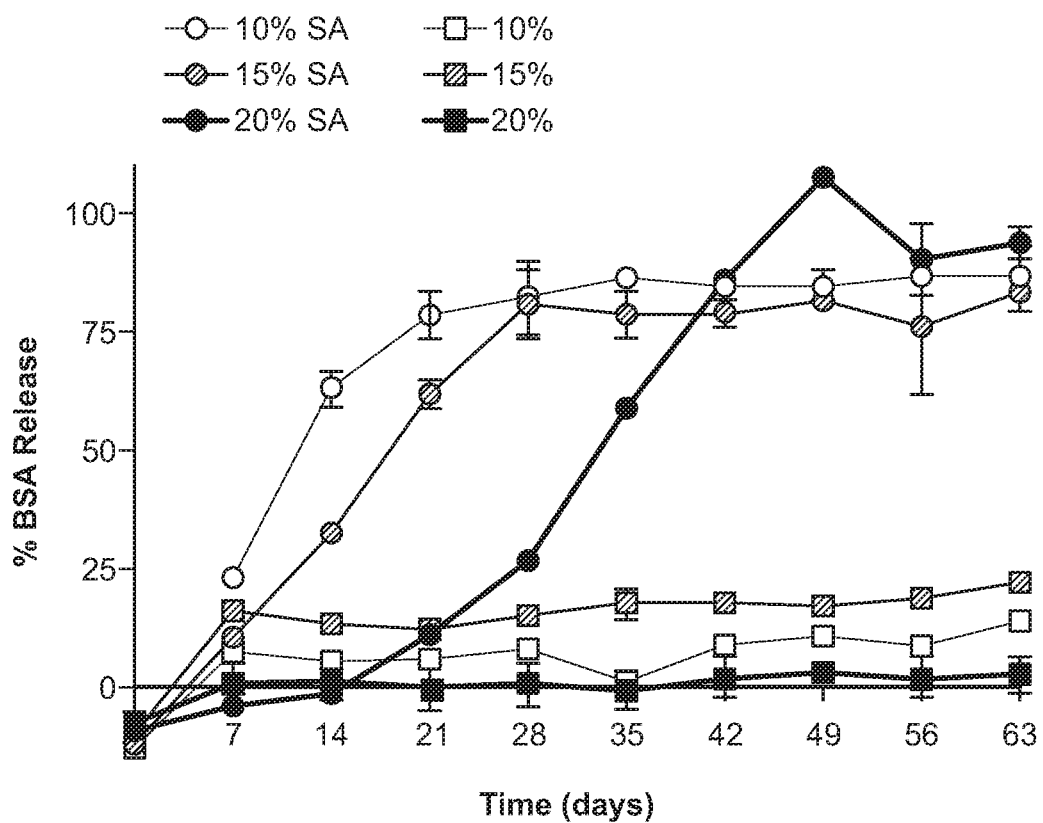
FIG. 13 is a graph illustrating time dependent release of BSA from hydrogels prepared with BSA using hydrolysable (circles) or non-hydrolysable (squares) linkers at different total concentrations of the polymer (BSA and linkers).

Six hydrogels were prepared with bovine serum albumin (BSA) as a dendrimer and a PEG-based crosslinker. Three hydrolysable gels were formed with a succinimidyl valerate-PEG-succinic acid-PEG-succinimidyl valerate crosslinker (SVA-PEG-SA-PEG-SVA, MW 7,000 Da) at 10%, 15% and 20% w/v weight of the polymer (BSA and cross-linker) per the total weight of the material in the hydrogel. Three non-hydrolysable gels of the same w/v % were created using a succinimidyl valerate-PEG-succinimidyl valerate (SVA-PEG-SVA, MW 5,000 Da) crosslinker. All gels were formed with 1:1 equivalents of free amines to SVA groups. For gelation, BSA was dissolved in 100 mM borate buffer pH 8.6, and crosslinker was dissolved in 10 mM phosphate buffer pH 6.5. Crosslinker was added to BSA solution and incubated at room temperature for one hour to ensure complete gelation. Each hydrogel was placed in 20 mL sterile PBS pH 7.4 with gentle orbital shaking (50 rpm) at 37° C. for nine weeks. Aliquots of 500 µL were removed weekly. BSA content was determined by Bradford assay using a BSA standard curve. Hydrolysable gels (FIG. 13, circles, SA) show a release profile that is dependent on gel wt %; with increasing wt % correlating with longer time for full BSA release of each SA gel. Non-hydrolysable gels (FIG. 13, squares) show limited (<25%) release of BSA. This is because in the non-hydrolysable gels BSA is permanently crosslinked into the hydrogel matrix, releasing only entrapped unlinked BSA.

Example 4. Comparison of Single Dose and Repeated Intra-Articular Administration of Relaxin The purpose of this study is to further demonstrate in a larger study that repeated intra-articular administration of relaxin reduces shoulder contracture as compared to a single-dose administration of relaxin and to controls, as reflected by increased glenohumeral ROM. The purpose of this study is also to demonstrate that increases in glenohumeral ROM are due to a greater expression of metalloproteinases (MMPs), leading to decreases in the deposition of synovial collagen III in the relaxin treated groups.

Study Design

The design of the study is shown in Table 2 below.

TABLE 2

Study Design with Sprague Dawley Rats.

| Group (n = 40) | Procedure | Treatment | Regimen | Rte/Dose (100 µL) | Expected Result |
|---|---|---|---|---|---|
| 1 | Shoulder fixation | Free relaxin | Single dose | IA/0.0005 mg | Repeated intra-articular administration of relaxin will be more effective than single-dose relaxin and controls. Minimum concentration of relaxin identified to restore ROM with no significant shoulder contracture as measured by histology. |
| 2 | Shoulder fixation | Free relaxin | Single dose | IA/0.0025 mg | |
| 3 | Shoulder fixation | Free relaxin | Single dose | IA/0.0050 mg | |
| 4 | Shoulder fixation | Free relaxin | Multiple dose | IA/0.0005 mg | |
| 5 | Shoulder fixation | Free relaxin | Multiple dose | IA/0.0001 mg | |
| 6 | Shoulder fixation | Free relaxin | Multiple dose | IA/0.00005 mg | |
| 7 | Shoulder fixation | Saline | Multiple dose | — | |
| 8 | Sham | Saline | Multiple dose | — | |

The rats will be sacrificed at 0, 2, 4 and 8 weeks for analyses. Intra-articular (IA); route of administration (Rte).

As shown in Table 2, the study includes six experimental and two control groups for a total of 320 adult Sprague Dawley rats. Each experimental group includes 40 rats, and 10 rats are sacrificed at each of the four time points (0, 2, 4, and 8 weeks) for analyses. Torque is measured per degree on both shoulders of each animal as a function of rotation angle between 100° of internal rotation and 60° of external rotation prior to any surgical intervention (baseline). Rotation is confined within boundaries that have been observed to elicit minimal scapular recruitment. Torque values at 60° external rotation ($\tau_{OUT}$) and 100° of internal rotation ($\tau_{INT}$) are recorded for each animal.

After baseline measurements, 280 animals are subjected to randomly selected forelimb immobilization. Anesthesia is induced with 5% isoflurane inhalation and then maintained with 2% isoflurane via nose cone. A longitudinal skin incision is made perpendicular to the scapular spine. Two No. 2-0 braided polyester sutures (Ethibond Excel, Ethicon—San Lorenzo, PR) are passed between the medial border of the scapula and the humeral shaft and tightened to immobilize the shoulder joint. Muscular structures are not be manipulated during this procedure. An additional group of 40 animals is to undergo sham surgery (incision only) to serve as negative controls (Group 8, Table 2). The animals are allowed to have unrestricted movement in their cages after each surgical procedure.

The restraining sutures are removed after 8 weeks, followed by post-immobilization unrestricted movement in their cages. The animals are subsequently divided in eight groups (Table 2). The first three groups (40 rats each) receive a single dose of intra-articular recombinant human relaxin-2 at a single dose of 0.0005 mg, 0.0025 mg or 0.0050 mg, respectively, diluted in 100 µL of PBS. The intra-articular injection is performed on anesthetized animals under fluoroscopic guidance immediately after suture removal. Human recombinant relaxin has been shown to successfully treat several in-vivo rodent models of fibrosis (Samuel C. S. et al., *Endocrinology* 2004, 145(9):4125-33; Lekgabe E. D. et al., *Hypertension* 2005, 46(2):412-8; Samuel C. S. et al., *Kidney International,* 2004, 65(6):2054-64; Williams E. J. et al., *Gut,* 2001, 49(4):577-83; Moren-Hybbinette I. et al., *Acta Medica Scandinavica,* 1987, 221(1):73-82; Reeves B., *Scandinavian Journal of Rheumatology,* 1975, 4(4):193-6.). The results described in Example 2 demonstrate that relaxin effectively improves the ROM of rats with shoulder contracture. The doses for the intra-articular administration of relaxin are based on the range of peripheral concentration levels of relaxin in pregnant rats (0.00005 mg/mL at day 14 of pregnancy to approximately 0.0002 mg/mL at parturition) (Sherwood O.D., *Endocr Rev.,* 2004, 25(2):205-34; Sherwood O.D. et al., *Endocrinology,* 1980, 107(3):691-8), and the results described in Example 2 demonstrating that a single intra-articular injection of relaxin at 0.00050 mg was ineffective, but 5 doses of 0.0005 over 10 days were effective in treating shoulder contracture. The next three groups 4-6 consisting of 40 rats each, receive a total of 5 doses of intra-articular recombinant human relaxin at a dose of 0.0005 mg, 0.0001 mg or 0.00005 mg, respectively, diluted in 100 µL of PBS. In these groups, the injections are performed on anesthetized animals under fluoroscopic guidance every 48 hours during the first 10 days of the post-immobilization period. The final two groups, with 40 rats each, serve as positive and negative controls.

Glenohumeral ROM Measurements

ROM and torque measurements are performed under general anesthesia as described in Example 2. The effects of relaxin administration are measured at four time points in the post-immobilization period: at baseline (week 0, immediately after the removal of the restraining sutures), and at 2, 4 and 8 weeks following immobilization. Changes in kinematics are longitudinally quantified in the follow-up period by measuring the ROM achieved with the $\tau_{OUT}$ and $\tau_{INT}$ measured at baseline. The measurements for the contralateral shoulder are used as internal controls in order to reduce the total number of animals necessary to conduct the study.

Quantification of MMP and TIMP and Relaxin Concentration in the Synovial Space

Ten animals from each group are euthanized at each time point via $CO_2$ inhalation (Table 2). The glenohumeral joint space is bilaterally perfused with 150 µL of sterile saline using a standard procedure (Barton N. J. et al., *Journal of Inflammation* (London, England), 2007, 4:13). Briefly, two 30 G needles are inserted into the joint space with fluoroscopic guidance. A peristaltic pump is connected to one of the needles, and sterile saline is infused at a constant rate of 100 l/min. The infused fluid is withdrawn through the remaining needle and the samples are immediately frozen at −20 OC. Levels of MMP-9, MMP-14, TIMP-1 and relaxin in the samples are measured using commercial ELISA kits (Barton N. J. et al., *Journal of Inflammation* (London, England), 2007, 4:13).

Quantification of Capsular Morphological Changes

After perfusion, both shoulders (immobilized and contralateral) are harvested and fixed in 10% formalin for 18 hours at 4° C. Specimens is decalcified with 10% ethylenediamine tetraacetic acid for 8 weeks. After decalcification, the specimens is embedded in paraffin, and 2 m sections are obtained and stained with hematoxylin-eosin (Kanno A. et al., *Journal of Shoulder and Elbow Surgery,* 2010, 19(5): 700-8). Histologic sections are magnified by an optical microscope, viewed by a solid-state camera, and captured with a frame grabber (Trudel G. et al., *Arch Phys Med Rehabil.,* 2003, 84(9):1350-6; Trudel G et al., *J. Rheumatol.,* 2000, 27(2):351-7). The synovial lining contour is traced and its length measured with Image J (Schneider C. A. et al., *Nat Methods,* 2012, 9(7):671-5). The length of the synovial intima is measured from its attachment site on the humeral neck to that on the inferior edge of the glenoid, including all synovial folds.

Immunohistochemical staining using the peroxidase-antiperoxidase method is performed to assess the distribution of type III collagen in the joint (Kanno A. et al., *Journal of Shoulder and Elbow Surgery,* 2010, 19(5):700-8; Schollmeier G et al., *Clin. Orthop. Relat. Res.* 1996, (323):310-5). After removing the paraffin with xylene, the specimens are treated with methanol and 30% hydrogen peroxide for 30 minutes to block endogenous peroxidase activity. After washing, these specimens are activated with pepsin for 15 minutes. Blocking is performed with goat serum for 30 minutes, and the specimens are incubated with a mouse monoclonal antibody to type III collagen overnight at 4° C. The specimens are washed and incubated with a second antibody, goat antimouse immunoglobulin G-peroxidase conjugate for 30 minutes. The specimens are washed and exposed to 3,30-diaminobenzidine tetrahydro-chloride and 30% hydrogen peroxide in the dark for 10 minutes and counterstained with Carazzi hematoxylin.

The staining intensity for type III collagen is assessed by histomorphometric measurements. The digital images are imported into Adobe Photoshop CS2, where the region of interest typically encompasses $10^6$ pixels. The number of type III collagen positive pixels are determined using the Magic Wand tool by a single blinded investigator and confirmed by a second investigator.

Pharmacokinetic Profiling

Tail vein blood draws are performed every 72 hours during the first 10 days of the post-immobilization period to determine relaxin pharmacokinetics using a commercial ELISA kit (Human Relaxin-2 Quantikine ELISA Kit—R&D Systems, Minneapolis, Minn.).

Results

It is expected that repeated intra-articular administration of relaxin is more effective than single-dose relaxin and controls. Minimum concentration of relaxin required to restore ROM with no significant shoulder contracture is identified using histology.

Example 5. Characterization of the Release Kinetics of Relaxin from a Hydrogel Matrix The purpose of this study is to characterize a hydrogel sustained release formulation (hydrogel depot) capable for delivering relaxin. Specifically, this study is conducted in order to characterize release kinetics of relaxin from the hydrogel depot and its dependence on the cross-linker composition, relative amounts of the relaxin and the cross-linker and total polymer weight percent. It is expected that the hydrogel formation rate is dependent on pH and buffer strength; that sustained release of PEGylated relaxin is accomplished through hydrolysis of cleavable linker, such as the succinate linkage; and that the high relaxin to crosslinker ratio and increased weight % of the hydrogel components affords a slower and more sustained release of relaxin.

Hydrogel Design

The relaxin-PEG hydrogel depot is administrable via a double barrel syringe with a mixing chamber for the relaxin and PEG aqueous solutions; is injectable through a 21 G needle; gels in under 15 seconds after administration; and provides sustained-release of PEGylated relaxin over the period of six weeks at a therapeutic dose (rat physiologic range 50-200 ng/mL) (Sherwood O.D., *Endocrinology*, 1980, 107(3):691-8).

Synthesis of Cross-linkers

A small library of hydrogel depots is prepared using the methods described in Example 3, published methods, or modifications of published procedures (Ghobril C. et al., *Angew. Chem. Int. Edit.* 2013, 52(52):14070-4; Ghobril C. and Grinstaff M. W., *Chemical Society Reviews* 2015, 44(7): 1820-35; Ghobril C. et al., *Biomacromolecules* 2016, 17(4): 1235-52). One structural or compositional feature at a time is systematically varied in the subsequent preparation and characterization of the hydrogel depots (FIG. 7). Initially, the protein (relaxin or relaxin and albumin):crosslinker equivalent ratio is varied (e.g., amine to NHS ratio; 10:1; 4:1; 2:1; 1:1) using the PEG crosslinker 1b (FIG. 7). Relaxin possesses three surface amino groups while albumin has 40. The ratio of albumin to relaxin is also varied from 0:100, 5:95, 10:90, 50:50, 75:25, 90:10, and 95:5. Subsequently, the 0:100, 5:95, and 95:5 albumin:relaxin formulations is used, the amine to NHS ratio is maintained at 1:0.5 and the total polymer weight % of the hydrogel is increased from 0.1, 0.5, 1, 5, 10, 15, 25, and 50%. Next using the 0:100, 5:95, and 95:5 albumin:relaxin formulations and amine to NHS ratio of 2:1, and 15 weight % formulation, the consequences of varying the PEG molecular weight (FIG. 7, part C) of the crosslinker carrying succinic acid ($C_4$) as a spacer (hydrophobic portion) is evaluated. Also evaluated is the effect of spacer length (hydrophobic portion) of the 2000 MW PEG cross-linker (FIG. 7, part D) by increasing the number of methylene groups between the two PEG-NHS moiety. The cross-linker containing two PEG-NHS moieties coupled to succinic acid through amide linkages (FIG. 7, part E) is used as a control to prepare non-hydrolysable (by esterase at physiological condition) hydrogel.

The dioic acid moiety is introduced between two PEG chains using HX-PEG-carboxymethyl (X=O, NH) 2a-d (FIG. 8). The first step involves selective protection of the carboxyl group with a benzyl group in the presence of the hydroxyl functionality, following a previously described procedure (Tummatorn J. et al., *The Journal of Organic Chemistry* 2007, 72(23):8962-4). Specifically, 2a-d reacts chemoselectively with 2-benzyloxy-1-methylpyridinum triflate to yield the PEG benzyl esters 3a-d. Next, polymers 3a-d are coupled with the corresponding dioic acid, in the presence of N,N'-dicyclohexylcarbodiimide (DCC), to provide polymers 4a-f, which possess four ester linkage (two succinates and two benzyl ester). The next step involves chemo-selective de-protection of the benzyl ester in the presence of the other ester linkages, following hydrogenolysis using Pd/C catalyst at low pressure (25-30 psi) for 2 hours. Thus, 4a-f is chemoselectively deprotected to yield 5a-f. The last step converts the carboxylic acid to the corresponding NHS ester by coupling 5a-f with NHS in the presence DCC at room temperature to yield cross-linkers 1a-f. In each step, the product is isolated and purified from the reaction mixture by precipitation(s) in ether.

Structural Characterization of the Cross-Linkers

The cross-linkers are characterized by $^1$H and $^{13}$C NMR spectroscopy, FT-IR, GPC, and MALDI-MS. The purity is determined by HLPC.

Hydrogel Formation

To prepare the hydrogel, a solution of albumin and relaxin in borate buffer is reacted with the solution of PEG cross-linker in PBS. The initial ratio of free-$NH_2$ groups on the protein to activated NHS esters is 1:1, and the total concentration of polymer in the solution is 0.1, 0.5, 1, 5, 10, 15, 25, or 50 wt %. The pH of the borate buffer is pH 7.4, 8.6, or 9, while the pH of the PBS buffer is varied to 6, 6.5, or 7.4. The ratio of albumin to relaxin is also varied from 0, 5, 10, 50, 75 and 90%. The studies are performed using 100% relaxin hydrogels. The rate of gelation is determined by rheometry, following the published procedures (Wathier M. et al., *Journal of the American Chemical Society* 2004, 126(40): 12744-5).

Release of PEGylated Relaxin from the Hydrogel

The amount and release rate of PEGylated relaxin from the hydrogel is determined.

The relaxin loaded hydrogel depot is placed in a dialysis tubing (MWCO 50 kDa) at 37° C., and the PEGylated relaxin concentration in the surrounding aqueous solution (Dulbecco's phosphate buffered saline (PBS)/10% HSA solution (20 mL) is measured using an ELISA kit (Quantikine® ELISA, R&D systems, Minneapolis, Minn.).

Mechanical Properties of the Hydrogel

Rheological characterization of the hydrogel deport is performed as previously described (Wathier M. et al., *Journal of the American Chemical Society* 2004, 126(40):12744-5). Cylindrical hydrogel samples with a diameter of 9 mm and a thickness of 3 mm are prepared and analyzed after sitting at 25° C. for two hours. The mechanical strength and viscoelastic properties of the hydrogels is investigated using rheological measurements. First, the strain sweep test is performed at a chosen frequency (e.g., 1 Hz) to establish the range of linear viscoelasticity (LVE). Then, the frequency sweep at a constant oscillatory stress (Pa) is determined for all appropriate relaxin hydrogel candidates before and after swelling. It is expected that a suitable hydrogel depot exhibits strong elastic properties with storage moduli (G') higher than the loss moduli (G") at frequencies between 0.1 and 10 Hz. After exposure to PBS buffer at pH 7.4 for 48 hours, the hydrogels swell and their rheological measurements is investigated. It is expected that after swelling, the G' and G" values decrease due to more water embedded in the hydrogel's network.

Swelling of the Hydrogel

Swelling of the hydrogel depots is performed as previously described (Ghobril C. et al., *Angew. Chem. Int. Edit.* 2013, 52(52):14070-4). Cylindrical hydrogels (d=9 mm, h=3 mm) are immersed in 10 mL of PBS 10 mM buffer at pH 7.4 for 48 hours. The diameters, heights and weights are measured at 1, 4, 6, 12, 24, 36, and 48 hours using a digital micrometer and a milligram precision scale. The equilibrium conditions is noted (estimated to be around 12 hours), and the data from three consecutive measurements are averaged (data is expressed as mean±standard deviation (n=3)). The swelling ratio is calculated by dividing the weight of the hydrogel at equilibrium ($W_{eq}$) minus the weight just after gelation ($W_o$) by their weight just after gelation ($W_o$): $SD=(W_{eq}-W_o)/W_o \times 100\%$.

Degradation Characteristics of the Hydrogel

The degradation characteristics of the hydrogel depots are determined at 1, 3, 7, 14, 21, 30, and 42 days in serum in the presence and absence of esterase at 37° C. (SIGMA #E2884) (n=3). Hydrogel mass is measured over time, normalized to their values at time 0, and fit to a first-order exponential model to quantify time constants (t) and steady-state values (e.g., ms).

Example 6. Assessment of Local Tissue Response to Relaxin

The goal of this study is to identify and describe the local tissue response to intraarticularly administered relaxin at the injection site, as well as in other joints, primary organs, and serum. It is expected that after intraarticular administration, relaxin concentration will achieve maximum levels at the injection site in the joint, but it will show low to minimal detectable levels in primary organs and plasma due to its short half-life of about 2.5 hours. It is also expected that the histological changes observed in the joint capsule in Example 2 are due to a greater expression of MMPs, which leads to a decrease in synovial collagen I/III deposition and an increase in collagen degradation. It is also expected that the histological changes in cartilage observed in Example 2 are due to a greater expression of MMPs, which leads to a decrease in collagen II deposition and an increase in collagen degradation, as well as to the degradation of non-collagenous extracellular matrix components, such as proteoglycans.

Study Design

The design of the study is shown in Table 3 below. Each experimental group has 30 adult Sprague Dawley rats equally divided into male and female animals, where 6 rats are sacrificed at each of the five time points (0.5, 1, 4, 12 and 24 hours) for analysis. Rats are randomized following a block design method (Festing et al., *ILAR J.*, 2002, 43(4): 244-58), with each block consisting of 30 animals that are assigned at random to each of the different groups. The main objective is to compare increasing single doses of relaxin at different time intervals following initial intra-articular injection to assess potential local and systemic side effects.

TABLE 3

Study design

| Group (n = 30) | Intraarticular Single Dose (per 100 μL) | Serum Markers | Immunohistochemistry (IHC)/ Histochemistry (HC) | Expected Outcomes |
|---|---|---|---|---|
| 1 | 0.0025 mg | Relaxin Levels | Synovial Lining: | Intra-articular administration of |
| 2 | 0.005 mg | Relaxin | Relaxin | relaxin is expected to have |
| 3 | 0.025 mg | Targets: MMP | MMP-1,3 | minimal to no detectable levels in |
| 4 | 0.125 mg | 1/3/9/13 & | Collagen I/III | serum. |
| 5 | 0.625 mg | TIMP-1 | Articular Cartilage: | Increased expression of MMPs in |
|  |  | Cartilage | Relaxin | serum (and decreased TIMP-1) is |
|  |  | Metabolism: | MMP-1,3 | evidenced by histological changes |
|  |  | COMP | Collagen II | (IHC) in the synovial lining and |
|  |  |  | Aggrecan | cartilage. |
|  |  |  |  | Markers of cartilage metabolism in serum are expected to be increased, and histological changes are evidenced by IHC in such tissues. |

Each group is to receive a single dose of increasing concentrations of intra-articular recombinant human relaxin 2 diluted in 100 μL of PBS on the left shoulder joint. Since relaxin has a short half-life (about 2.5 hours), it was previously challenging to study and observe potential detrimental effects of relaxin on other tissues and organs of interest. Thus, intraarticular administration of increasing doses of relaxin allows elucidating of the local tissue response, as well biodistribution of relaxin in serum and relaxin concentration in distant joints and primary organs, such as liver, spleen and kidneys. Intra-articular injections are performed on anesthetized animals under fluoroscopic guidance.

The doses for the intra-articular administration of relaxin are determined based on the range of peripheral concentration levels of relaxin in pregnant rats (0.00005 mg/mL at day 14 of pregnancy to approximately 0.0002 mg/mL at parturition) (Sherwood et al., *Endocrinology*, 1980, 107(3), 691-8; Sherwood, *Endocr. Rev.*, 2004, 25(2):205-34). Preliminary studies described in Example 2 demonstrated single intra-articular injection of relaxin at the dose of 0.0005 mg was ineffective, while 5 doses of 0.0005 mg over 10 days (total dosage: 0.0025 mg) were effective in treating shoulder contracture. Groups 1-5 are to receive a one-time injection of intra-articular recombinant, human relaxin at the doses of 0.0025 mg, 0.005 mg, 0.025 mg, 0.125 or 0.625 mg respectively, diluted in 100 μL of PBS. Finally, after euthanasia at each time point (N=6, 3 females and 3 males), the injected shoulder is harvested, as well as the contralateral shoulder, serving as its own control for histological assessment. Moreover, primary organs such as liver, spleen and kidneys are harvested and, after sample preparation, tissue extracts are subjected to ELISA to determine the concentration of relaxin.

Quantification of Capsular Morphological Changes

After perfusion, both shoulders (injected and contralateral) are harvested and fixed in 10% formalin for 18 hours at 4° C. Specimens are decalcified with 10% ethylenediamine tetraacetic acid (EDTA) for 8 weeks. After decalcification, the specimens are embedded in paraffin, and 2 pm sections are stained with hematoxylin-eosin (Kanno et al., *J. Shoulder Elbow Surg.*, 2010, 19(5):700-8). Histologic sections are magnified by an optical microscope, viewed by a solid-state camera, and captured with a frame grabber (Trudel et al., *Arch. Phys. Med. Rehabil.*, 2003, 84(9):1350-6; Trudel et al., *J. Rheumatol.*, 2000, 27(2):351-7). A combination of collagens I/II/III, MMP-1/3/13, and Aggrecan are used to histologically qualify joint health.

Quantification of local relaxin present in the synovial lining and cartilage is performed through immunohistochemistry as described by Sokol et al. (Sokol et al., *Histochemistry & Cytochemistry*, 1989, 37(8):1253-5). Immunohistochemical staining using the peroxidase-anti-peroxidase method is performed to assess the distribution of collagen types I, II and III (Kanno et al., *J. Shoulder Elbow Surg.*, 2010, 19(5):700-8; Schollmeier et al., *Clin. Orthop. Relat. Res.*, 1996, 323:310-5). After deparaffinizatin, the specimens are treated with methanol and 30% hydrogen peroxide for 30 minutes to block endogenous peroxidase activity. After washing, these specimens are activated with pepsin for 15 minutes. Antigen retrieval is be performed in this step for collagen I staining (see below). Blocking is performed with goat serum for 30 minutes, and the specimens are incubated with a mouse mono-clonal antibody to types I/II/III collagen overnight at 4° C. The specimens are washed and incubated with a second antibody, goat antimouse IgG-peroxidase conjugate for 30 minutes. The specimens are washed and exposed to 3,30-diaminobenzidine tetrahydro-chloride and 30% hydrogen peroxide in the dark for 10 minutes and counterstained with hematoxylin. Antigen retrieval for collagen I staining is performed before the blocking step with goat serum, by microwave irradiation, with sodium citrate buffer solution.

MMP staining is performed to assess the presence and distribution of MMP-1 and 3 in the synovial lining and the articular cartilage. MMP immunohistochemistry is performed as previously described by Clifton et al. (Clifton et al., *J. Orthop. Res.*, 2014, 32(8):1061-7). Moreover, as a secondary assessment of the cartilage microstructure, Aggrecan staining by IHC and histomorphometry is performed as described by Zhang et al. (Zhang et al., *J. Anat.*, 2004, 205(3):229-37). This is the most abundant proteoglycan in the articular cartilage, and a vulnerable ECM component to digestion by MMPs. The staining intensity for collagen I/II/III, MMP-1/3, and Aggrecan is assessed by histomorphometric measurements. The digital images are analyzed with ImageJ for a region of interest that typically encompasses $10^6$ pixels.

Pharmacokinetic Profiling

Tail vein blood draws are obtained at each time point until euthanasia to determine human relaxin pharmacokinetics using a commercial ELISA kit (Human Relaxin-2 Quantikine ELISA Kit—R&D Systems, Minneapolis, Minn.). MMP 1/3/9/13 and TIMP-1 are also quantified by ELISA as described by Anumba et al (Anumba et al., *Reprod. Biol. Endocrinol.* 2010, 8:62). Cartilage Oligomeric Matrix Protein (COMP) is an ECM glycoprotein considered a marker of cartilage breakdown (Tseng et al., *Biomark. Insights*, 2009, 4:33-44). In order to assess relaxin's potential effect on articular cartilage, COMP levels in serum will be determined by a quantitative Sandwich ELISA kit (Yamanokuchi et al., *Equine Vet. J.*, 2009, 41(1):41-6).

Collagenase Activity

Collagenases are members of the zinc metalloproteases (MMPs) that degrade the collagen and other components of the extracellular matrix (ECM). Collagenase-1 (MMP1) is involved in the breakdown of collagen type I and III. Moreover, collagenase 1 (MMP-1) and collagenase 3 (MMP13) appear to be involved in the breakdown of type II collagen in the articular cartilage (Wu et al., *Arthritis Rheum.*, 2002, 46(8):2087-94; Chung et al., *EMBO J.*, 2004, 23(15):3020-30). As MMPs are upregulated by relaxin endogenously, collagenase assays are performed to track MMP-1 and MMP-13 activity against collagen fibrils in the synovial lining and articular cartilage, as described by Naqvi et al. (Naqvi et al., *Arthritis Res. Ther.*, 2005, 7(1):R1-11). Fluorescence intensity of degraded collagen products is determined with a microplate spectrofluorometer.

Example 7. Efficacy and Pharmacokinetics of Relaxin Hydrogel in a Rat Model of Shoulder Contracture The goal of this study is to evaluate the efficacy and the pharmacokinetic parameters of the relaxin hydrogels prepared in Example 5 in a rat model of shoulder contracture. It is expected that a relaxin hydrogel formulation exhibits a better pharmacokinetic profile than free relaxin, as demonstrated by faster accrual of steady-state kinetics in the synovial fluid and lower systemic concentrations of the proteins. It is also expected that a relaxin hydrogel formulation is at least as efficacious as repeated injections of free relaxin, as reflected by total glenohumeral ROM, thus obviating the need for repetitive administration.

Study Design

The design of the study is shown in Table 4 below.

TABLE 4

Study Design with Sprague Dawley Rats.

| Group (n = 40) | Procedure | Treatment | Regimen | Rte/Dose (100 uL) | Expected Outcome |
|---|---|---|---|---|---|
| 1 | Sham | Saline | Single dose | — | Untreated negative control. No Loss of ROM as measured by kinematics and no significant shoulder contracture as measured by histology |
| 2 | Shoulder fixation | Saline | Single dose | — | Positive control. Loss of ROM as measured by kinematics and significant shoulder contracture as measured by histology, results similar to preliminary data section 3 positive controls |
| 3 | Shoulder fixation | Relaxin-HD | Single dose | IA/ 0.0025 | Return of full ROM, no significant shoulder contracture via histological analysis, similar to sham negative control |
| 4 | Shoulder fixation | Relaxin-HD | Single dose | IA/ 0.0025 | Return of full ROM, no significant shoulder contracture, similar to sham negative control |
| 5 | Shoulder fixation | Relaxin-HD | Single dose | IA/ 0.0025 | Return of full ROM, no significant shoulder contracture similar, to sham negative control |
| 6 | Shoulder fixation | Free relaxin | Single dose | IA/ 0.0025 | Loss of ROM as measured by kinematics and significant shoulder contracture as measured by histology, similar to positive control, dose and duration of relain inadequate |
| 7 | Shoulder fixation | Free relaxin | Multiple dose | IA/ 0.00025 mg | Daily injections for 10 days. Return of full ROM, no significant shoulder contracture, similar to sham control. Increased inflammation at the joint due to repeated injections. Pharmokinetics profile similar to the hydrogel depot group |

The rats are sacrificed at 0, 2, 4 and 8 weeks for analyses. Relaxin Hydrogel Depot (relaxin-HD); Intra-articular (IA); route of administration (Rte).

The study design, outlined in Table 4, includes five experimental and two control groups for a total of 280 animals. Each experimental group includes 40 adult Sprague Dawley rats (10 rats sacrificed at each of four time points, i.e., 0, 2, 4, and 8 weeks) for analyses. The procedure mirrors that described in Examples 2 and 4. The animals are allowed to have unrestricted movement in their cages after each surgical procedure.

The restraining sutures are removed after 8 weeks of immobilization. The animals are subsequently divided in seven groups (Table 2, N=40/group). Groups 1 and 2 are the negative (sham) and positive control groups, respectively. The treatment three groups receive a single dose of intra-articular recombinant human relaxin 2 delivered in a hydrogel matrix (the concentration of relaxin within the matrix is determined based on the results obtained in Examples 4 and 5). Based on the currently available data, 0.0025 mg of relaxin are delivered using the hydrogel depot because the results in Example 2 demonstrated that five IA injections of 0.0005 mg over 10 days provided full recovery with increased ROM for 60 days. Hydrogel injection is carried out with double-barreled syringes specifically designed by Accuro Technologies for synovial joint injections (one barrel relaxin and the other PEG crosslinker). Groups 6 and 7 are used to assess the effect of a single dose at 0.0025 mg and the response to the same total dose administered over 10 days via daily IA injections of 0.00025 mg per dose. The IA injections are performed on anesthetized animals under fluoroscopic guidance immediately after suture removal.

Quantification of MMP and TIMP and Relaxin Concentration in the Synovial Space

Ten animals from each group are euthanized at each time point via $CO_2$ inhalation (Table 2). Synovial fluid samples is acquired as described in Example 4 and immediately frozen at −20 OC. Levels of MMP-9, MMP-14, TIMP-1 and relaxin in the samples is measured using commercial ELISA kits.

Quantification of Capsular Morphological Changes

After perfusion, both shoulders (immobilized and contralateral) are harvested, and the length of the synovial intima is measured as described in Example 4. Immunohistochemical staining is performed to assess the distribution of type III collagen in the joint as described in Example 4.

Pharmacokinetic Profiling

Tail vein blood draws are performed on days 3, 6, 9, 14, 28, and 56 of the post-immobilization period to determine relaxin kinetics using a commercial ELISA kit.

Statistical Analysis for Examples 4 and 7

One of the main outcome measures for the in vivo studies (Examples 4 and 7) is total ROM, which is defined as the difference between the minimum and maximum angles achieved with baseline $\tau_{OUT}$ and $\tau_{INT}$ as the driving forces of the passive motion. Mean ROM is calculated at each time point (baseline, and weeks 2, 4 and 8) and repeated-measures analysis of variance (ANOVA) are used to detect differences between intervention groups. Assuming a standard deviation of 14.3° (see Example 2), every group requires 9 animals per time point to achieve 80% power to detect a difference of 20° in mean ROM. Synovial intima length, expression of MMP-9, MMP-14 and TIMP-1 and collagen III staining intensity outcomes are treated as continuous variables and are compared between groups at each time point using repeated measures ANOVA. The loading portions of the nonlinear shoulder torque rotation data are pooled across cycles for subsequent analysis. Rotational stiffness is calculated for negative and positive loading data using a polynomial fit through MATLAB 7.2 software (MathWorks Inc, Natick, Mass., USA). The slopes of the various polynomial fits are compared using the Wald test. For Example 5, all the data recorded for the mechanical, swelling, and in vitro assays is expressed as a mean±standard deviation (N=3). Continuous variables are compared across groups using one-way ANOVA.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

```
                         LISTING OF SEQUENCES

SEQ ID NO: 1
>gi|116497221|gb|AAI26416.1| Relaxin 2 [Homo sapiens]
MPRLFFFHLLGVCLLLNQFSRAVADSWMEEVIKLCGRELVRAQIAICGMSTWSKRSLSQEDAPQTPRPVA
EIVPSFINKDTETINMMSEFVANLPQELKLTLSEMQPALPQLQQHVPVLKDSSLLFEEFKKLIRNRQSEA
ADSSPSELKYLGLDTHSRKKRQLYSALANKCCHVGCTKRSLARFC SEQ ID NO: 2
>gi|116496899|gb|AAI26420.1| Relaxin 2 [Homo sapiens]
MPRLFFFHLLGVCLLLNQFSRAVADSWMEEVIKLCGRELVRAQIAICGMSTWSKRSLSQEDAPQTPRP
VA
EIVPSFINKDTETINMMSEFVANLPQELKLTLSEMQPALPQLQQHVPVLKDSSLLFEEFKKLIRNRQS
EA
ADSSPSELKYLGLDTHSRKKRQLYSALANKCCHVGCTKRSLARFC SEQ ID NO: 3
>gi|313884020|gb|ADR83496.1| relaxin 2, partial [synthetic
construct]
MPRLFFFHLLGVCLLLNQFSRAVADSWMEEVIKLCGRELVRAQIAICGMSTWSKRSLSQEDAPQTPRP
VA
EIVPSFINKDTETINMMSEFVANLPQELKLTLSEMQPALPQLQQHVPVLKDSSLLFEEFKKLIRNRQS
EA
ADSSPSELKYLGLDTHSRKKRQLYSALANKCCHVGCTKRSLARFC SEQ ID NO: 4
>gi|13543609|gb|AAH05956.1| Relaxin 1 [Homo sapiens]
MPRLFLFHLLEFCLLLNQFSRAVAAKWKDDVIKLCGRELVRAQIAICGMSTWSKRSLSQEDAPQTPRP
VA
EIVPSFINKDTETIIIMLEFIANLPPELKAALSERQPSLPELQQYVPALKDSNLSFEEFKKLIRNRQS
EA
ADSNPSELKYLGLDTHSQKKRRPYVALFEKCCLIGCTKRSLAKYC SEQ ID NO: 5
>gi|119579171|gb|EAW58767.1| relaxin 1, isoform CRA_a [Homo sapiens]
MPRLFLFHLLEFCLLLNQFSRAVAAKWKDDVIKLCGRELVRAQIAICGMSTWSKRSLSQEDAPQTPRP
VA
EIVPSFINKDTETIIIMLEFIANLPPELKAALSERQPSLPELQQYVPALKDSNLSFEEFKKLIRNRQS
EA
ADSNPSELKYLGLDTHSQKKRRPYVALFEKCCLIGCTKRSLAKYC SEQ ID NO: 6
>gi|119579172|gb|EAW58768.1| relaxin 1, isoform CRA_b [Homo sapiens]
MPRLFLFHLLEFCLLLNQFSRAVAAKWKDDVIKLCGRELVRAQIAICGMSTWSKRSLSQEDAPQTPRPVA
GISSSLLRRRLFEDHDGPSFLV SEQ ID NO: 7
>gi|119579173|gb|EAW58769.1| relaxin 1, isoform CRA_c [Homo sapiens]
MLEFIANLPPELKAALSERQPSLPELQQYVPALKDSNLSFEEFKKLIRNRQSEAADSNPSELKYLGLDTH
SQKKRRPYVALFEKCCLIGCTKRSLAKYC SEQ ID NO: 8
>gi|119604794|gb|EAW84388.1| relaxin 3 [Homo sapiens]
MARYMLLLLLAVWVLTGELWPGAEARAAPYGVRLCGREFIRAVIFTCGGSRWRRSDILAHEAMGDTFPDA
DADEDSLAGELDEAMGSSEWLALTKSPQAFYRGRPSWQGTPGVLRGSRDVLAGLSSSCCKWGCSKSEISS
LC
```

LISTING OF SEQUENCES

SEQ ID NO: 9
>gi|187954661|gb|AAI40936.1| Relaxin 3 [Homo sapiens]
MARYMLLLLLAVWVLTGELWPGAEARAAPYGVRLCGREFIRAVIFTCGGSRWRRSDILAHEAMGDTFPDA
DADEDSLAGELDEAMGSSEWLALTKSPQAFYRGRPSWQGTPVVLRGSRDVLAGLSSSCCKWGCSKSEISS
LC SEQ ID NO: 10
>gi|17484096|gb|AAL40345.1|AF447451_1 relaxin 3 [Homo sapiens]
MARYMLLLLLAVWVLTGELWPGAEARAAPYGVRLCGREFIRAVIFTCGGSRWRRSDILAHEAMGDTFPDA
DADEDSLAGELDEAMGSSEWLALTKSPQAFYRGRPSWQGTPGVLRGSRDVLAGLSSSCCKWGCSKSEISS
LC SEQ ID NO: 11
>gi|317373369|sp|P51460.2|INSL3_HUMAN RecName: Full = Insulin-like 3;
MDPRLPAWALVLLGPALVFALGPAPTPEMREKLCGHHFVRALVRVCGGPRWSTEARRPATGGDRELLQWL
ERRHLLHGLVADSNLTLGPGLQPLPQTSHHHRHHRAAATNPARYCCLSGCTQQDLLTLCPY SEQ ID NO: 12
>gi|19579176|gb|EAW58772.1| insulin-like 4 (placenta) [Homo sapiens]
MASLFRSYLPAIWLLLSQLLRESLAAELRGCGPRFGKHLLSYCPMPEKTFTTTPGGWLLESGRPKEMVST
SNNKDGQALGTTSEFIPNLSPELKKPLSEGQPSLKKIILSRKKRSGRHRFDPFCCEVICDDGTSVKLCT SEQ ID NO: 13
>gi|20070773|gb|AAH26254.1| Insulin-like 4 (placenta) [Homo sapiens]
MASLFRSYLPAIWLLLSQLLRESLAAELRGCGPRFGKHLLSYCPMPEKTFTTTPGGWLLESGRPKEMVST
SNNKDGQALGTTSEFIPNLSPELKKPLSEGQPSLKKIILSRKKRSGRHRFDPFCCEVICDDGTSVKLCT SEQ ID NO: 14
>gi|37183178|gb|AAQ89389.1| INSL5 [Homo sapiens]
MKGSIFTLFLFSVLFAISEVRSKESVRLCGLEYIRTVIYICASSRWRRHLEGIPQAQQAETGNSFQLPHK
REFSEENPAQNLPKVDASGEDRLWGGQMPTEELWKSKKHSVMSRQDLQTLCCTDGCSMTDLSALC SEQ ID NO: 15
>gi|4768935|gb|AAD29686.1|AF133816_1 insulin-like peptide INSL5 [Homo
sapiens]
MKGSIFTLFLFSVLFAISEVRSKESVRLCGLEYIRTVIYICASSRWRRHLEGIPQAQQAETGNSFQLPHK
REFSEENPAQNLPKVDASGEDRLWGGQMPTEELWKSKKHSVMSRQDLQTLCCTDGCSMTDLSALC SEQ ID NO: 16
>gi|5059419|gb|AAD39003.1|AF156094_1 insulin-like protein 6 [Homo sapiens]
MPRLLRLSLLWLGLLLVRFSRELSDISSARKLCGRYLVKEIEKLCGHANWSQFRFEEETPFSRLIAQASE
KVEAYSPYQFESPQTASPARGRGTNPVSTSWEEAVNSWEMQSLPEYKDKKGYSPLGKTREFSSSHNINVY
IHENAFFQKKRRNKIKTLSNLFWGHHPQRKRRGYSEKCCLTGCTKEELSIACLPYIDFKRLKEKRSSLVT
KIY SEQ ID NO: 17
Elastase cleavage site
AAAAA SEQ ID NO: 18
Metalloproteinase-2 cleavage site
ESLAYYTA

---

What is claimed is:

1. A method for treating a stiffened joint resulting from fibrosis in a subject in need thereof, the method comprising administering to the subject an effective amount of relaxin-2 or a mutant thereof, such that the stiffened joint resulting from fibrosis in the subject is treated; wherein the relaxin-2 or a mutant thereof does not include relaxin attached to an immunoglobulin or a fragment of an immunoglobulin; wherein the relaxin-2 or a mutant thereof comprises an amino acid sequence having at least 95% sequence identity with any of SEQ ID NOS: 1-3; and wherein the relaxin-2 or a mutant thereof treats the stiffened joint by treating fibrosis; and wherein the stiffened joint resulting from fibrosis comprises adhesive capsulitis.

2. The method of claim 1, wherein the relaxin-2 or a mutant thereof comprises an amino acid sequence having at least 99% sequence identity with any of SEQ ID NOS: 1-3.

3. The method of claim 1, wherein the stiffened joint resulting from fibrosis is selected from the group consisting of a shoulder joint, an elbow joint, a wrist joint, a finger joint, a hip joint, a knee joint, and an ankle joint.

4. The method of claim 1, wherein the relaxin-2 or a mutant thereof is administered as a part of a sustained-release formulation.

5. The method of claim 4, wherein the sustained-release formulation is a hydrogel further comprising at least one polymer.

6. The method of claim 5, wherein the at least one polymer is selected from the group consisting of polyethylene glycol (PEG), alginate, agarose, poly(ethylene glycol dimethacrylate), polylactic acid, polyglycolic acid, PLGA, gelatin, collagen, agarose, pectin, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly(uronic acid), poly(anhydride) and poly(vinylpyrrolidone).

7. The method of claim 6, wherein the polymer is PEG.

8. The method of claim 7, wherein the PEG is covalently attached to the relaxin-2 or a mutant thereof.

9. The method of claim 8, wherein the hydrogel is formed in situ following mixing of the relaxin-2 or a mutant thereof and a cross-linker, wherein the cross-linker comprises:
   a polypeptide reactive moiety covalently attached to PEG and a linker as illustrated by the following schematic:

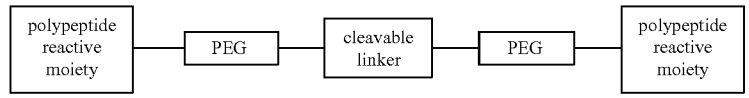

wherein:
   the polypeptide reactive moiety comprises at least one amine- or a thiol-reactive group; and
   the linker comprises a moiety cleavable via a chemical or an enzymatic reaction.

10. The method of claim 9, wherein the cross-linker has the following structural formula:

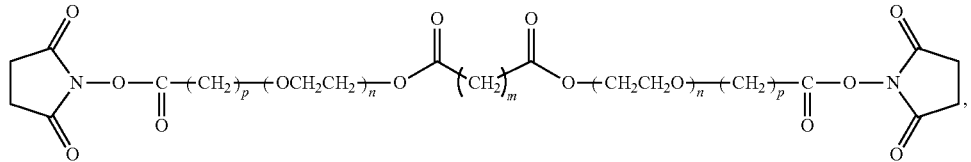

wherein:
   n is 20-500;
   m is any number from 1 to 10; and
   p is any number from 1 to 6.

11. The method of claim 8, wherein the hydrogel additionally comprises a filler polypeptide covalently attached to the PEG.

12. The method of claim 1, wherein the relaxin-2 or a mutant thereof is administered by an intraarticular injection.

13. A method for treating a stiffened joint resulting from fibrosis in a subject in need thereof, the method comprising administering to the subject an effective amount of relaxin-2 or a mutant thereof, such that the stiffened joint resulting from fibrosis in the subject is treated wherein the relaxin-2 or a mutant thereof does not include relaxin attached to an immunoglobulin or a fragment of an immunoglobulin; wherein the relaxin-2 or a mutant thereof comprises an amino acid sequence having at least 95% sequence identity with any of SEQ ID NOS: 1-3; and wherein the relaxin-2 or a mutant thereof treats the stiffened joint by treating fibrosis; and wherein the stiffened joint resulting from fibrosis comprises fibrosis involving capsule of the joint.

14. The method of claim 13, wherein the relaxin-2 or a mutant thereof comprises an amino acid sequence having at least 99% sequence identity with any of SEQ ID NOS: 1-3.

15. The method of claim 13, wherein the stiffened joint resulting from fibrosis is selected from the group consisting of a shoulder joint, an elbow joint, a wrist joint, a finger joint, a hip joint, a knee joint, and an ankle joint.

16. The method of claim 13, wherein the relaxin-2 or a mutant thereof is administered as a part of a sustained-release formulation.

17. The method of claim 16, wherein the sustained-release formulation is a hydrogel further comprising at least one polymer.

18. The method of claim 17, wherein the at least one polymer is selected from the group consisting of polyethylene glycol (PEG), alginate, agarose, poly(ethylene glycol dimethacrylate), polylactic acid, polyglycolic acid, PLGA, gelatin, collagen, agarose, pectin, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly(uronic acid), poly(anhydride) and poly(vinylpyrrolidone).

19. The method of claim 18, wherein the polymer is PEG.

20. The method of claim 19, wherein the PEG is covalently attached to the relaxin-2 or a mutant thereof.

21. The method of claim 20, wherein the hydrogel is formed in situ following mixing of the relaxin-2 or a mutant thereof and a cross-linker, wherein the cross-linker comprises:

a polypeptide reactive moiety covalently attached to PEG and a linker as illustrated by the following schematic:

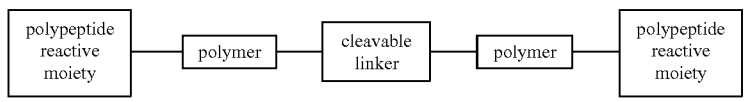

wherein:
the polypeptide reactive moiety comprises at least one amine- or a thiol-reactive group; and
the linker comprises a moiety cleavable via a chemical or an enzymatic reaction.

22. The method of claim 21, wherein the cross-linker has the following structural formula:

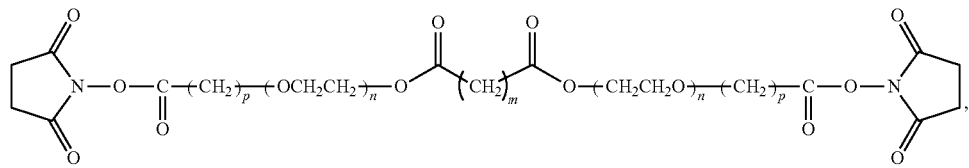

wherein:

n is 20-500;

m is any number from 1 to 10; and p is any number from 1 to 6.

23. The method of claim 20, wherein the hydrogel additionally comprises a filler polypeptide covalently attached to the PEG.

24. The method of claim 13, wherein the relaxin-2 or a mutant thereof is administered by an intraarticular injection.

* * * * *